(12) United States Patent
Gribble et al.

(10) Patent No.: US 9,205,113 B2
(45) Date of Patent: *Dec. 8, 2015

(54) SYNTHETIC TRITERPENOIDS AND METHODS FOR MODULATING STEM/PROGENITOR CELL GENE EXPRESSION

(71) Applicant: Trustees of Dartmouth College, Hanover, NH (US)

(72) Inventors: Gordon W. Gribble, Lebanon, NH (US); Liangfeng Fu, West Lebanon, NH (US); Michael B. Sporn, Tunbridge, VT (US); Karen T. Liby, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/395,157

(22) PCT Filed: May 7, 2013

(86) PCT No.: PCT/US2013/039902
§ 371 (c)(1),
(2) Date: Oct. 17, 2014

(87) PCT Pub. No.: WO2013/169740
PCT Pub. Date: Nov. 14, 2013

(65) Prior Publication Data
US 2015/0104429 A1   Apr. 16, 2015

Related U.S. Application Data

(63) Continuation of application No. 13/466,456, filed on May 8, 2012, now Pat. No. 8,921,419.

(60) Provisional application No. 61/644,080, filed on May 8, 2012.

(51) Int. Cl.
| | | |
|---|---|---|
| *A61K 31/56* | (2006.01) |
| *A61K 35/44* | (2015.01) |
| *C07C 61/29* | (2006.01) |
| *C07J 63/00* | (2006.01) |
| *C07C 62/38* | (2006.01) |
| *C07C 229/50* | (2006.01) |
| *C07C 235/78* | (2006.01) |
| *C07C 255/47* | (2006.01) |
| *C07C 291/10* | (2006.01) |
| *C07C 317/44* | (2006.01) |
| *C07C 323/55* | (2006.01) |
| *A61K 35/12* | (2015.01) |
| *C07C 62/32* | (2006.01) |

(52) U.S. Cl.
CPC ............... *A61K 35/44* (2013.01); *A61K 31/56* (2013.01); *A61K 35/12* (2013.01); *C07C 61/29* (2013.01); *C07C 62/32* (2013.01); *C07C 62/38* (2013.01); *C07C 229/50* (2013.01); *C07C 235/78* (2013.01); *C07C 255/47* (2013.01); *C07C 291/10* (2013.01); *C07C 317/44* (2013.01); *C07C 323/55* (2013.01); *C07J 63/008* (2013.01); *C07C 2103/52* (2013.01)

(58) Field of Classification Search
USPC .......................................... 514/510
See application file for complete search history.

(56) References Cited

U.S. PATENT DOCUMENTS

| | | | |
|---|---|---|---|
| 4,395,423 A | 7/1983 | Neumann | 424/304 |
| 4,808,614 A | 2/1989 | Hertel | 514/45 |
| 5,013,649 A | 5/1991 | Wang et al. | 435/69.1 |
| 5,064,823 A | 11/1991 | Lee et al. | 514/198 |
| 5,401,838 A | 3/1995 | Chou | 536/281 |
| 5,426,183 A | 6/1995 | Kjell | 536/285.5 |
| 5,464,826 A | 11/1995 | Grindey et al. | 514/50 |
| 5,521,294 A | 5/1996 | Wildfeuer | 536/187 |

(Continued)

FOREIGN PATENT DOCUMENTS

| | | | |
|---|---|---|---|
| CN | 101302243 | * | 12/2004 |
| CN | 100007348 | * | 2/2006 |

(Continued)

OTHER PUBLICATIONS

Abraham, N. G. and Kappas, A. "Heme Oxygenase and the Cardiovascular-Renal System" Free Radical Biology and Medicine 2005 39(1):1-25.

Agarwal, N. and Mehta, K. "Possible Involvement of Bcl-2 Pathway in Retinoid X Receptor Alpha-Induced Apoptosis of HL-60 Cells" Biochemistry and Biophysical Research Communications 1997 230(2):251-253.

Ahmad et al. "Triterpenoid CDDO-Me Blocks the NF-κB Pathway by Direct Inhibition of IKKβ on Cys-179" The Journal of Biological Chemistry 2006 281:35764-35769.

Al-alami et al. "Divergent Effect of Taxol on Proliferation, Apoptosis and Nitric Oxide Production in MHH225 CD34 Positive and U937 CD34 Negative Human Leukemia Cells" Leukemia Research 1998 22:939-945.

(Continued)

*Primary Examiner* — Shirley V Gembeh
(74) *Attorney, Agent, or Firm* — Licata & Tyrrell P.C.

(57) ABSTRACT

Synthetic triterpenoids and methods of using the same to induce gene expression and differentiation of stem or progenitor cells are provided. Furthermore, the present invention provides methods for producing a cell, such as a stem or progenitor cell, with induced gene expression by contacting a stem or progenitor cell with an effective amount of a synthetic triterpenoid to induce the expression of one or more of SOX9 (Sex determining region Y-box 9), COL2A1 (Type II Collagen (alpha1)), TGF-βI, TGF-p2, TGF-33, BMP2, BMP4, BMPRII (Bone Morphogenic Protein Receptor II), SMAD (Small Mothers Against Decapentaplegic) 3, SMAD4, SMAD6, SMAD7, TIMP (Tissue Inhibitor of Metalloproteinase)-1 or TIMP-2 in the stem or progenitor cell, wherein the stem or progenitor cell is not a mesenchymal stem cell, periosteum cell or osteoprogenitor cell. In one embodiment, the stem or progenitor cell is multipotent.

4 Claims, No Drawings

(56) References Cited

U.S. PATENT DOCUMENTS

| | | | |
|---|---|---|---|
| 5,597,124 A | 1/1997 | Kessel et al. | 241/30 |
| 5,603,958 A | 2/1997 | Morein et al. | 424/489 |
| 5,606,048 A | 2/1997 | Chou et al. | 536/271.1 |
| 5,972,703 A | 10/1999 | Long et al. | 435/372 |
| 6,025,395 A | 2/2000 | Breitner et al. | 514/570 |
| 6,303,569 B1 | 10/2001 | Greenwald et al. | 514/2 |
| 6,326,507 B1 | 12/2001 | Gribble et al. | 558/415 |
| 6,485,756 B1 | 11/2002 | Aust et al. | 424/725 |
| 6,552,075 B2 | 4/2003 | Gribble et al. | 514/522 |
| 6,974,801 B2 | 12/2005 | Honda et al. | 514/25 |
| 7,176,237 B2 | 2/2007 | Honda et al. | 514/519 |
| 7,265,096 B2 | 9/2007 | Gallop et al. | 514/49 |
| 7,288,568 B2 | 10/2007 | Gribble et al. | 514/519 |
| 7,435,755 B2 | 10/2008 | Konopleva et al. | 514/510 |
| 7,795,305 B2 | 9/2010 | Konopleva et al. | 514/510 |
| 7,863,327 B2 | 1/2011 | Gribble et al. | 514/521 |
| 7,915,402 B2 | 3/2011 | Anderson et al. | 540/519 |
| 7,943,778 B2 | 5/2011 | Jiang et al. | 548/247 |
| 8,034,955 B2 | 10/2011 | Gribble et al. | 548/241 |
| 8,129,429 B2 | 3/2012 | Sporn et al. | 514/510 |
| 8,299,046 B2 | 10/2012 | Sporn et al. | 514/63 |
| 8,921,340 B2 | 12/2014 | Sporn et al. | 514/63 |
| 2003/0119732 A1 | 6/2003 | Konopleva et al. | 514/510 |
| 2005/0276836 A1 | 12/2005 | Wilson et al. | 424/434 |
| 2005/0288363 A1 | 12/2005 | Gribble et al. | 558/303 |
| 2007/0155742 A1 | 7/2007 | Honda et al. | 514/519 |
| 2008/0220057 A1 | 9/2008 | Gribble et al. | 514/522 |
| 2008/0233195 A1 | 9/2008 | Spoorn et al. | 424/486 |
| 2008/0261985 A1 | 10/2008 | Honda et al. | 548/400 |
| 2009/0018146 A1 | 1/2009 | Gutterman et al. | 540/519 |
| 2009/0048204 A1 | 2/2009 | Walling et al. | 514/49 |
| 2009/0048205 A1 | 2/2009 | Meyer et al. | 514/49 |
| 2009/0060873 A1* | 3/2009 | Sporn et al. | 424/85.6 |
| 2009/0093447 A1 | 4/2009 | Konopleva et al. | 514/510 |
| 2009/0326063 A1 | 12/2009 | Sporn et al. | 514/529 |
| 2010/0048887 A1 | 2/2010 | Anderson et al. | 540/8 |
| 2010/0048892 A1 | 2/2010 | Anderson et al. | 544/154 |
| 2010/0048911 A1 | 2/2010 | Jiang et al. | 548/250 |
| 2011/0245206 A1 | 10/2011 | Jiang et al. | 514/112 |
| 2011/0245233 A1 | 10/2011 | Anderson et al. | 514/212.04 |

FOREIGN PATENT DOCUMENTS

| | | | |
|---|---|---|---|
| CN | 101117348 | | 2/2006 |
| CN | 101117348 | * | 2/2008 |
| DE | 10 2005 041613 | | 3/2007 |
| EP | 0272891 A2 | | 6/1988 |
| EP | 0329348 B1 | | 7/1995 |
| EP | 0376518 B1 | | 11/1995 |
| EP | 0576230 B1 | | 4/1996 |
| EP | 0577303 B1 | | 10/1997 |
| EP | 0712860 B1 | | 12/2001 |
| WO | WO 91/15498 | | 10/1991 |
| WO | WO 96/05290 | | 2/1996 |
| WO | WO 98/00173 | | 1/1998 |
| WO | WO 98/32762 | | 7/1998 |
| WO | WO 99/33483 | | 7/1999 |
| WO | WO 99/65478 | | 12/1999 |
| WO | WO 00/73253 | | 12/2000 |
| WO | WO 01/01135 | | 1/2001 |
| WO | WO 01/28579 | | 4/2001 |
| WO | WO 02/03996 | | 1/2002 |
| WO | WO 02/47611 | | 6/2002 |
| WO | WO 03/043631 | | 5/2003 |
| WO | WO 03/059339 | | 7/2003 |
| WO | WO 2004/064723 A2 | | 8/2004 |
| WO | WO 2005/042002 | | 5/2005 |
| WO | WO 2005/046732 | | 5/2005 |
| WO | WO 2006/029221 | | 3/2006 |
| WO | WO 2007/005879 | | 1/2007 |
| WO | WO 2007/069895 | | 6/2007 |
| WO | WO 2008/064132 A2 | | 5/2008 |
| WO | WO 2008/111497 | | 9/2008 |
| WO | WO 2008/136838 | | 11/2008 |
| WO | WO 2009/023232 | | 2/2009 |
| WO | WO2009/023835 A2 | | 2/2009 |
| WO | WO2010/093944 A2 | | 8/2010 |

OTHER PUBLICATIONS

Ambs et al. "p53 and Vascular Endothelial Growth Factor Regulate Tumor Growth of NOS2-Expressing Human Carcinoma Cells" Nature Medicine 1998 4(12):1371-1376.
Amstutz et al. "Die Position 5 Im Oxotremorin-Gerust: Eine Zentrale Stelle Fur Die Steuerung Der Aktivitat Am Muscarinischen Rezeptor" Helvitica Chemi Acta 1987 70:2232-2244.
Andreeff et al. "Expression of Bcl-2-Related Genes in Normal and AML Progenitors: Changes Induced by Chemotherapy and Cationic Acid" Leukemia 1999 13:1881-1892.
Andreeff et al. "PPARgamma Nuclear Receptor as a Novel Molecular Target in Leukemias" 2002 Keystone Symposia Abstract No. 501, 2002.
Andreef, M. "Acute Myeloid Leukemia" Cancer Treatment 1995 911-922.
Araujo et al. "Systemic Rather than Local Heme Oxygenase-1 Overexpression Improves Cardiac Allograft Outcomes in a New Transgenic Mouse" The Journal of Immunology 2003 171(3):1572-1580.
Bach, F. H. "Heme Oxygenase-1 and Transplantation Tolerance" Human Immunology 2006 67(6):430-432.
Baeuerle, P. A. and Baltimore, D. "NF-κB: Ten Years After" Cell 1996 87:13-20.
Bagasra et al. "Activation of the Inducible Form of Nitric Oxide Synthase in the Brains of Patients with Multiple Sclerosis" Proceedings of the National Academy of Science USA 1995 92:12041-12045.
Baldwin Jr., A. S. "The NF-κB and IκB Proteins: New Discoveries and Insights" Annual Review of Immunology 1996 14:649-681.
Bargou et al. "Constitutive Nuclear Factor κB-RelA Activation is Required for Proliferation and Survival of Hodgkin's Disease Tumor Cells" The Journal of Clinical Investigation 1997 100:2961-2969.
Barkett, M. and Gilmore, T. D. "Control of Apoptosis by Rel/NF-κB Transcription Factors" Oncogene 1999 18:6910-6924.
Barnes, P. J. and Karin, M. "Nuclear Factor-κB—A Pivotal Transcription Factor in Chronic Inflammation Diseases" The New England Journal of Medicine 1997 336:1066-1071.
Beal, M. F. "Mitochondria, Free Radicals, and Neurodegeneration" Current Opinion in Neurobiology 1996 6:661-666.
Beran et al. "Topotecan and Cytarabine is an Active Combination Regimen in Myelodysplastic Syndromes and Chronic Myelomonocytic Leukemia" Journal of Clinical Oncology 1999 17(9):2819-2830.
Bliard et al. "Glycosylation of Acids Under Phase Transfer Conditions. Partial Synthesis of Saponins" Tetrahedron Letters 1994 35:6107-6108.
Bogdan et al. "Contrasting Mechanisms for Suppression of Macrophage Cytokine Release by Transforming Growth Factor-Beta and Interleukin-10" The Journal of Biological Chemistry 1992 267:23301-23308.
Bogdan, C. and Ding, A. "Taxol, a Microtubule-Stabilizing Antineoplastic Agent, Induces Expression of Tumor Necrosis Factor α and Interleukin-1 in Macrophages" Journal of Leukocyte Biology 1992 52(1):119-121.
Bollag, W. and Holdener, E. E. "Retinoids in Cancer Prevention and Therapy" Annals of Oncology 1992 3:513-526.
Boolbol et al. "Cyclooxygenase-2 Overexpression and Tumor Formation are Blocked by Sulindac in a Murine Model of Familial Adenomatous Polyposis" Cancer Research 1996 56(11):2556-2560.
Bore et al. "The Anti-Inflammatory Triterpenoid Methyl 2-Cyano-3, 12-Dioxoolean 1,9(11)-dien-28-oate Methanol Solvate Hydrate" Acta Crystallography C. 2002 58 (Pt 3) : o199-o200.
Brookes et al. "The Triterpenoid 2-cyano-3,12-dioxooleana-1,9-dien-28-oic Acid and Its Derivatives Elicit Human Lymphoid Cell Apoptosis Through a Novel Pathway Involving the Unregulated Mitochondrial Permeability Transition Pore" Cancer Research 2007 67:1793-1802.

(56) References Cited

OTHER PUBLICATIONS

Bruder, S. P. and Caplan, A. I. "Terminal Differentiation of Osteogenic Cells in the Embryonic Chick Tibia is Revealed by a Monoclonal Antibody Against Osteocytes" Bone 1990 11:189-198.
Bruder, S. P. and Caplan, A. I. "First Bone Formation and the Dissection of an Osteogenic Lineage in the Embryonic Chick Tibia is Revealed by Monoclonal Antibodies Against Osteoblasts" Bone 1989 10:359-375.
Bruder et al. "Terminal Osteogenic Cell Differentiation in Culture Requires Beta-Glycerol Phosphate" Transactions of the Annual Meeting—Orthopaedic Research Society 1991 16:58.
Bruland et al. "Expression and Characteristics of a Novel Human Osteosarcoma-Associated Cell Surface Antigen" Cancer Research 1988 48:5302-5308.
Buzoni-Gatel et al. "Intraepithelial Lymphocytes Traffic to the Intestine and Enhance Resistance to Toxoplasma Gondii Oral Infection" The Journal of Immunology 1999 162:5846-5852.
Buzoni-Gatel et al. "Murine Ileitis After Intracellular Parasite Infection is Controlled by TGF-Beta-Producing Intraepithelial Lymphocytes" Gastroenterology 2001 120:914-924.
Cai et al. "A New Protecting Group for Alkynes: Orthogonally Protected Dialkynes" Helvetica Chimica Acta 1995 78:732-757.
Carter et al. "Expression of Survivin, A member of the Inhibitor of Apoptosis (IAP) Family of Caspase Inhibitors is Expressed in AML and Regulated by Cytokines and ATRA" Blood 1999 94 (Suppl 1) : 479a, Abstract #2142.
Cassady, J. M. and Suffness, M. In *Anticancer Agents Based on Natural Product Models*; Academic Press, NY, 254-269, 1980.
Castaigne et al. "All-Trans Retinoic Acid as a Differentiation Therapy for Acute Promyelocytic Leukemia" Blood 1990 76(9):1704-1709.
Chauhan et al. "The Bortezomib/Proteasome Inhibitor PS-341 and Triterpenoid CDDO-Im Induce Synergistic Anti-Multiple Myeloma (MM) Activity and Overcome Bortezomib Resistance" Blood 2004 103:3158-3166.
Chen et al. "Chondrogenesis in Chick Limb Bud Mesodermal Cells: Reciprocal Modulation by Activin and Inhibin" Experimental Cell Research 1993 206:119-127.
Chen et al. "Stimulation of Chondrogenesis in Limb Bud Mesoderm Cells by Recombinant Human Bone Morphogenetic Protein 2B(BMP-2B) and Modulation by Transforming Growth Factor Beta 1 and Beta 2" Experimental Cell Research 1991 195:509-515.
Cheng et al. "Differentiation of Human Bone Marrow Osteogenic Stromal Cells in vitro: Induction of the Osteoblast Phenotype by Dexamethasone" Endocrinology 1994 134:277-286.
Chintharlapalli et al. "2-Cyano-3,12-dioxoolean-1,9-dien-28-oic Acid and Related Compounds Inhibit Growth of Colon Cancer Cells Through Peroxisome Proliferator-Activated Receptor Gamma-Dependent and -Independent Pathways" Molecular Pharmacology 2005 68:119-128.
Chung, J. Y. L. and Wasicak, J. T. "Synthesis of Chiral α-Acetylenic Cyclic Amines from α-Amino Acids: Applications to Differentially Constrained Oxotremorine Analogues as Muscarinic Agents" Tetrahedron Letters 1990 31:3957-3960.
Clinton et al. "Steroidal[3,2-c]pyrazoles. II. Androstanes, 19-Norandrostanes and Their Unsaturated Analogs" Journal of the American Chemical Society 1961 83:1478-1491.
Corey, E. J. and Ruden, R. A. "Stereoselective Methods for the Synthesis of Terminal *cis* and *trans* Enye Units" Tetrahedron Letters 1973:1495-1499
Coyle, J. T. and Puttfarcken, P. "Oxidative Stress, Glutamate, and Neurodegenerative Disorders" Science 1993 262:689-695.
Dean, P.D.G. "Halogenolysis of Methyl Glycyrrhetate with Lithium Iodidedimethylformamide" Journal of the Chemical Society 1965:6655-6659.
Dezube et al. "Interim Results of a Phase I Trial with a Novel Orally Administered Synthetic Triterpenoid RTA 402 (CDDO-Me) in Patients with Solid Tumors and Lymphoid Malignancies" Journal of Clinical Oncology 2007 ASCO Annual Meeting Proceedings 25 (18S) : 1401.

Ding et al. "Macrophage Deactivating Factor and Transforming Growth Factors-$\beta_1$, -$\beta_2$, and -$\beta_3$ Inhibit Induction of Macrophage Nitrogen Oxide Synthesis by IFN-$\gamma^1$" Journal of Immunology 1990 145(3):940-944.
Dinkova-Kostova et al. "Extremely Potent Triterpenoid Inducers of the Phase 2 Response: Correlations of Protection Against Oxidant and Inflammatory Stress" The Proceedings of the National Academy of Science U.S.A. 2005 102(12):4584-4589.
Drach et al. "Induction of Differentiation in Myeloid Leukemia Cell Lines and Acute Promyelocytic Leukemia Cells by Liposomal All-Trans-Retinoic Acid" Cancer Research 1993 53:2100-2104.
Dragnev et al. "The Retinoids and Cancer Prevention Mechanisms" The Oncologist 2000 5:361-368.
Drefahl and Huneck "Nor-olea-12-enol-17-amin und Olea-12-enol-28-amin" Chemisch Berichte 1958 91:278-281.
DuBois et al. "$G_1$ Delay in Cells Overexpressing Prostaglandin Endoperoxide Synthase-$2^1$ " Cancer Research 1996 56(4):733-737.
DuBois et al. "Increased Cyclooxygenase-2 Levels in Carcinogen-Induced Rat Colonic Tumors" Gastroenterology 1996 110:1259-1262.
Dutcher et al. "Pentacyclic Triterpene Synthesis. 5. Synthesis of Optically Pure Ring AB Precursors" Journal of Organic Chemistry 1976 41:2663-2669.
Elliot et al. "The Triterpenoid CDDO Inhibits Expression of Matrix Metalloproteinase-1, Matrix Metalloproteinase-13 and Bcl-3 in Primary Human Chondrocytes" Arthritis Research Therapy 2003 5:R285-R291.
Elsawa et al. "Preferential Inhibition of Malignant Cell Growth by CDDO in Waldenstrom Macroglobulinemia" Blood 2006 108(11):2528.
Elstner et al. "Ligands for Peroxisome Proliferator-Activated Receptorgamma and Retinoic Acid Receptor Inhibit Growth and Induce Apoptosis of Human Breast Cancer Cells in vitro and in BNX Mice" Proceedings of the National Academy Science USA 1998 95:8806-8811.
Embleton et al. "Antitumor Reactions of Monoclonal Antibody Against a Human Osteogenic-Sarcoma Cell Line" British Journal of Cancer 1981 43:4801-4805.
Engel et al. "Quantitation of Minimal Residual Disease in Acute Myelogenous Leukemia and Myelodysplastic Syndromes in Complete Remission by Molecular Cytogenetics of Progenitor Cells" Leukemia 1999 13:568-577.
Estey et al. "Molecular Remissions Induced by Liposomal-Encapsulated All-Trans Retinoic Acid in Newly Diagnosed Acute Promyelocytic Leukemia" Blood 1999 94:2230-2235.
Estey et al. "Randomized Phase II Study of Fludarabine + Cytosine Arabinoside + Idarubicin + All-Trans Retinoic Acid + Granulocyte-Colony Stimulating Factor in Poor Prognosis Newly Diagnosed Acute Myeloid Leukemia and Myelodysplastic Syndrome" Blood 1998 93(8):2478-2484.
Favaloro et al. "Design and Synthesis of Tricyclic Compounds with Enone Functionalities in Rings A and C: A Novel Class of Highly Active Inhibitors of Nitric Oxide Production in Mouse Marcophages" Journal of Medicinal Chemistry 2002 45:4801-4805.
Finkbeiner, H. L. and Stiles, M. "Chelation as a Driving Force in Organic Reactions. IV. Synthesis of a α-Nitro Acids by Control of the Carboxylastion-Decarboxylation Equilibrium" Journal of the American Chemical Society 1963 85:616-622.
Genain, C. P. and Hauser, S. L. "Creation of a Model for Multiple Sclerosis in Callithrix Jacchus Marmosets" Journal of Molecular Medicine 1997 75:187-197.
Ghosh et al. "NF-κB and Rel Proteins: Evolutionarily Conserved Mediators of Immune Response" Annual Review of Immunology 1998 16:225-260.
Grieco, P. A. and Speake, J. D. "Synthetic Studies on Quassinoids: Total Synthesis and Biological Evaluation of (+)-Des-D-Chaparrinone" The Journal of Organic Chemistry 1998 63:5929-5936.
Gura, T. "Systems for Identifying New Drugs are Often Faulty" Science 1997 278:1041-1042.
Guttridge et al. "NF-kappaB Controls Cell Growth and Differentiation Through Transcriptional Regulation of Cyclin D1" Molecular and Cellular Biology 1999 19:57855799.

(56) References Cited

OTHER PUBLICATIONS

Hail et al. "Evidence Supporting a Role for Calcium in Apoptosis Induction by the Synthetic Triterpenoid 2-cyano-3,12-dioxooleana-1,9-dien-28-oic Acid (CDDO)" The Journal of Biological Chemistry 2004 279:11179-11187.
Heiner et al. "Localization of GD2-Specific Monoclonal Antibody 3F8 in Human Osteosarcoma" Cancer Research 1987 47:5377-5384.
Hidvegi et al. "A Low Temperature Method of Isolating Normal Human Articular Chondrocytes" Osteoarthritis and Cartilage 2006 14:89-93.
Hinz et al. "NF-kappaB Function in Growth Control: Regulation of Cyclin D1 Expression and G0/G1-to-S-phase Transtion" Molecular and Cellular Biology 1999 19:2690-2698.
Hirota et al. "Stereoselective Total Synthesis of (±) -eperuane-8β,15-diol$^1$ " Bulletin of the Chemical Society of Japan 1988 61:4023-4028.
Hirota et al. "Suppression of Tumor Promoter-Induced Inflammation of Mouse Ear by Ursolic Acid and 4,4-dimethycholestane Derivatives" Agricultural and Biological Chemistry 1990 54:1073-1075.
Hirota et al. "Total Synthesis of (±)-amarolide, a Quassinoid Bitter Principle" Journal of Organic Chemistry 1991 56:1119-1127.
Honda et al. "A Novel Dicyanotriterpenoid, 2-cyano-3,12-dioxooleanan-1,9(11)-dien-28-onitrile, Active at Picomolar Concentrations for Inhibition of Nitric Oxide Production" Bioorganic & Medicinal Chemistry Letters 2002 12:1027-1030.
Honda et al. "Design and Synthesis of 2-cyano-3,12-dioxoolean-1,9-dien-28-oic Acid, A Novel and Highly Active Inhibitor of Nitric Oxide Production in Mouse Marcophages" Bioorganic & Medicinal Chemistry Letters 1998 8(19):2711-2714.
Honda et al. "Efficient Synthesis of (−)- and (+)- Tricyclic Compounds with Enome Functionalities in Rings A and C. A Novel Class of Orally Active Anti-Inflammatory and Cancer Chemopreventive Agents" Organic and Bimolecular Chemistry 2003 1:4384-4391.
Honda et al. "New Enone Derivatives of Oleanolic Acid and Ursolic Acid as Inhibitors of Nitric Oxide Production in Mouse Marcophages" Bioorganic & Medicinal Chemistry Letters 1997 7:1623-1628.
Honda et al. "Novel Synthetic Oleanane and Ursane Triterpenoids with Various Enone Functionalities in Ring A as Inhibitors of Nitric Oxide Production in Mouse Marcophages" Journal of Medicinal Chemistry 2000 43:1866-1877.
Honda et al. "Novel Synthetic Oleanane Triterpenoids: A Series of Highly Active Inhibitors of Nitric Oxide Production in Mouse Macrophages" Bioorganic & Medicinal Chemistry Letters 1999 9(24):3429-3434.
Honda et al. "Synthesis of (±)-3,3-ethylenedioxy-14α-hydroxy-5-picrasene-11,16-dione, a 14αH-Picrasane Derivative" Chemistry Letters 1981:299-302.
Honda et al. "Synthesis of a Novel Dicyano Abietane Analogue: a Potential Antiinflammatory Agent" The Journal of Organic Chemistry 2006 71:3314-3316.
Honda et al. "Synthetic Oleanane and Ursane Triterpenoids with Modified Rings A and C: a Series of Highly Active Inhibitors of Nitric Oxide Production in Mouse Macrophages" The Journal of Medicinal Chemistry 2000 43:4233-4246.
Honda et al. "An Efficient Synthesis of Tricyclic Compounds, (±)-(4αβ,8αβ,10αα)- 1,2,3,4,4a,6,7,8,8a,9,10,10a,-Dodechaydro-1,1 4a-trimethyl-2-Oxophenanthrene-8a-Carboxylic Acid, Its Methyl Ester, and (±)-(4αβ, Baβ, 10aα)-3,4,4a,6,7,8,8a,9,10,10a-Decahydro-8a-Hydroxmethyl-1,1, 4a-Trimethylphenanthren-2 (1H)-One" Organic Preparations and Procedures International 2005 37:546-550.
Hosoi et al. "Detection of Human Osteosarcoma-Associated Antigen(s) by Monoclonal Antibodies" Cancer Research 1982 42:654-661.
Huang et al. "Inhibition of Skin Tumorigenesis by Rosemary and Its Constituents Carnosol and Ursolic Acid" Cancer Research 1994 54:701-708.
Huang et al. "Inhibitory Effects of Dietary Curcumin on Forestomach, Duodenal, and Colon Carcinogenesis in Mice" Cancer Research 1994 54:5841-5847.
Huang et al. "Structure of a WW Domain Containing Fragment of Dystrophin in Complex with β-Dystroglycan" Nature Structural and Molecular Biology 2000 7:634-638.
Hyer et al. "Synthetic Triterpenoids Cooperate with Tumor Necrosis Factor-Related Apoptosis-Inducing Ligand to Induce Apoptosis of Breast Cancer Cells" Cancer Research 2005 65:4799-4808.
Iguchi et al. "Lipid Peroxidation and Disintegration of the Cell Membrane Structure in Cultures of Rat Lung Fibroblasts Treated with Asbestos" Journal of Applied Toxicology 1993 13:269-275.
Ikeda et al. "Induction of Redox Imbalance and Apoptosis in Multiple Myeloma Cells by the Novel Triterpenoid 2-cyano-3,12-dioxoolean-1,9-dien-28-oic Acid" Molecular Cancer Therapeutics 2004 3:39-45.
Ikeda et al. "The Novel Triterpenoid CDDO and Its Derivatives Induce Apoptosis by Disruption of Intracellular Redox Balance" Cancer Research 2003 63:5551-5558.
Ishikawa et al. "Herne Oxygenase-1 Inhibits Antherogenesis in Watanabe Heritable Hyperlipidemic Rabbits" Circulation 2001 104(15):1813-1836.
Ito et al. "Involvement of Caspase-8 in the Induction of Osteosarcoma Cell Apoptosis by the Novel Triterpenoid CDDO" 47$^{th}$ Annual Meeting, Orthopaedic Research Society, Feb. 25-28, 2001, San Francisco, California, p. 0863, Poster Session, 2001.
Ito et al. "The Novel Triterpenoid 2-cyano-3, 12-dioxoolean-1,9-dien-28-oic Acid Induces Apoptosis of Human Myeloid Leukemia Cells by a Caspase-8-dependent Mechanism" Cell Growth & Differentiation 2000 11(5):261-267.
Ito et al. "The Novel Titerpenoid CDDO Induces Apoptosis and Differentiation of Human Osteosarcoma Cells by a Caspase-8 Dependent Mechanism" Molecular Pharmacology 2001 59:1094-1099.
Johansen et al. "Pharmacology and Preclinical Pharmacokinetics of the Triterpenoid CDDO Methyl Ester" Proceedings of the American Associate for Cancer Research 2003 44:1728.
Johnson et al. "A Plan for Distinguishing Between Some Five- and Six-Membered Ring Ketones" Journal of the American Chemical Society 1945 67:1745-1754.
Johnson et al. "Relationships Between Drug Activity in NCI Preclinical in vitro and in vivo Models and Early Clinical Trials" British Journal of Cancer 2001 84:1424-1431.
Joyce et al. "Integration of Rac-Dependent Regulation of Cyclin D1 Transcription Through a Nuclear Factor-KappaB-Dependent Pathway" Journal of Biological Chemistry 1999 275:25245-25249.
Kahne, D. and Collum, D. B. "Kinetic Cyanations of Ketone Enolates" Tetrahedron Letters 1981 22:5011-5014.
Kaltschmidt et al. "Transcription Factor NF-kappaB is Activated in Primary Neurons by Amyloid Beta Peptides and in Neurons Surrounding Early Plaques from Patients with Alzheimer Disease" Proceedings of the National Academy of Science USA 1997 94:2642-2647.
Karin, M. "Nuclear Factor-kappaB in Cancer Development and Progression" Nature 2006 441:431-436.
Kawamori et al. "Chemopreventive Activity of Celecoxib, As Specific Cyclooxygenase-2 Inhibitor, Against Colon Carcinogenesis" Cancer Research 1998 58(3):409-412.
Kerwin et al. "Quassinoid Synthesis. 2. Preparation of a Tetracyclic Intermediate Having the Bruceantin Tetrahydrofuran Ring" Journal of Organic Chemistry 1987 52:1686-1695.
Khan et al. "A Dichotomous Role for Nitric Oxide During Acute Toxoplasma Gondii Infection in Mice" Proceedings of the National Acadmey of Science USA 94:1997 13955-13960.
Kim et al. "Capasase-3 Activation is Involved in Apoptosis Induced by a Synthetic Triterpenoid in Non-Small Cell Lung Cancer (NSCLC) Cells" Proceedings of the American Association for Cancer Research 2000 41:770, Abstract #4894.
Kim et al. "Identification of a Novel Synthetic Triterpenoid, Mehtyl-2-cyano-3,12-dioxooleana-1,9-dien-28-oate, That Potently Induces Caspase-Mediated Apoptosis in Human Lung Cancer Cells" Molecular Cancer Therapeutics 2002 1:177-184.
Kircher, H. W. "Triterpenes, in Organ Pipe Cactus" Phytochemistry 1980 19:2707-2712; Database Caplus on STN AN:1981:550946.
Konopleva, M. and Andreeff, M. "Regulatory Pathways in Programmed Cell Death" Cancer Molecular Biology 1999 6:1229-1260.

(56) References Cited

OTHER PUBLICATIONS

Konopleva et al. "Activation of Nuclear Transcription Factor PPARgamma by the Novel Triterpenoid CDDO as Targeted Therapy in Breast Cancer" 2002 Keystone Symposium, Abstract No. 539, 2002.
Konopleva et al. "Apoptosis Molecules and Mechanisms" Advances in Experimental Biology and Medicine 1998 457:217-236.
Konopleva et al. "Engraftment Potential of AML Progenitors into NOD/Scid Mice is Dependent on Baseline CXCR4 Expression" Blood 1999 94(Suppl 1):166b, Abstract #3916.
Konopleva et al. "Mechanisms and Activity of PPARgamma-Active Triterpenoids CDDO and CDDO-Me in Leukemias" Blood 2005 106:2460.
Konopleva et al. "Novel Synthetic Triterpenoid CDDO-Me: Potent Antiproliferative, Proapoptotic and Differentiating Agent in AML" Blood 2000 96(11), Part 1:121A, Abstract #522.
Konopleva et al. "Novel Synthetic Triterpenoid, CDDO, and Its Methyl Ester: Potent Antiproliferative, Proapoptotic and Differentiating Agents in AML" Blood 1999 94(Suppl 1):479a, Abstract #2140.
Konopleva et al. "Novel Triterpenoid CDDO-Me is a Potent Inducer of Apoptosis and Differentiation in Acute Myelogenous Leukemia" Blood 2002 99(1):326-335.
Konopleva et al. "Peroxisome Proliferator-Activated Receptor Gamma and Retinoid X Receptor Ligands are Potent Inducers of Differentiation and Apoptosis in Leukemias" Molecular Cancer Therapeutics 2004 3:1249-1262.
Konopleva et al. "PPARγ Nuclear Receptor as a Novel Therapeutic Target in AML" Blood 2000 96(11):460a, Abstract #1982.
Konopleva et al. "PPARgamma Ligand CDDO Induces Apoptosis in Leukemias Via Multiple Apoptosis Pathways" Abstracts of the 44$^{th}$ Annual Meeting of the American Society of Hematology 2002 Abstract No. 2209.
Konopleva et al. "PPARgamma Ligands Are Potent Inducers of Apoptosis in Leukemias and Lymphomas" American Society of Hematology 43$^{rd}$ Annual Meeting and Exposition 2001 Abstract No. 501.
Konopleva et al. "PPARgamma Nuclear Receptor as a Novel Molecular Target in Leukemia Therapy" Proceedings of the American Association for Cancer Research 2002 43:4730.
Konopleva et al. "PPARgamma Nucelar Receptor as a Novel Therapeutic Target in AML" Proceedings of the American Association for Cancer Research 2001 42:4458.
Konopleva et al. "Suppression of ERK Activation is Required for Triterpenoid Methyl-CDDO-Induced Apoptosis in AML" Blood 2003 102(11):1404.
Konopleva et al. "Synthetic Titerpenoid 2-cyano-3,12-dioxooleana-1,9-dien-28-oic Acid Induces Growth Arrest in HER2-Overexpressing Breast Cancer Cells" Molecular Cancer Therapy 2006 5:317-328.
Konopleva et al. "Synthetic Triterpenoid CDDO as a Novel Therapy for Resistant Breast Cancer" Proceedings of the American Association for Cancer Research 2003 44:2726.
Konopleva et al. "The Novel Triterpenoid CDDO-Me Suppresses MAPK Pathways and Promotes p38 Activation in Acute Myeloid Leukemia Cells" Leukemia 2005 19:1350-1354.
Konopleva et al. "The Synthetic Triterpenoid 2-cyano3,12-dioxooleana-1,9-dien-28-oic Acid Induces Caspase-Dependent and -Independent Apoptosis in Acute Myelogenous Leukemia" Cancer Research 2004 64:7927-7935.
Konopleva et al. "Triterpenoid Methyl-CDDO Is a Potent Inducer of Apoptosis in CD34+ AML Progenitor Cells Via Activation of SAPK Pathways and Inhibition of MAPK Cascades" Blood 2004 104:2533.
Kornblau et al. "Apoptosis Regulating Proteins as Targets of Therapy for Hematological Malignancies" Expert Opinion on Investigational Drugs 1999 8:2027-2057.
Kornblau et al. "Phase I Study of Mitoxantrone Plus Etoposide with Multidrug Blockage by SDZ PSC-833 in Relapsed or Refractory Acute Myelogenous Leukemia" Journal of Clinical Oncology 1997 15(5):1796-1802.
Kowalski, C. J.and Reddy, R. E. "Ester Homologation Revisited: A Reliable, Higher Yielding and Better Understood Procedure" Journal or Organic Chemistry 1992 57:7194-7208.
Kress et al. "Triterpenoids Display Single Agent Activity in a Mouse Model of CLL/SBL" Blood 2006 108(11):2530.
Kress et al. "Triterpenoids Display Single Agent Anti-Tumor Activity in a Transgenic Mouse Model of Chronic Lymphocytic Leukemia and Small B Cell Lymphoma" PLoS One 2007 6(e559):1-11.
Kruger et al. "Up-Regulation of Heme Oxygenase Provides Vascular Protection in an Animal Model of Diabetes Through Its Antioxidant and Antiapoptotic Effects" Journal of Pharmacology and Experimental Therapeutics 2006 319:1144-1152.
Kurbacher et al. "Ascorbic Acid (Vitamin C) Improves the Antineoplastic Activity of Doxorubicin, Cisplatin, and Paclitaxel in Human Breast Carcinoma Cells in vitro" Cancer Letters 1996 103:183-189.
Kurinna et al. "The Novel Triterpenoid CDDO-Me Promotes Apoptosis in Gleevec-Resistant Chronic Myeloid Leukemia Cells by Caspase-Independent Mechanisms" Proceedings of the American Association for Cancer Research 2005 46:2240.
Langille et al. "Differential Effects of Physiological Concentrations of Retinoic Acid in vitro on Chondrogenesis and Myogenesis in Chick Craniofacial Mesenchyme" Differentiation 1989 40:84.
Lapillonne et al. "Activation of Peroxisome Proliferator-Activated Receptor Gamma by a Novel Synthetic Triterpenoid 2-cyano-3,12-dioxooleana-1,9-dien-28-oic Acid Induces Growth Arrest and Apoptosis in Breast Cancer Cells" Cancer Research 2003 63:5926-5939.
Lawson et al. "Isolation and Preliminary Characterization of Monoclonal Antibody That Interacts Preferentially with the Liver Isoenzyme of Human Alkaline Phosphatase" Clinical Chemistry 1985 31:381-385.
Lee et al. "Functional and Quantitative Analysis of Splenic T Cell Immune Responses Following Oral Toxoplasma Gondii Infection Mice" Experimental Parasitology 1999 91:212-221.
Lemieux, R. U. "Acylglycosyl Halides. [55] Tetra-O-acetyl-α-D-glucopyranosyl Bromide" Methods in Carbohydrate Chemistry 1963 2:221-222.
Liby et al. "The Synthetic Triterpenoids, CDDO and CDDO-Imidazolide, are Potent Inducers of Heme Oxygenase-1 and Nrf2/ARE Signaling" Cancer Research 2005 65:4789-4798.
Liby et al. "Triterpenoids and Rexinoids as Multifunctional Agents for the Prevention and Treatment of Cancer" Nature Reviews 7:357-369.
Lieu et al. "Dual Cytotoxic Mechanisms of Submicromolar Taxol on Human Leukemia HL-60 Cells" Biochemical Pharmacology 1997 53:1587-1596.
Ling et al. "The Novel Triterpenoid C-28 Methyl Ester of 2-Cyano-3,12-dioxoolen-1,9-dien-28-oic Acid Inhibits Metastic Murine Breast Tumor Growth Through Inactivation of STAT3 Signaling" Cancer Research 2007 67:4210-4218.
Ling et al. "The Novel Triterpenoid CDDO-Me Inhibits Metastic Murine Breast Tumor Through Inhibition of Stat3 Signaling" 2007 AACR Annual Meeting, Abstract No. 301, 2007.
Liotta et al. "A Simple Method for the Efficient Synthesis of Unsaturated β-Dicarbonyl Compounds" Journal of Organic Chemistry 1981 46:2920-2923.
Liu et al. "Heme Oxygenase-1 (HO-1) Inhibits Postmyocardial Infarct Remodeling and Restores Ventricular Function" The FASEB Journal 2006 20(2):207-216.
Long et al. "Regulation of Human Bone Marrow-Derived Osteoprogenitor Cells by Osteogenic Growth Factors" Journal of Clinical Investigation 1995 95:881-887.
MacMicking et al. "Altered Responses to Bacterial Infection and Endotoxic Shock in Mice Lacking Inducible Nitric Oxide Synthase" 1995 Cell 81:641-650.
Marnett, L. J. "Asprin and the Potential Role of Prostaglandins in Colon Cancer" Cancer Research 1992 52(20):5575-5589.
McGeer, P. L. and McGeer, E. G. "The Inflammatory Response System of Brain: Implications for Therapy of Alzheimer and Other Neurodegenerative Diseases" Brain Research Reviews 1995 21:195-218.

(56) References Cited

OTHER PUBLICATIONS

Mehta et al. "Activation of Retinoid Receptors RAR Alpha and RXT Alpha Induces Differentiation and Apoptosis, Respectively, in HL-60 Cells" Cell Growth and Differentiation 1996 7(2):179-186.

Melichar et al. "Growth-Inhibitory Effect of a Novel Synthetic Triterpenoid, 2-cyano-3,12-dioxoolean-1,9-dien-28-oic Acid, on Ovarian Carcinoma Cell Lines Not Dependent on Peroxisome Proliferator-Activated Receptor-Gamma Expression" Gynecologic Oncology 2004 93:149-154.

Mella et al. "1,2-dideoxy-3, 4:5, 7-bis-$o$-(1 Methylethylidene)-D-gluco- and -D-galacto-hept-1-ynitols: Synthesis and Conformational Studies" Tetrahedron 1988 44:1673-1678.

Merril, J. E. and Benveniste, E. N. "Cytokines in Inflammatory Brain Lesions: Helpful and Harmful" Trends in Neurosciences 1996 19:331-338.

Minns et al. "A Novel Triterpenoid Induces Transforming Growth Factor Beta Production by Intraepithelial Lymphocytes to Prevent Ileitis" Gastroenterology 2004 127:119-126.

Mix et al. "A Synthetic Triterpenoid Selectively Inhibits the Induction of Matrix Metalloproteinases 1 and 13 by Inflammatory Cytokines" Arthritis and Rheumatism 2001 44:1096-1104.

Mix et al. "Peroxisome Proliferator-Activated Receptor-Gamma-Independent Repression of Collagenase Gene Expression by 2-cyano-3,12-dioxooleana-1,9-dien-28-oic Acid and Prostaglandin 15-deoxy-delta(12,14)J2: A Role for Smad Signaling" Molecular Pharmacology 2004 65:309318.

Moncada et al. "Nitric Oxide: Physiology, Pathophysiology, and Pharmacology" Pharmacology Review 1991 43:109-142.

Morse, D. and Choi, A. M. K. "Heme Oxygenase-1: From Bench to Bedside" American Journal of Respiratory and Critical Care Medicine 2005 172(6):660-670.

Murphy et al. "Immunomodulatory Effects of the Triterpenoid CDDO After Allogeneic Bone Marrow Transplantation in Mice: Reduction of Acute Graf-tVersus-Host Disease Lethality" Blood 2005 106:1316.

Murray, R. E. and Zweifel, G. "Preparation of Phenyl Cyanate and Its Utilization for the Synthesis of $\alpha$, $\beta$-Unsaturated Nitriles" Synthesis 1980 2:150-151.

Muzart, J. "Synthesis of Unsaturated Carbonyl Compounds via a Chromium-Mediated Allylic Oxidation by 70% Tert. butylhyrdoperoxide" Tetrahedron Letters 1987 28:4665-4668.

Nathan, C. and Xie, Q. "Nitric Oxide Synthases: Roles, Tolls and Controls" Cell 1994 78:915-918.

Nicholson et al. "Lethality of Endotoxin in Mice Genetically Deficient in the Respiratory Burst Oxidase, Inducible Nitric Oxide Synthase, or Both" Shock 1999 11:253-258.

Nishino et al. "Inhibition of the Tumor-Promoting Action of 12-O Tetradecanoylphorbol-13-acetate by Some Oleanane-Type Triterpenoid Compounds" Cancer Research 1988 48:5210-5212.

Ohshima, H. and Bartsch, H. "Chronic Infections and Inflammatory Process as Cancer Risk Factors: Possible Role of Nitric Oxide in Carinogenesis" Mutation Research 1994 305:253-264.

Omura, K. and Swern, D. "Oxidation of Alcohols by 'Activated' Dimethyl Sulfoxide. A Preparative Steric and Mechanistic Study" Tetrahedron 1978 34:1651-1660.

Ono et al. "A Convenient Procedure for Esterification of Carboxylic Acids" Bulletin of the Chemical Society of Japan 1978 51:2401-2404.

Oshima et al. "Suppression of Intestinal Polyposis in Apc$^{\Delta 716}$ Knockout Mice by Inhibition of Cyclooxygenase 2(COX-2)" Cell 1996 87:803-809.

Pahl, H. L. "Activators and Target Genes of Rel/NF-κB Transcription Factors" Oncogene 1999 18:6853-6866.

Palcy, S. and Goltzman, D. "Protein Kinase Signalling Pathways Involved in the Up-Regulation of the Rat Aplha1(I) Collagen Gene by Transforming Growth Factor Betal and Bone Morphogenetic Protein 2 in Osteoblastic Cells" Biochmemistry Journal 1999 343:21-27.

Paul et al. "Design and Synthesis of a Self-Assembled Photochemical Dyad Based on Selective Imidazole Recognition" Inorganic Chemistry 2002 41:3699-3704.

Paul et al. "Effective Expression of Small Interfering RNA in Human Cells" Nature Biotechnology 2002 20:505-508.

Pedersen et al. "The Triterpenoid CDDO Induces Apoptosis in Refactory CLL B Cells" Blood 2002 100:2965-2972.

Picard et al. "The Triterpene Reinols and Related Acids, Part VI" Journal of the Chemical Society 1939:1045-1048.

Place et al. "The Novel Synthetic Triterpenoid, CDDO-Imidazolide, Inhibits Inflammatory Response and Tumor Growth in vivo" Clinical Cancer Research 2003 9:2798-2806.

Prescott, S. M. and White, R. L. "Self-Promotion? Intimate Connections Between APC and Prostaglandin H Synthase-2" Cell 1996 87:783-786.

Rayet, B. And Gélinas, C. "Aberrant rel/nfkb Genes and Activity in Human Cancer" Oncogene 1999 18:6938-6947.

Reddy et al. "Evaluation of Cyclooxygenase-2 Inhibitor for Potential Chemopreventive Properties in Colon Carcinogenesis" Cancer Research 1996 56(20):4566-4569.

Rossi et al. "Anti-Inflammatory Cyclopentenone Prostaglandins are Direct Inhibitors of IkappaB Kinase" Nature 2000 403:103-108.

Ruvolo et al. "The Novel Triterpenoid Methyl-CDDO Inhibits Bc12 Phosphorylation and Potently Kolls U937 Cells" Blood 1999 94(10), Suppl. 1, Part 1:280A, Abstract #1251.

Sacerdoti et al. "Heme Oxygenase Overexpression Attenuates Glucose-Mediated Oxidative Stress in Quiescent Cell Phase: Linking Heme to Hyperglycemia Complications" Current Neurovascular Research 2005 2(2):103-111.

Salvemini et al. "Endogenous Nitric Oxide Enhances Prostaglandin Production in a Model of Renal Inflammation" Journal of Clinical Investigation 1994 93(5):1940-1947.

Salvemini et al. "Nitric Oxide Activates Cyclooxygenase Enzymes" Proceedings of the National Academy of Science USA 1993 90(15):7240-7244.

Samudio et al. "2,cyano-3,12 dioxoolean-1,9 diene-28-imidazolide Induces Apoptosis in Pancreatic Cancer via Redox-Dependent Cytoplasmic Stress" Proceedings of the American Association for Cancer Research 2005 46:5899.

Samudio et al. "2-Cyano-3,12-dioxooleana-1,9-dien-28-imidazolide (CDDO-Im) Directly Targets Mitochondrial Glutathione to Induce Apoptosis in Pancreatic Cancer" Journal of Biological Chemistry 2005 280:36273-36282.

Samudio et al. "A Novel Mechanism of Action of Methyl-2-cyano-3,12 dioxoolean-1,9 diene-28-oate: Direct Permeabiliztion of the Inner Mitochondrial Membrane to Inhibit Electron Transport and Induce Apoptosis" Molecular Pharmacology 2006 69:1182-1193.

Samudio et al. "A Novel Mechanism of Action of Methyl-2-cyano-3,12 dioxoolean-1,9 diene-28-oate (CDDO-Me): Direct Permabilization of the Inner Mitochondrial Membrane to Inhibit Electron Transport and Induce Apoptosis" Proceedings of the American Association for Cancer Research 2006 47:4693.

Samudio et al. "A Novel Mechanism of Action of Methyl-2-cyano-3,12 dioxoolean-1,9 diene-28-oate (CDDO-Me) : Direct Permeabilization of the Inner Mitochondrial Membrane to Inhibit Electron Transport and Induce Apoptosis" Blood 2005 106:4462.

Samudio et al. "The Novel Triterpenoid CDDOme Potently Synergizes with Inhibition of bcl-2 Function to Induce Apoptosis in AML via Disruption of Intracellular Redox Homeostasis" Proceedings of the American Association for Cancer Research 2005 46:4955.

Satoh et al. "Activation of the Keapl/Nrf2 Pathway for Neuroprotection by Electrophilic [Correction of Electrophillic] Phase II Inducers" Proceedings of the National Academy of Science USA 2006 103(3):768-773.

Scholz et al. "Sensitive and Specific Methods for the Determination of CDDO Methyl Ester in Mouse, Rat, Dog, Monkey, and Human Plasma by LC-Tandem Mass Spectrometry" Proceedings of the American Association of Cancer Research 2003 4:6321.

Seibert, K. and Masferrer, J. L. "Role of Inducible Cyclooxygenase(COX-2) in Inflammation" Receptor 1994 4(1):17-23.

Sharpless et al. "Electrophilic and Nucleophilic Oranoselenium Reagents. New Routes to Alpha, Beta-Unsaturated Carbonyl Compounds" Journal of the American Chemical Society 1973 95:6137.

(56) References Cited

OTHER PUBLICATIONS

Sheng et al. "A Selective Cyclooxygenase 2 Inhibitor Suppresses the Growth of H-ras-Transformed Rat Intestinal Epithelial Cells" Gastroenterology 1997 113(6):1883-1891.
Sheng et al. "Inhibition of Human Colon Cancer Cell Growth by Selective Inhibition of Cyclooxygenase-2" Journal of Clinical Investigation 1997 99(9):2254-2259.
Shishodia et al. "A Synthetic Triterpenoid, CDDO-Me, Inhibits IkappaBalpha Kinase and Enhances Apoptosis Induced by TNF and Chemotherapeutic Agents Through Down-Regulation of Expression of Nuclear Factor KappaB-Regulated Gene Products in Human Leukemic Cells" Clinical Cancer Research 2006 12:1828-1838.
Shull et al. "Identification of Vitamin D-Responsive Protein on the Surface of Human Osteosarcoma Cells" Proceedings of the National Academy of Science USA 1989 86:5405-5410.
Shull et al. "Morphologic and Biochemical Studies of Canine Mucopolysaccharidosis I" American Journal of Pathology 1984 114:487-495.
Simonian, N. A. and Coyle, J. T. "Oxidative Stress Neurodegenerative Diseases" Annual Review of Pharmacology and Toxicology 1996 36:83-106.
Simonsen et al. "Tetracyclic Hydroxy Acids" The Terpenes, Cambridge University, Cambridge 1957 5:221-285.
Singh et al. "Anti-Inflammatory Activity of Oleanolic Acid in Rats and Mice" Journal of Pharmacy and Pharmacology 1992 44:456-458.
Sive et al. "Expression of Chondrocyte Markers by Cells of Normal and Degenerate Intervertebral Discs" Molecular Pathology 2002 55:91-97.
Snitman et al. "Synthetic Approaches to Taxodione Synthesis of Methyl 12-oxopodocarpa-5,9(11)-diene-8β-carboxylate" Synthetic Communications 1978 8:187-194.
Sonogashira et al. "A Convenient Synthesis of Acetylenes: Catalytic Substitions of Acetylenic Hydrogen with Bromoakenes, Iodoarenes, and Bromopyridines" Tetrahedron Letters 1975 4467-4470.
Sporn, M. B. and Roberts, A. B. "Peptide Growth Factors and Inflammation, Tissue Repair, and Cancer" Journal of Clinical Investigation 1986 78:329-332.
Sporn et al. "Prospects for Prevention and Treatment of Cancer with Selective PPARγ Modulators (SPARMs)" Trends in Molecular Medicine 2001 7(9):395-400.
Sporn et al. "Transforming Growth Factor-Beta: Biological Function and Chemical Structure" Science 1986 233:532-534.
Stadheim et al. "The Novel Triterpenoid 2-cyano-3,12-dioxooleana-1,9-dien-28-oic Acid (CDDO) Potently Enhances Apoptosis Induced by Tumor Necrosis Factor in Human Leukemia Cells" Journal of Biological Chemistry 2002 277:16448-16455.
Sterzycki, R. Z. "Pyridinium Tosylate, A Mild Catalyst for Formation and Cleavage of Dioxolane-Type Acetals" Synthesis 1979 724-725.
Stewart et al. "Risk of Alzheimer's Disease and Duration of NSAID Use" Neurology 1997 48:626-632.
Suh et al. "A Novel Synthetic Oleanane Triterpenoid, 2- cyano-3,12-dioxoolean-1,9-dien-28-oic Acid (CDDO), Induces Cell Differentiation in Human Myeloid Leukemias" Proceedings of the American Association for Cancer Research Annual Meeting 1999 40:300, Abstract #1988.
Suh et al. "A Novel Synthetic Oleanane Triterpenoid, 2-cyano-3,12-dioxoolen-1,9-dien-28-oic Acid, With Potent Differentiating, Antiproliferative, and Anti-Inflmmatory Activity" Cancer Research 1999 59(2):336-341.
Suh et al. "Novel Triterpenoids Suppress Inducible Nitric Oxide Synthase (iNOS) and Inducible Cyclooxygenase (COX-2) in Mouse Macrophages" Cancer Research 1998 58:717-723.
Suh et al. "Novel Triterpenoids Suppress Inducible Nitric Oxide Synthase (iNOS) and Inducible Cyclooxygenase(COX-2)" Proceedings of the American Association for Cancer Research Annual Meeting 1998 39:266.
Suh et al. "Synthetic Triterpenoids Activate a Pathway for Apoptosis in AML Cells Involving Downregulation of FLIP and Sensitization to TRAIL" Leukemia 2003 17:2122-2129.

Suh et al. "Synthetic Triterpenoids Enhance Transforming Growth Factor β/Smad Signaling" Cancer Research 2003 63:1371-1376.
Suh et al. "Triterpenoids CDDO and CDDO-Me Down-Regulate FLIP Expression and Sensitize AML Cells to Trail-Induced Apoptosis" American Society of Hematology 43rd Annual Meeting and Exposition 2001 Abstract No. 498.
Sun et al. "The Synthetic Trierpenoid, CDDO, Suppresses Alloreactive T Cell Responses and Reduces Murine Early Acute Graft-Versus-Host Disease Mortaility" Biology of Blood and Marrow Transplantation 2007 13:521-529.
Syftestad et al. "The in vitro Chondrogenic Response of Limb-Bud Mesenchyme to a Water-Soluble Fraction Prepared from Demineralized Bone Matrix" Differentiation 1985 29:230.
Tabe et al. "Chromatin-Mediated Transctional Activation with Novel Peroxisome Proliferator-Activated Receptor gamma(PPARgamma) Ligand 2-cyano-1,9-dien-28-oic Acid (CDDO) in Acute Promyelocytic Leukemia Cells" Abstracts of the 44th Annual Meeting of the American Society of Hematology 2002 Abstract No. 2191.
Takabe et al. "Synthesis of Lycosyl Esters of Oleanolic" Carbohydrate Research 1979 76:101-108, Database CAPLUS on STN An:1980:42278.
Takahashi et al. "Increased Expression of Inducible and Endothelial Constitutive Nitric Oxide Synthases in Rat Colon Tumors Induced by Azoxymethane" Cancer Research 1997 57:1233-1237.
Tamir, S. and Tannebaum, S. R. "The Role of Nitric Oxide (NO) in the Carcinogenic Process" Biochimic and Biophysica Acta 1996 1288:F31-F36.
Tamm et al. "Expression and Prognostic Significance of IAP-Family Genes in Human Cancers and Leukemia" Blood 1999 94(Suppl. 1):69a, Abstract #298.
Tenenbaum, H. C. and Heersche, J. N. M. "Differentiation of Osteoblasts and Formation of Mineralized Bone in vitro" Calcified Tissue International 1982 34:76.
Toriumi et al. "Mandibular Reconstruction with a Recombinant Bone-Inducing Factor. Functional, Histologic, and Biomechanical Evaluation" Archives Otolaryngology Head and Neck Surgery 1991 117:1101-1112.
Tsai et al. "Monoclonal Antibody to Human Osteosarcoma: A Novel Mr 26,000 Protein Recognized by Murine Hybridoma TMMR-2" Cancer Research 1990 50:152-161.
Tsao et al. "DRIP205 Co-Activator Overexpression Enhances PPARgamma-Mediated Differentiation of Leukemia Cells by CDDO" Proceedings of the American Association for Cancer Research 2005 46:1855.
Tsao et al. "Targeted Induction of Apoptosis in Leukemia by PPARgamma Ligation" American Society of Hematology 43rd Annual Meeting and Exposition 2001 Abstract No. 2381.
Tsujii, M. and DuBois, R. N. "Alterations in Cellular Adhesion and Apoptosis in Epithelial Cells Overexpressing Prosaglandin Endoperoxide Synthase 2" Cell 1995 83:493-501.
Tsujii et al. "Cyclooxygenases Regulates Angiogenesis Induced by Colon Cancer Cells" Cell 1998 93:705-716.
Turksen et al. "Isolation of Monoclona Antibodies Recognizing Rat Bone-Associated Molecules in vitro and in vivo" Journal of Histochemistry and Cytochemistry 1992 40:1339-1352.
Vazquez et al. "Human Immunodeficiency Virus Type 1-Induced Macrophage Gene Expression Includes the p21 Gene, a Target for Viral Regulation" Journal of Virology 2005 79:4479-4491.
Vukicevic et al. "Stimulation of the Expression of Osteogenic and Chondrogenic Phenotypes in vitro by Osteogenin" Proceedings of the National Academy of Science USA 1989 86:8793-8797.
Walczak et al. "Tumoricidal Activity of Tumor Necrosis Factor-Related Apoptosis-Including Ligand in vivo" Naure Medicine 1999 5(2):157-163.
Walsh et al. "Monoclonal Antibodies with Selective Reactivity Against Osteoblasts and Osteocytes in Human Bone" Journal of Bone and Mineral Research 1994 9:1687-1696.
Wang et al. "A Novel Synthetic Triterpenoid, 2-cyano-3,12-dioxoolean-1, 9-dien-28-oic Acid (CDDO) Induces Adipocyte Differentiaion in 3T3-L1 Cells" Proceedings of the American Association for Cancer Research Annual Meeting 1999 40:300, Abstract #1989.

(56) References Cited

OTHER PUBLICATIONS

Wang et al. "A Synthetic Triterpenoid, 2-cyano-3,12-dioxooleana-1,9-dien-28-oic Acid (CDDO), Is a Ligand for the Peroxisome Proliferator-activated Receptor γ" Molecular Endocrinology 2000 14:1550-1556.

Warrell et al. "Differentiation Therapy of Acute Promyelocytic Leukemia with Tretinoin (All-Trans-Retinoic Acid)" New England Journal of Medicine 1991 324(20):1385-1393.

Williams et al. "Immunology of Multiple Sclerosis" Journal of Clinical Neuroscience 1994 2(3-4):229-245.

Woodley, J. F. "Liposomes for Oral Administration of Drugs" Critical Reviews in Therapeutic Drug Carrier System 1985 2(1):1-18.

Xie et al. "Differential Expression Patterns in Human Myeloblastic Leukemia HL-60 and Multidrug Resistant HL-60/Dox Cells Analyzed by Human cDNA Expression Array" Blood 1998 92(Suppl 1):387a, Abstract #1600.

Yates et al. "Pharmacodynamic Characterization of Chemopreventive Triterpenoids as Exceptionally Potent Inducers of Nrf2-Regulated Genes" Molecular Cancer Therapeutics 2007 6:154-162.

Yates et al. "Potent Protection Against Aflatoxin-Induced Tumorigenesis Through Induction of Nrf2- Regulated Pathways by the Triterpenoid 1-[2-cyano-3- ,12-dioxooleana-1,9(11)-dien-28-oyl]imidazole" Cancer Research 2006 66:2488-2494.

Yue et al. "Depletion of Intracellular Glutathione Contributes to JNK-Mediated Death Receptor 5 Upregulation and Apoptosis Induction by the Novel Synthetic Triterpenoid Methyl-2-cyano-3,12-dioxooleana-1,9-dien-28-oate (CDDO-Me)" Cancer & Biology Therapy 2006 5(5):492-497.

Zapata et al. "CDDO and CDDO-Im Reduce Tumor Burden in a Transgenic Mouse Model of CLL" Blood 2004 104:3477.

Zapata et al. "Triterpenoids Show Activity Against Leukemic Cells in a Transgenic Mouse Model of CLL" Proceedings of the American Association for Cancer Research 2005 46:5179.

Zhang et al. "Synthetic Triterpenoid CDDO as Effective Therapy for HER2-Expressing Resistant Breast Cancer" Proceedings of the American Association for Cancer 2004 Abstract No. 3799.

Zhang et al. "The Novel Synthetic Oleanane Triterpenoid CDDO (2-cyano-3, 12-dioxoolean-1,9-dien-28-oic Acid) Induces Apoptosis in Mycosis Fungoides/Sézary Syndrome Cells" Journal of Investigative Dermatology 2004 123:380-387.

Zhou et al. "Carbon Monoxide Suppresses Bleomycin-Induced Lung Fibrosis" American Journal of Pathology 2005 166(1):27-37.

Zou et al. "c-Jun NH2-Terminal Kinase-Mediated Up-Regulation of Death Receptor 5 Contributes to Induction of Apoptosis by the Novel Synthetic Triterpenoid Methyl-2-cyano-3,12-dioxooleana-1,9-dien-28-oate in Human Lung Cancer Cells" Cancer Research 2004 64:7570-7578.

Office Communication dated Mar. 9, 2009 from U.S. Appl. No. 11/941,723, filed Nov. 16, 2007.

"CDDO in Treating Patients with Metastatic or Unresectable Solid Tumors or Lymphoma" http://www.clincialtrials.gov/ct2/show/NCT00352040?term=CDDO&rank=1, Dec. 14, 2008.

"FDA Mulls Drug to Slow Late-Stage Alzheimer's" http://www.cnn.com/2003/HEALTH/conditions/09/24/alzheimers.drug.ap/index.html, Retrieved on Sep. 23, 2003.

"Phase IIa Trail to Determine the Effects of Bardoxolone Methyl on Renal Function in Patients with Diabetic Nephropathy" http://www.clincialtrails.gov/ct2/show/NCT00664027?term=rta&rank=10, Dec. 14, 2008.

"RTA 402 in Advanced Solid Tumors or Lymphoid Malignancies" http://www.clinicaltrials.gov/ct2/show/NCT00508807?term=rta&rank=2&show_desc=Y, Dec. 14, 2008.

"Study to Assess the Safety, Tolerability, and Pharmacodynmics of RTA 402 in Patients with Hepatic Dysfunction" http://www.clinicaltrials.gov/ct2/show/NCT00550849?term=rta&rank=4, Dec. 14, 2008.

Akrivakis et al. "Prolonged Infusion of Gemcitabine in Stage IV Breast Cancer: A Phase I Study" Anti-Cancer Drugs 1999 10(6):525-531.

Alexander et al. "Synthesis and Cytotoxic Activity of Two Novel 1-dodecylthio-2-decyloxypropyl-3-phosphatidic Acid Conjugates with Gemcitabine and Cytosine Arabinoside" Journal of Medicinal Chemistry 2003 46(19):4205-4208.

Ardestani et al. "Effects of Dexamethasone and Betamethasone as COX-2 Gene Expression Inhibitors on Rigidty in a Rat Model of Parkinson's Disease" Indian Journal of Pharmacology 2007 39:235-239.

Ariga et al. "Role of Sphingolipid-Mediated Cell Death in Neurodegeneratvie Diseases" Journal of Lipid Research 1998 39:1-16.

Baker et al. "2'-Deoxy-2'-methylenecytidine and 2'-deoxy-2',2'-diflurocytidine 5'-diphosphates: Potent Mechanism-Based Inhibitors of Ribonucleotide Reductase" Journal of Medicinal Chemistry 1991 34(6):1884.

Balkwill et al. "Smoldering and Polarized Inflammation in the Initiation and Promotion of Malignant Disease" Cancer Cell 2005 7(3):211-217.

Cerwenka, A. and Swain, S. L. "TGF-β1: Immunosuppressant and Viability Factor for T Lymphocytes" Microbes and Infection 1999 1:1291-1296.

Cho et al. "The Transcription Factor NRF2 Protects Against Pulmonary Fibrosis" FASEB Journal 2004 18:1-29.

Chou et al. "Stereospecific Synthesis of 2-Deoxy-2,2-difluororibonolactone and Its Use in the Preparation of 2'-deoxy-2',2'-difluoro-B-D-ribofuranosyl Pyrimidine Nucleosides: The Key Role of Selective Crystallization" Synthesis 1992 565-570.

Cianchi et al. "Cyclooxygenase-2 Activation Mediates the Proangiogenic Effect of Nitric Oxide in Colorectal Cancer" Clinical Cancer Research 2004 10:2694-2704.

Cripe, L. D. "Adult Acute Leukemia" Current Problems in Cancer 1997 21(1):4-64.

Cui, Y. "A Material Science Perspective of Pharmaceutical Solids" International Journal of Pharmaceutics 2007 339(1-2):3-18.

Di Stefano et al. "Inhibition of [3H]thymidine Incorporation into DNA of Rat Regenerating Liver by 2',2'-difluorodeoxycytidine Coupled to Lactosaminated poly-L-lysine" Biochemical Pharmacology 1999 57(7):793-799.

Ekmekcioglu et al. "Tumor iNOS Predicts Poor Survival for Stage III Melanoma Patients" International Journal of Cancer 2006 119:861-866.

Ellies et al. "Mammary Tumor Latency is Increased in Mice Lacking the Inducible Nitric Oxide Synthase" International Journal of Cancer 2003 106:1-7.

Gandhi et al. "Prolonged Infusion of Gemcitabine: Clinical and Pharmacodynamics Studies During a Phase I Trial in Relapsed Acute Myelogenous Leukemia" Journal of Clinical Oncology 2002 20(3):665-673.

Godoy et al. "Central and Systemic IL-I Exacerbates Neurodegeneration and Motor Symptoms in a Model of Parkinson's Disease" Brain 2008 131:1880-1894.

Guo et al. "Selective Protection of 2',2'-Diflurodeoxycytidine (Gemcitabine)" Journal of Organic Chemistry 1999 64:8319-8322.

Guo et al. "Targeted Delivery of a Peripheral Benzodiazepine Receptor Ligand-Gemcitabine Conjugate to Brain Tumors in a Xenograft Model" Cancer Chemotherapy and Pharmacology 2001 48(2):169-176.

Honda et al. "Design, Synthesis, and Biological Evaluation of Biotin Conjugates of 2-cyano-3,12-dioxooleana-1,9(11)-dien-28-oic Acid for the Isolation of the Protein Targets" Journal of Medicinal Chemistry 2004 47(20):4923-4932.

Hong et al. "Phase I Trial of a Novel Oral NF-κB/pSTAT3 Inhibitor RTA-402 in Patients with Solid Tumors and Lymphoid Malignancies" 44th Annual Meeting of the American Society of Clinical Oncology, 2008.

Kasinski et al. "Inhibition of IkappaB Kinase-Nuclear Factor-kappaB Signaling Pathway by 3,5-bis(2-flurobenzylidene)piperidin-4-one (EF24), A Novel Monoketone Analog of Curcumin" Molecular Pharmacology 2008 74 (3):654-661.

Klotz et al. "Selective Expression of Inducible Nitric Oxide Synthase in Human Prostate Carcinoma" Cancer 1998 82:1897-1903.

(56) References Cited

OTHER PUBLICATIONS

Lala et al. "Role of Nitric Oxide in Tumor Progression: Lessons from Experimental Tumors" Cancer and Metastasis Reviews 1998 17(1):91-106.
Leonard et al. "Expression of Nitric Oxide Synthase in Inflammatory Bowel Disease is Not Affected by Corticosteriod Treatment" Journal of Clinical Pathology 1998 51:750-753.
Li, N. and Nel, A. E. "Role of the Nrf2-Mediated Signaling Pathway as a Negative Regulator of Inflammation: Implications for the Impact of Particulate Pollutants on Asthma" Antioxidants & Redox Signaling 2006 8:89-98.
Liby et al. "A Novel Acetylenic Tricyclic bis-(cyano enone) Potently Induces Phase 2 Cytoprotective Pathways and Blocks Liver Carcinogenesis Induced by Aflatoxin" Cancer Research 2008 68:6727-6733.
Liby et al. "The Rexinoid LG100268 and the Synthetic Triterpenoid CDDO-Methyl Amide are More Potent than Erlotinib for Prevention of Mouse Lung Carcinogenesis" Molecular Cancer Therapy 2008 7:1251-1257.
Luo et al. "IKK/NF-kappaB Signaling: Balancing Life and Death—A New Approach to Cancer Therapy" Journal of Clinical Investigation 2005 115(10):2625-2631.
Mantovani, A. "Inflammation by Remote Control" Nature 2005 435:752-753.
Marrogi et al. "Nitric Oxide Synthase, Cyclooxygenase 2 and Vascular Endothelial Growth Factor in the Angiogenesis of Non-Small Cell Lung Carcinoma" Clinical Cancer Research 2000 6:4739-4744.
Maurel et al. "Phase I Trial of Weekly Gemcitabine at 3-h Infusion in Refractory, Heavily Pretreated Advanced Solid Tumors" Anti-Cancer Drugs 2001 12(9):713-717.
Morris et al. "Association of a Functional Inducible Nitric Oxide Xynthase Promoter Variant with Complications in Type 2 Diabetes" Journal of Molecular Medicine 2002 80(2):96-104.
Morse, D. and Choi, A. M. "Heme Oxygenase-1: The 'Emerging Molecule' Has Arrived" American Journal of Respiratory and Critical Care Medicine 2002 27(1):8-16.
Na, H. and Surh, Y. "Transcriptional Regulation via Cysteine Thiol Modification: A Novel Molecular Strategy for Chemoprevention and Cytoprotection" Molecular Carcinogenesis 2006 45(6):360-380.
Nathan et al. "Protection from Alzheimer's-like Disease in the Mouse by Genetic Ablation of Inducible Nitric Oxide Synthase" The Journal of Experimental Medicine 2005 202:1163-1169.
Nathan, C. "Points of Control in Inflammation" Nature 2002 420:846-852.
Office Action in Canadian Patent App. No. 2,335,505, mailed Jan. 10, 2008.
Office Action in Canadian Patent App. No. 2,335,505, mailed Nov. 23, 2006.
Office Action in Canadian Patent App. No. 2,335,505, mailed Sep. 22, 2008.
Office Action in Canadian Patent App. No. 2,430,454, mailed Jan. 20, 2009.
Office Action in European Patent App. No. 01 989 130, mailed Jul. 31, 2008.
Office Action, in European Patent App. No. 03 729 681, mailed Nov. 6, 2008.
Office Action in European Patent App. No. 99 928 731, mailed Aug. 1, 2008.
Office Action in European Patent App. No. 99 928 731, mailed Dec. 9, 2008.
Office Action in European Patent App. No. 99 928 731, mailed Dec. 15, 2004.
Office Action in European Patent App. No. 99 928 731, mailed Feb. 14, 2007.
Office Action in U.S. Appl. No. 09/335,003, mailed Aug. 28, 2000.
Office Action in U.S. Appl. No. 09/335,003, mailed Mar. 15, 2001.
Office Action in U.S. Appl. No. 09/335,003, mailed Nov. 2, 2000.
Office Action in U.S. Appl. No. 09/927,081, mailed Feb. 22, 2002.
Office Action in U.S. Appl. No. 09/998,009, mailed Apr. 4, 2007.
Office Action in U.S. Appl. No. 09/998,009, mailed Jul. 11, 2005.
Office Action in U.S. Appl. No. 09/998,009, mailed Jul. 14, 2004.
Office Action in U.S. Appl. No. 09/998,009, mailed Jul. 3, 2006.
Office Action in U.S. Appl. No. 09/998,009, mailed Mar. 24, 2004.
Office Action in U.S. Appl. No. 09/998,009, mailed Nov. 30, 2005.
Office Action in U.S. Appl. No. 09/998,009, mailed Nov. 16, 2007.
Office Action in U.S. Appl. No. 09/998,009, mailed Oct. 20, 2004.
Office Action in U.S. Appl. No. 10/345,053, mailed Aug. 25, 2004.
Office Action in U.S. Appl. No. 10/345,053, mailed Dec. 23, 2004.
Office Action in U.S. Appl. No. 10/345,053, mailed Dec. 6, 2005.
Office Action in U.S. Appl. No. 10/345,053, mailed Mar. 1, 2006.
Office Action in U.S. Appl. No. 10/345,053, mailed May 31, 2005.
Office Action in U.S. Appl. No. 10/395,372, mailed Apr. 28, 2006.
Office Action in U.S. Appl. No. 10/395,372, mailed Aug. 4, 2005.
Office Action in U.S. Appl. No. 10/395,372, mailed Dec. 20, 2006.
Office Action in U.S. Appl. No. 10/395,372, mailed Feb. 7, 2007.
Office Action in U.S. Appl. No. 10/395,372, mailed Jan. 28, 2004.
Office Action in U.S. Appl. No. 10/395,372, mailed Jul. 9, 2004.
Office Action in U.S. Appl. No. 10/395,372, mailed Jun. 12, 2006.
Office Action in U.S. Appl. No. 10/395,372, mailed May 23, 2005.
Office Action in U.S. Appl. No. 10/395,372, mailed Nov. 23, 2005.
Office Action in U.S. Appl. No. 10/435,925, mailed Sep. 30, 2004.
Office Action in U.S. Appl. No. 11/121,316, mailed Apr. 16, 2009.
Office Action in U.S. Appl. No. 11/121,316, mailed Jul. 21, 2008.
Office Action in U.S. Appl. No. 11/121,316, mailed Mar. 17, 2008.
Office Action in U.S. Appl. No. 11/672,449, mailed Jun. 13, 2008.
Office Action in U.S. Appl. No. 11/672,449, mailed Mar. 20, 2009.
Office Action in U.S. Appl. No. 11/927,418, mailed Mar. 2, 2009.
Office Action in U.S. Appl. No. 11/941,820, mailed Apr. 21, 2009.
Osburn et al. "Genetic of Pharmacologic Amplification of Nrf2 Signaling Inhibits Acute Inflammatory Liver Injury in Mice" Toxicological Sciences 2008 104:218-227.
Patel et al. "Phase II Clinical Investigation of Gemcitabine in Advanced Soft Tissue Sarcomas and Window Evaluation of Dose Rate on Gemcitabine Triphosphate Accumulation" Journal Clinical Oncology 2001 19(15):3483-3489.
PCT, International Preliminary Examination Report, in Int. App. No. PCT/US1999/13635 mailed Sep. 6, 2000.
PCT, International Preliminary Examination Report, in Int. App. No. PCT/US2001/44541 mailed Jan. 15, 2004.
PCT, International Preliminary Examination Report, in Int. App. No. PCT/US2003/01307 mailed Oct. 20, 2003.
PCT, International Search Report and Written Opinion, in Int. App. No. PCT/US2008/073352 mailed Feb. 13, 2009.
PCT, International Search Report and Witten Opinion, in Int. App. No. PCT/US2007/085010 mailed Apr. 16, 2008.
PCT, International Search Report and Written Opinion, in Int. App. No. PCT/US2009/030771 mailed Apr. 9, 2009.
PCT, International Search Report and Written Opinion, in Int. App. No. PCT/US2007/071933 mailed Nov. 26, 2007.
PCT, International Search Report and Written Opinion, in Int. App. No. PCT/US2007/085010 mailed Apr. 16, 2008.
PCT, International Search Report, in Int. App. No. PCT/US1999/13635 mailed Oct. 20, 1999.
PCT, International Search Report, in Int. App. No. PCT/US2001/44541 mailed Jan. 24, 2003.
PCT, International Search Report, in Int. App. No. PCT/US2003/01307 mailed May 12, 2003.
PCT, Written Opinion, in Int. App. No. PCT/US1999/13635 mailed May 15, 2000.
PCT, Written Opinion, in Int. App. No. PCT/US2001/44541 mailed Sep. 23, 2003.
Petition Decision, issued in U.S. Appl. No. 10/345,053, mailed May 22, 2006.
Pollard, J. W. "Tumor-Educated Marcophages Promote Tumor Progression and Metastasis" Nature Reviews 2004 4:71-78.
Rangasamy et al. "Disruption of Nrf2 Enhances Susceptibility to Severe Airway Inflammation and Asthma in Mice" Journal of Experimental Medicine 2005 202:4759.
Response to Office Action, in Canadian Patent App. No. 2,335,505, dated Jul. 10, 2008.
Response to Office Action, in Canadian Patent App. No. 2,335,505, dated May 11, 2007.

(56) References Cited

OTHER PUBLICATIONS

Response to Office Action, in European Patent App. No. 01 989 130, dated Sep. 5, 2008.
Response to Office Action, in European Patent App. No. 99 928 731, dated Oct. 1, 2008.
Response to Office Action, in European Patent App. No. 99 928 731, dated Mar. 9, 2009.
Response to Office Action, in European Patent App. No. 99 928 731, dated Jun. 23, 2005.
Response to Office Action, in European Patent App. No. 99 928 731, dated Aug. 14, 2007.
Response to Office Action, in U.S. Appl. No. 09/335,003, dated Sep. 28, 2000.
Response to Office Action, in U.S. Appl. No. 09/335,003, dated Mar. 2, 2001.
Response to Office Action, in U.S. Appl. No. 09/335,003, dated Apr. 16, 2001.
Response to Office Action, in U.S. Appl. No. 09/927,081, dated Jun. 24, 2002.
Response to Office Action, in U.S. Appl. No. 09/998,009, dated Apr. 21, 2004.
Response to Office Action, in U.S. Appl. No. 09/998,009, dated Sep. 14, 2004.
Response to Office Action, in U.S. Appl. No. 09/998,009, dated Apr. 19, 2005.
Response to Office Action, in U.S. Appl. No. 09/998,009, dated Oct. 11, 2005.
Response to Office Action, in U.S. Appl. No. 09/998,009, dated Mar. 30, 2006.
Response to Office Action, in U.S. Appl. No. 09/998,009, dated Jan. 3, 2007.
Response to Office Action, in U.S. Appl. No. 09/998,009, dated Sep. 4, 2007.
Response to Office Action, in U.S. Appl. No. 09/998,009, dated Feb. 18, 2008.
Response to Office Action, in U.S. Appl. No. 10/345,053, dated Sep. 24, 2004.
Response to Office Action, in U.S. Appl. No. 10/345,053, dated Mar. 23, 2005.
Response to Office Action, in U.S. Appl. No. 10/345,053, dated Sep. 3, 2005.
Response to Office Action, in U.S. Appl. No. 10/345,053, dated Feb. 6, 2006.
Response to Office Action, in U.S. Appl. No. 10/395,372, dated Apr. 28, 2004.
Response to Office Action, in U.S. Appl. No. 10/395,372, dated Nov. 9, 2004.
Response to Office Action, in U.S. Appl. No. 10/395,372, dated Jul. 25, 2005.
Response to Office Action, in U.S. Appl. No. 10/395,372, dated Nov. 23, 2005.
Response to Office Action, in U.S. Appl. No. 10/395,372, dated Apr. 21, 2006.
Response to Office Action, in U.S. Appl. No. 10/395,372, dated Oct. 12, 2006.
Response to Office Action, in U.S. Appl. No. 10/395,372, dated Jan. 12, 2007.
Response to Office Action, in U.S. Appl. No. 10/395,372, dated Feb. 14, 2007.
Response to Office Action, in U.S. Appl. No. 10/435,925, dated Mar. 30, 2005.
Response to Office Action, in U.S. Appl. No. 11/121,316, dated Apr. 4, 2008.
Response to Office Action, in U.S. Appl. No. 11/121,316, dated Dec. 19, 2008.
Response to Office Action, in U.S. Appl. No. 11/672,449, dated Dec. 15, 2008.
Response to Office Action, in U.S. Appl. No. 11/927,418, dated Apr. 2, 2009.
Response to Written Opinion, in Int. App. No. PCT/US1999/13635, dated Jul. 14, 2000.
Richardson et al. "Synthesis and Restriction Enzyme Analysis of Oligodeoxyribonucleotides Containing the Anti-Cancer Drug 2',2'-diofluoro-2'-deoxycytidine" Nucleic Acid Research 1992 20(7):1763-1769.
Rizzieri et al. "Phase I Evaluation of Prolonged-Infusion Gemcitabine with Mitoxantrone for Relapsed or Refractory Acute Leukemia" Journal of Clinical Oncology 2002 20(3):674-679.
Robbins et al. "Inflammation and Repair" Basic Pathology $3^{rd}$ Edition, W.B. Sanders Company, Chapter 2, p. 28, 1981.
Singh, S. and Evans, T. W. "Nitric Oxide, the Biological Mediator of the Decade: Fact or Fiction?" European Respiratory Journal 1997 10:699-707.
Stedman's Medical Journal $23^{rd}$ Edition, The Williams & Wilkins Company, p. 401, 1976.
Strejan et al. "Suppression of Chronic-Relapsing Experimental Allergic Encephalomyelitis in Strain-13 Guinea Pigs by Administration of Liposome-Associated Myelin Basic Protein" Journal of Neuroimmunology 1984 7(1):27.
Suh et al. "New Triterpenoids as Cancer Preventive and Anti-inflammatory Agents" Proceedings of the American Association for Cancer Research 1997 38:216, Abstract No. 1457.
Supplementary European Search Report, issued in European Patent App. No. 01 989 130, mailed Aug. 9, 2007.
Supplementary European Search Report, issued in European Patent App. No. 03 729 681, mailed Aug. 3, 2006.
Sussan et al. "Disruption of Nrf2, a Key Inducer of Antioxidant Defenses, Attenuates ApoE-Mediated Atherosclerosis in Mice" PLoS One 2008 3(11):1-9.
Tempero et al. "Randomized Phase II Comparison of Dose-Intense Gemcitabine: Thirty-Minute Infusion and Fixed Dose Rate Infusion in Patients with Pancreatic Adenocarcinoma" Journal of Clinical Oncology 2003 21(18):3402-3408.
Therasse et al. "New Guidelines to Evaluate the Response to Treatment in Solid Tumors. European Organization for Research and Treatment of Cancer, National Cancer Institute of the United States, National Cancer Institute of Canada" Journal of the National Cancer Institute 2000 92(3):205.
Thimmulappa et al. "Nrf2 is a Critical Regulator of the Innate Immune Response and Survival During Experimental Sepsis" Journal of Clinical Investigation 2006 116(4):984-995.
Thimmulappa et al. "Nrf2-Dependent Protection from LPS Induced Inflammatory Response and Mortality by CDDO-Imidazolide" Biochemical and Biophysical Research Communications 2006 351:883-889.
Thimmulappa et al. "Preclinical Evaluation of Targeting the Nrf2 Pathway by Triterpenoids (CDDO-Im and CDDO-Me) for Protection from LPS-Induced Inflammatory Response and Reactive Oxygen Species in Human Peripheral Blood Mononuclear Cells and Neutrophils" Antioxidants & Redox Signaling 2007 9:1-8.
Torres et al. "Inflammation and Nitric Oxide Production in Skeletal Muscle of Type 2 Diabetic Patients" Journal of Endocrinology 2004 181:419-427.
Tran et al. "The Synthetic Triterpenoid CDDO-Methyl Ester Modulates Microglial Activities Inhibits TNF Production, and Provides Dopaminergic Neuroprotection" Journal of Neuroinflammation 2008 5:1-14.
U.S. Appl. No. 12/352,473, filed Jan. 12, 2009.
U.S. Appl. No. 12/426,737, filed Apr. 20, 2009.
U.S. Appl. No. 12/426,778, filed Apr. 20, 2009.
U.S. Appl.. No. 12/426,791, filed Apr. 20, 2009.
U.S. Appl. No. 12/426,832, filed Apr. 20, 2009.
U.S. Appl. No. 12/426,889, filed Apr. 20, 2009.
U.S Appl. No. 60/955,939, filed Aug. 15, 2007.
Van Muiswinkel, F. L. and Kuiperij, H. B. "The Nrf2-ARE Signaling Pathway: Promising Drug Target to Combat Oxidative Stress in Neurodegenerative Disorders" Current Drug Target—CNS & Neurological Disorders 2005 4:267-281.
Veerman et al. "Antitumor Activity of Prolonged as Compared with Bolus Administration of 2',2'-difluorodeoxycytidine in vivo Against Murine Colon Tumors" Cancer Chemotherapy and Pharmacology 1996 38(4):335-342.

(56) References Cited

OTHER PUBLICATIONS

Vodovotz et al. "Inducible Nitric Oxide Synthase in Tangle-Bearing Neurons of Patients with Alzheimer's Disease" The Journal of Experimental Medicine 1996 184:1425-1433.

Yore et al. "The Synthetic Triterpenoid 1-[2-cyano-3,12-dioxooleana-1,9(11)-dien-28-oyl] imidazole Blocks Nuclear Factor-kappaB Activation through Direct Inhibition of IkappaB Kinase Beta" Molecular Cancer Therapy 2006 5(12):3232-3239.

Yu, X. and Kensler, T. "Nrf2 as a Target for Cancer Chemoprevention" Mutation Research 2005 591(1-2):93-102.

Zhou et al. "Physical Stability of Amorphous Pharmaceuticals: Importance of Configurational Thermodynamic Quantities and Molecular Mobility" Journal of Pharmaceutical Sciences 2002 91(8):1863-1872.

Office Communication dated Dec. 23, 2009 from U.S. Appl. No. 11/941,723, filed Nov. 16, 2007.

Ji et al. "The Synthetic Triterpenoid CDDO-Imidazolide Induces Monocytic Differentiation by Activating the Smad and ERK Signaling Pathways in HL60 Leukemia Cells" Molecular Cancer Therapeutics 2006 5:1452-1458.

Leach, J. K. and Mooney, D. J. "Bone Engineering by Controlled Delivery of Osteoinductive Molecules and Cells" Expert Opinion on Biological Therapy 2004 4(7):1015-1027.

Sun, S. "Bone Disease Drug Discovery: Examining the Interactions Between Osteoblast and Osteoclast" Expert Opinion on Therapeutic Targets 2008 12(2):239-251.

Begum et al. "Synthesis of 2β-Hydroxyursolic Acid and Other Ursane Analogs from Ursonic Acid" Australian Journal of Chemistry 1993 46(7):1067-1071.

Bowden et al. "Constituents of the Fruit of *Pseudopanax arboreum* (Araliaceae)" Australian Journal of Chemistry 1975 28(1):91-107.

Campbell et al. "Endocyclic α,β-unsaturated Ketones. VI. Ultraviolet and Infrared Absorption Spectra and Resonance Stabilization" Bioorganic and Medicinal Chemistry Letters 1997 7(13):1623-1628.

Chattopadhyay et al. "Studies on Autoxidation: Part IV. Synthesis of Isometric 2,3-diols of olean-12-en-28-oate and Isohopane (moretane)" Indian Journal of Chemistry, Section B: Organic Chemistry Including Medicinal Chemistry 1977 15(1):21-24.

Devi et al. "Constituents of Black Dammar Resin and Some Transformation Products of α- and β-amyrins" Indian Journal of Chemistry 1969 7(12):1279-1280.

Elgamal et al. "Glycyrrhetic Acid Derivatives with Modified Ring A" Journal of Pharmaceutical Sciences 1973 62(9):1557-1558.

Elgamal et al. "The C-2,C-3-glycol Derivatives of Gylcyrrhetic Acid" Tetrahedron 1974 30(23/24):4083-4087.

Endová et al. "Preparation of 2,3-secodiacids of the Lupane Series" Collection of Czechoslovak Chemical Communications 1994 59(6):1420-1429.

Evers et al. "Betulinic Acid Derivatives: A New Class of Human Immunodeficiency Virus Type I Specific Inhibitors with a New Mode of Action" Journal of Medicinal Chemistry 1996 39(5):1056-1068.

Ganguly et al. "Oxidation of Ring in a Lupeol" Tetrahedron 1966 22(10):3597-3599.

Garcia-Granados et al. "Semi-Synthesis of Triterpene A-Ring Derivatives from Oleanolic and Maslinic Acids. Theoretical and Experimental $^{13}$C Chemical Shifts" Journal of Chemical Research, Synopses, 2000 2:56-57.

Garcia-Granados et al. "Semi-Synthesis of Triterpene A-ring Derivatives from Oleanolic and Maslinic Acids. Part II. Theoretical and Experimental $^{13}$C Chemical Shifts" Journal of Chemical Research, Synopses, 2000 5:211-212.

Glen et al. "Isolation of a New Triterpenoid from Rose-bay Willowherb" Chemistry and Industry, London, United Kingdom 1965 46:1908.

Govidachari et al. "Gymnosporol, A New Pentacyclic Triterpene from *Gymnosporia rothiana*" Indian Journal of Chemistry 1970 8(5):395-397.

Green, G. F. H. and Long, A. G. "Compounds Related to the Steroid Hormones. Part II. The Action of Hydrogen Bromide on 2-bromo-3-oxo-$\Delta^1$-5α-steroids" Journal of the Chemical Society 1961 2532-2543.

Hanna, G. and Ourisson, R. "Studies of Cyclic Ketones. VIII. Preparation and Properties of Polycyclic α-diketones" Bulletin de la Societe Chemique de France 1961 1945-1951.

Hattori et al. "A Triterpene from the Fruits of *Rubus chingii*" Phytochemistry 1988 27(12):3975-3976.

Huneck, S. "Triterpene, XIV: Die Bromierung Von 19β28-epoxy-3-oxo-2-diazo-und-1-oxo-2-diazo-Sowie von 19β28-epoxy-1-oxo-18αH-oleanan" Chemische Berichte 1965 98(9):2873-2843.

Khan et al. "α-amyrin Derivatives from *Corchorus depresses*" Phytochemistry 1991 30(6):1989-1992.

Klinot, J. and Vystrcil, A. "Triterpenes. VIL. Stereochemistry of 2-bromo Derivatives of Allobetuline and Alloheterobetaline" Collection of Czechoslovak Chemical Communications 1966 31(3):1079-1092.

Klinot et al. "Triterpenes. Part LXXXVI. Triterpenoid 2,3-ketols, diols and their Acetates: Preparation and Conformation of the Ring A" Collection of Czechoslovak Chemical Communications 1989 54(2):400-412.

Kumar, N. and Seshadri, T. R. "Triterpenoids of *Pterocarpus santalinus*: Constitution of a New Lupene Diol" Phytochemistry 1975 14(2):521-523.

Kundu et al. "Synthese von 2α-methoxycarbonyl-A-nor-lupa" Chemische Beerichte 1968 101(9):3255-3264.

Lavie, D. and Shvo, Y. "Constituents of Ecballium Elaterium: Proposed Structure for Elatericin A and B" Chemistry and Industry 1959 429-430.

Lawrie et al. "Isolation of Derivatives of Ursolic Acid from Apple Skin" Chemistry and Industry 1966 41:1720.

Lehn, J. M. and Ourisson, G. "Syntheses in the Lupane Series" Bulletin de la Societe Chimque de France 1962 1133-1136.

Lehn, J. M. and Vystreil, A. "Resonance Magnetique Nucleaire de Produits Naturels—VI: Triterpénes Dérivés de la Bétuline" Tetrahedron 1963 19(11):1733-1745.

Lehn, J. M. and Ourisson, G. "Nuclear Magnetic Response (N.M.R.) of Natural Products. I. General Introduction. Triterpenes of the Lupane Series. Methyl Groups" Bulletin de la Societe Chimique de France 1962 1137-1142.

Li et al. "Studies on Constituents of Rosa Multiflora Thunb" Zhongguo Yaoke Daxue Xuebao 2002 33(3):184-187.

Lugemwa et al. "A Heliothis Zea Antifeedant from the Abundant Birchbark Triterpene Betulin" Journal of Agricultural and Food Chemistry 1990 38(2):493-496.

Mane, R. A. and Ingle, D. B. "Synthesis and Biological Activity of Some New 1,5-benzothiazepines Containing Thiazole Moiety: 2-aryl-4-(4-methyl-2-substituted-aminothiazol-5-yl)-2,3-dihydro-1, 5-benzothiazepines" Indian Journal of Chemistry, Section B: Organic Chemistry Including Medicinal Chemistry 1982 21B(10):973-974.

Manzoor-i-Khuda, M. and Habermehl, G. "Chemical Constitutents of Corchorus Capsularis and C. Olitorium (Jute Plant). III. Structure of Corosin" Zietschrift fuer Naturforschung, Teil C: Biochemie, Biphysik, Biologie, Virologie 1974 29(5-6):209-221.

Manzoor-i-Khuda, M. "Isolation Techniques for Active Principles from Plants and their Composition and Structure Determination through Spectroscopic Techniques" New Trends Nat. Prod. 1986 26:303-323.

Misra et al. "Studies on Autoxidation: Part II—Synthesis of Isomeric 2,3-diols of Δ12-oleanen" Indian Journal of Chemistry, Section B: Organic Chemistry Including Medicinal Chemistry 1976 14B(6):411-414.

Osman et al. "Application of Chemical Reactions on Thin-Layer Chromatoplates. IV. Triterpene" Bulletin of the Chemical Society of Japan 1974 47(8):2056-2058.

Osman et al. "Chemical Studies on Pentacyclic Triterpenes. I. Benzilic Acid Rearrangement of Ring A in Ursolic Acid" Egyptian Journal of Chemistry 1972 15(3):269-272.

Picard et al. "Structure of the Triterpenes" J. Soc. Chem. Ind. 1939 58:58-59.

(56) References Cited

OTHER PUBLICATIONS

Pitzele, B. S. "Synthesis of 2-Oxygenated Glycyrrhetic Acid Derivatives" Journal of Medicinal Chemistry 1974 117(2):191-194.
Pradhan, B. P. and De, S. "Preparation of Triterpenoid Dioxpheenol via Oximinoketone and Structure of Baccatin" Indian Journal of Chemistry, Section B: Organic Chemistry including Medicinal Chemistry 1982 21B(9):823-828.
Pradhan, B. P. and Gosh, P. "Studies on Reactions of 2-bromo-3-ketotriterpenoids: Part IV. Debromination and Dehydrobromination of 2α-bromo and 2,2-dibromo Derivatives of Lupanone and Methyl Dihydrobetulonate" Indian Journal of Chemistry, Section B: Organic Chemistry including Medicinal Chemistry 1994 33B(1):73-75.
Sejbal et al. "Triterpenes. Part LXXIII. Reactions of Triterpenod Ketones with Sulfur and Morpholine under Willgerodt-Kindler Reaction Conditions" Collection of Czechoslovak Chemical Communications 1986 51(1):118-127.
Sejbal et al. "Triterpenes. Part XC. Conversion of Betulin into Careyagenolide (2α,3β-dihydroxy-18α, 19βH-ursan-28, 20β-olide" Collection of Czechoslovak Chemical Communications 1989 54(4):1036-1042.
Shimao, I. and Oae, S. "The Wallach Rearrangement of Some 4,4'-disubstituted Azoxybenzenes" Bulletin of the Chemical Society of Japan 1983 56(2):643-644.
Witz et al. "Cyclic Ketones. XIII. Circular Dichroism of Steroid and Triterpene Ketones. Conformation of Ring A of 8-methylated 3-oxotriterpenes" Bull Soc China, France 1963 1101-1112.
Office Communication dated Aug. 2, 2010 from U.S. Appl. No. 11/941,723, filed Nov. 16, 2007.
International Preliminary Report on Patentability issued in PCT/US2007/085006, dated Jul. 14, 2009.
International Search Report issued in PCT/US2007/085006, dated Aug. 7, 2009.
Niikura et al. "The Effects of Synthetic Triterpenoids on SZP Synthesis in Articular Chondrocytes" Osteoarthritis and Cartilage 2006 14:S112-S113.
Niikura et al. "The Effects Synthetic Triterpenoids on Superficial Zone Protein Synthesis in the Articular Chondrocytes" Abstract submitted 53rd meeting of the Orthopedic Research Society, San Diego 2007.
Vincenti et al. "The Synthetic Triterpenoid TP-222 Inhibits RANKL Induction of Differentiation and MMP-9 Gene Expression in Osteoclasts" Abstract Presented at 70th Annual Scientific Meeting of the American College of Rheumatology 41st Annual Scientific Meeting 2006.
Ito et al. "Repulsive Axon Guidance Molecule Sema3A Inhibits Branching Morphogenesis of Fetal Mouse Lung" Mechanisms of Development 2000 97:35-45.
Ito et al. "Structural Comparison of Three Types of Staphylococcal Cassette Chromosome *mec* Integrated in the Chromosome in Methicillin-Resistant *Staphylococcus aureus*" Antimicrobial Agents and Chemotherapy 2001 45(5):1323-1336.
Office Communication dated Dec. 24, 2013 from U.S. Appl. No. 13/466,473, filed May 8, 2012.
Office Communication dated Apr. 1, 2014 from U.S. Appl. No. 13/466,473, filed May 8, 2012.
Cannon, J.G., Chapter 19 in Burger's Medicinal Chemistry and Drug Discovery, Fifth Edition, vol. I: Principles and Practice, Wiley-Interscience 1995, pp. 783-802.
Office Communication dated Jul. 1, 2014 from U.S. Appl. No. 13/466,473, filed May 8, 2012.
Hartwig, J. F. "Carbon-Heteroatom Bonding-Forming Reductive Eliminations of Amines, Ethers, and Sulfides" Accounts of Chemical Research 1998 31(12):852-860.
Hartwig, J. F. "Transition Metal Catalyzed Synthesis of Arylamines and Aryl Ethers from Aryl Halides and Triflates: Scope and Mechanism" Angewandate Chemie International Edition 1998 37:2047-2067.
Hartwig, J. F. "Approaches to Catalyst Discovery. New Carbon-Heteroatom and Carbon-Carbon Bond Formation" Pure and Applied Chemistry 1999 71(8):1417-1423.
King et al. "Highly General Stereo-, Regio-, and Chemo-Selective Synthesis of Terminal and Internal Conjugated Enynes by the Pd-Catalysed Reaction of Alkynylzinc Reagents with Alkenyl Halides" Journal of the Chemical Society, Chemical Communications 1977 19:683-684.
Kosugi et al. "Reactions of Allyltin Compounds III. Allylation of Aromatic Halides with Allyltributyltin in the Presence of Tetrakis(Triphenylphosphine)Palladium(0)" Chemistry Letters 1977:301-302.
Milstein, D. and Stille, J. K. "A General, Selective, and Facile Method for Ketone Synthesis from Acid Chlorides and Organotin Compounds Catalyzed by Palladium" Journal of the American Chemical Society 1978 100(11):3636-3638.
Miyaura et al. "A New Stereospecific Cross-Coupling by the Palladium-Catalyzed Reaction of 1-Alkenylboranes with 1-Alkenyl or 1-Alkynyl Halides" Tetrahedron Letters 1979 36:3437-3440.
Miyaura, N. and Suzuki, A. "Palladium-Catalyzed Cross-Coupling Reactions of Organoboron Compounds" Chemical Reviews 1995 95(7):2457-2483.
Muci, A. R. and Buchwald, S. L. "Practical Palladium Catalysts for C—N and C—O Bond Formation" Topics in Current Chemistry 2002 219:133-209.
Porcheddu et al. "Microwave-Assisted Synthesis of Isonitriles: A General Simple Methodology" Journal of Organic Chemistry 2005 70:2361-2363.
Wolfe et al. "Rational Development of Practical Catalysts for Aromatic Carbon-Nitrogen Bond Formation" Accounts of Chemical Research 1998 31(12):805-818.
Yang, B. H. and Buchwald, S. L. "Palladium-Catalyzed Amination of Aryl Halides and Sulfonates" Journal of Organometallic Chemistry 1999 576:125-146.
Office Communication dated May 27, 2014 from U.S. Appl. No. 13/466,456, filed May 8, 2012.
PCT, International Preliminary Report on Patentability in Int. App. No. PCT/US2013/039902 issued Nov. 11, 2014.

\* cited by examiner

SYNTHETIC TRITERPENOIDS AND METHODS FOR MODULATING STEM/PROGENITOR CELL GENE EXPRESSION

INTRODUCTION

This application is the national stage under 35 U.S.C. §371 of PCT International Application No. PCT/US2013/039902, filed May 7, 2013, which claims the benefit of priority from U.S. patent application Ser. Nos. 13/466,456, filed May 8, 2012, and 61/644,080, filed May 8, 2012, the contents of which are incorporated herein by reference in their entireties.

BACKGROUND OF THE INVENTION

One of the major needs in cancer prevention is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the subject of many studies that have attempted to link these two processes in a mechanistic fashion (Sporn & Roberts (1986) *J. Clin. Invest.* 78:329-332; Ohshima & Bartsch (1994) *Mutat. Res.* 305:253-264). The enzymes that mediate the constitutive synthesis of nitric oxide and prostaglandins from arginine and arachidonate, respectively, have relative little significance for either inflammation or carcinogenesis. In contrast, inducible nitric oxide synthase (iNOS) and inducible cycloxygenase (COX-2) both have critical roles in the response of tissues to injury or infectious agents (Moncada, et al. (1991) *Pharmacol. Rev.* 43:109-142; Nathan & Xie (1994) *Cell* 78:915-918; Siebert & Masferrer (1994) *Receptor* 4(1):17-23; Tamir & Tannebaum (1996) *Biochim. Biophys. Acta* 1288:F31-F36). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, and rheumatoid arthritis.

Triterpenoids, biosynthesized in plants by the cyclization of squalene, are used for medicinal purposes in many Asian countries; and some, like ursolic and oleanolic acids, are known to exhibit anti-inflammatory and anti-carcinogenic activity (Huang, et al. (1994) *Cancer Res.* 54:701-708; Nishino, et al. (1988) *Cancer Res.* 48:5210-5215). However, the biological activity of these naturally-occurring molecules is relatively weak, and therefore the synthesis of new analogs to enhance their potency has been undertaken (Honda, et al. (1997) *Bioorg. Med. Chem. Lett.* 7:1623-1628; Honda, et al. (1998) *Bioorg. Med. Chem. Lett.* 8(19):2711-2714).

An ongoing effort for the improvement of anti-inflammatory and antiproliferative activity of oleanolic and ursolic acid analogs led to the discovery of 2-cyano-3,12-dioxooleane-1,9(11)-dien-28-oic acid (CDDO) and related compounds (Honda, et al. (1997) supra; Honda, et al. (1998) supra; Honda, et al. (1999) *Bioorg. Med. Chem. Lett.* 9(24):3429-3434; Honda, et al. (2000) *J. Med. Chem.* 43:4233-4246; Honda, et al. (2000) *J. Med. Chem.*, 43:1866-1877; Honda, et al. (2002) *Bioorg. Med. Chem. Lett.* 12:1027-1030; Suh, et al. (1998) *Cancer Res.* 58:717-723; Suh, et al. (1999) *Cancer Res.*, 59(2):336-341; Suh, et al. (2003) *Cancer Res.* 63:1371-1376; Place, et al. (2003) *Clin. Cancer Res.* 9:2798-2806; Liby, et al. (2005) *Cancer Res.* 65:4789-4798).

Furthermore, U.S. Pat. Nos. 6,326,507, 6,552,075, 7,288,568, 7,863,327, 8,034,955, US 2009/0060873, US 2009/0048204, WO 2008/136838 and WO 2009/023232 teach the use of 2-cyano-3,12-dioxooleana-1,9(11)-dien-28-oic acid (CDDO), and derivatives thereof such as 2-cyano-3,12-dioxoolean-1,9(11)-dien-28-oic acid methyl ester (CDDO-Me) and amide derivatives, for the treatment of diseases such as cancer, Alzheimer's disease, Parkinson's disease, inflammatory bowel diseases, and multiple sclerosis. Similarly, U.S. Pat. No. 6,974,801 and WO 2004/064723 teach the use of 2-cyano-3,12-dioxooleana-1,9(11)-dien-28-onitrile (CNDDO), 1-(2-cyano-3,12-dioxooleana-1,9(11)-dien-28-oyl) imidazole (CDDO-Im), 1-(2-cyano-3,12-dioxooleana-1,9(11)-dien-28-oyl)-2-methylimidazole, and 1-(2-cyano-3,12-dioxooleana-1,9(11)-dien-28-oyl)-4-methylimidazole in the prevention or treatment of cancer, Alzheimer's disease, Parkinson's disease, multiple sclerosis, rheumatoid arthritis, and other inflammatory diseases. Furthermore, the use of triterpenoids such as CDDO, CDDO-Me, CDDO-Im, and CDDO-Ethylamide in stimulating the growth and repair of bone and cartilage (US 2008/0233195 and WO 2008/064132) as well as in inhibiting HIV-1 replication (WO 2005/046732) has been described. US 2009/0326063 further teaches the use of synthetic triterpenoids in the prevention and treatment of renal/kidney disease, insulin resistance/diabetes, fatty liver disease, and/or endothelial dysfunction/cardiovascular disease.

Combination therapies of CDDO or CDDO-Me and a chemotherapeutic agent, immunosuppressive agent, or proteasome inhibitor are described in U.S. Pat. No. 7,435,755, U.S. Pat. No. 7,795,305, US 2009/0018146, US 2009/0048205, WO 2002/047611 and WO 2009/023845 for the treatment of cancer and graft versus host disease. Moreover, formulations for improved oral bioavailability of CDDO-Me are disclosed in WO 2010/093944.

Furthermore, CDDO-Me suppresses the induction of several important inflammatory mediators, such as iNOS, COX-2, TNFα, and IFNγ, in activated macrophages. CDDO-Me has also been reported to activate the Keap1/Nrf2/ARE signaling pathway resulting in the production of several anti-inflammatory and antioxidant proteins, such as heme oxygenase-1 (HO-1). These properties have made CDDO-Me a candidate for the treatment of neoplastic and proliferative diseases, such as cancer. Moreover, synthetic triterpenoids have been found to induce apoptosis and differentiation and inhibit proliferation in human leukemia cells (Ikeda, et al. (2003) *Cancer Res.* 63:5551-5558; Konopleva, et al. (2002) *Blood* 99(1):326-335; Suh, et al. (1999) supra; Ito, et al. (2000) *Mech. Dev.* 97:35-45), induce osteoblastic differentiation in osteosarcoma cells (Ito, et al. (2001) *Antimicrob. Agents Chemother.* 45:1323-1336), enhance neuronal growth factor-induced neuronal differentiation of rat PC12 pheochromocytoma cells, and induce adipogenic differentiation of fibroblasts into adipocytes (Suh, et al. (1999) supra). CDDO-Me has also been found an effective drug for improving kidney function in patients suffering for renal/kidney disease using CDDO-Me (U.S. Pat. No. 8,129,429).

Given the activity of CDDO and CDDO-Me, additional oleanolic acid derivatives have been developed for use in treating cancer, cardiovascular disease, neurodegenerative disease, renal/kidney disease, diabetes, arthritis and inflammatory conditions such as obesity, hypertension, atherosclerosis, coronary heart disease, stroke, peripheral vascular disease, hypertension, nephropathy, neuropathy, myonecrosis, ulcerative colitis, Crohn's disease, irritable bowel syndrome, retinopathy and metabolic syndrome. See U.S. Pat. NoS. 7,915,402, 7,943,778, US 2010/0048887, US 2010/0048892, US 2010/0048911, US 2011/0245206 and US 2011/0245233.

In view of the therapeutic activities of this class of triterpenoids, it would be advantageous to have compounds with improved activity.

SUMMARY OF THE INVENTION

The present invention encompasses new triterpenoid compounds and the specific finding that such triterpenoid compounds alter gene expression in cells. The present invention therefore provides compositions and methods for inducing cell differentiation, in a variety of important contexts and applications.

Among other things, this invention provides a triterpenoid compound of Formula I, II, VI, VII, VIII, IX, X, XI, XII, XIII, XIV, XV, or XVI, as defined herein and a pharmaceutical composition containing the same.

Furthermore, the present invention provides methods for producing a cell, such as a stem or progenitor cell, with induced gene expression by contacting a stem or progenitor cell with an effective amount of a synthetic triterpenoid to induce the expression of one or more of SOX9 (Sex determining region Y-box 9), COL2A1 (Type II Collagen (alpha1)), TGF-β1, TGF-β2, TGF-β3, BMP2, BMP4, BMPRII (Bone Morphogenic Protein Receptor II), SMAD (Small Mothers Against Decapentaplegic) 3, SMAD4, SMAD6, SMAD7, TIMP (Tissue Inhibitor of Metalloproteinase)-1 or TIMP-2 in the stem or progenitor cell, wherein the stem or progenitor cell is not a mesenchymal stem cell, periosteum cell or osteoprogenitor cell. In one embodiment, the stem or progenitor cell is multipotent.

A stem or progenitor cell produced by the method is also provided, as are methods of using such cells in the treatment of a degenerative disease, disorder, condition, or injury such as skin wounds or injury, muscle injury, Parkinson's disease, diabetes, nerve injury, amyotrophic lateral sclerosis, traumatic brain injury, cardiac injury or disease, baldness, myocardial infarction, muscular dystrophy, or liver disease or injury. In addition, treatment of a congenital disorder such as familial dysautonomia, a congenital heart defect, a dysganglionic disorder in the gastrointestinal tract, or a pigment cell disorder is also provided.

Methods for treating a degenerative disease or injury, a congenital disorder, or a chemoresistant cancer such as chemoresistant colon cancer or glioblastoma by administering to a patient an effective amount of a synthetic triterpenoid are also provided.

DETAILED DESCRIPTION OF THE INVENTION

Triterpenoids, including CDDO-Me derivatives, have now been developed and shown to induce the expression of SOX9, COL2A1, TGF-β1, TGF-β2, TGF-β3, BMP2, BMP4, BMPRII, SMAD3, SMAD4, SMAD6, SMAD7, TIMP-1 and/or TIMP-2 in stem cells. For example, the synthetic triterpenoids CDDO-Im and CDDO-EA induce the expression of each of the above-referenced genes in mesenchymal stem cells and induce chondrogenesis in newborn mouse calvaria. In this respect, the present invention provides synthetic triterpenoid compounds and methods of using to same to produce stem/progenitor cells with altered expression of one or more of SOX9, COL2A1, TGF-β1, TGF-β2, TGF-β3, BMP2, BMP4, BMPRII, SMAD3, SMAD4, SMAD6, SMAD7, TIMP-1 or TIMP-2, as compared to a control (e.g., a cell not contacted with the synthetic triterpenoid), and application of such cells in the prevention or treatment of disease, where the cells can contacted with the triterpenoid in situ, in vivo, ex vivo or in vitro. In some embodiments, expression of one or more of said genes is indicative of differentiation of the stem/progenitor cell.

Compounds particularly embraced by this invention have the structure of Formula I, which includes hydrates, isomers, prodrugs or pharmaceutically acceptable salts of Formula I:

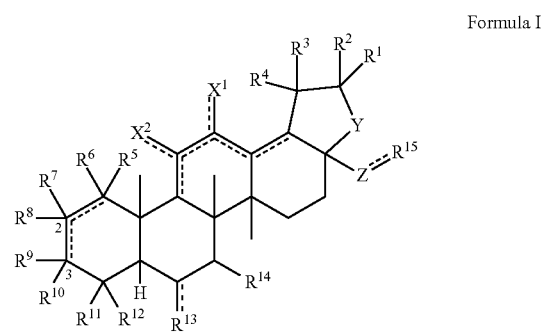

Formula I wherein,
at least one of $X^1$ and $X^2$ is $OR^a$, $NR^aR^b$, or $SR^a$, and the other of $X^1$ and $X^2$ is hydrogen, $OR^a$, $NR^aR^b$, or $SR^a$ wherein
  $R^a$ is a hydrogen, cyano, —$CF_3$, nitro, amino, or substituted or unsubstituted heteroaryl group;
  $R^b$ is hydrogen, hydroxyl, alkyl, aryl, aralkyl, acyl, alkoxy, aryloxy, acyloxy, alkylamino, arylamino, amido, or a substituted version of any of these groups; or a substituent convertible in vivo to hydrogen;
  provided that $R^a$ is absent when the atom to which it is bound is part of a double bond, further provided that when $R^a$ is absent the atom to which it is bound is part of a double bond;
Y is $CH_2$ or $CH_2$—$CH_2$;
Z is a covalent bond, —C(=O)—, alkanediyl, alkenediyl, alkynediyl, or a substituted version of any of these groups;
the dashed bonds can be independently present or absent;
$R^1$, $R^2$, $R^3$ and $R^4$ are each independently a hydrogen, hydroxyl, alkyl, substituted alkyl, alkoxy or substituted alkoxy group;
at least one of $R^5$, $R^6$, $R^7$, $R^8$, $R^9$ or $R^{10}$ is independently —OMs, —$CH_2$OMs, —C(=O)C=$CR^a$, —C≡$CCO_2R^a$, —$CCSO_2R^a$, —C≡CC(=O)$R^a$ or —$SO_2R^a$, or
$R^5$ and $R^6$, or $R^7$ and $R^8$, or $R^9$ and $R^{10}$ are together or =$CR^cR^d$, wherein
  $R^c$ is hydrogen or alkylthiyl, and
  $R^d$ is hydrogen, halo, alkylthiyl, or substituted or unsubstituted alkylsulfonyl or alkylsulfonyl-O—;
the remainder of $R^5$, $R^6$, $R^7$, $R^8$, $R^9$ and $R^{10}$ are independently hydrogen, hydroxyl, halo, cyano, =O, —C≡$CR^a$, —$CO_2R^a$, alkyl, alkenyl, alkynyl, aryl, aralkyl, heteroaryl, heteroaralkyl, acyl, alkoxy, aryloxy, acyloxy, alkylamino, arylamino, nitro, amino, amido, —C(O)$R^e$ or a substituted version of any of these groups, wherein
  $R^e$ is hydrogen, hydroxy, halo, amino, hydroxyamino, azido or mercapto; or $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$- alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-dialkylamino, $C_1$-$C_{15}$-alkoxyamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-alkylsulfonylamino, $C_1$-$C_{15}$-amido, $C_1$-$C_{15}$-alkylsilyloxy, or substituted versions of any of these groups;

$R^{11}$ and $R^{12}$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or $R^{11}$ and $R^{12}$ are taken together and are alkanediyl, alkenediyl, arenediyl, alkoxydiyl, alkenyloxydiyl, alkylaminodiyl, alkenylaminodiyl, or alkenylaminooxydiyl;

$R^{13}$ is hydrogen, hydroxy or oxo;

$R^{14}$ is hydrogen or hydroxyl; and $R^{15}$ is a hydrogen, hydroxyl, —NR$^f$R$^g$, cyano, halo, azido, phosphate, 1,3-dioxoisoindolin-2-yl, mercapto, silyl or —COOH group, substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl $C_2$-$C_{15}$-heteroaralkyl, $C_1$-$C_{15}$-acyl, $C_1$-$C_{15}$-alkoxy, $C_2$-$C_{16}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_1$-$C_{15}$-alkylthio, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_1$-$C_{12}$-alkylsulfinyl, $C_2$-$C_{12}$-alkenylsulfinyl, $C_2$-$C_{12}$-alkynylsulfinyl, $C_6$-$C_{12}$-aryl sulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups, a —CO$_2$Me, carbonyl imidazole, —CO—D-Glu(OAc)$_4$, —CONH$_2$, —CONHNH$_2$, —CONHCH$_2$CF$_3$, or —C(=O)-heteroaryl group, or Z and $R^{15}$ form a three to seven-membered ring, such that Z and $R^{15}$ are further connected to one another through one or more of —O— and alkanediyl, further wherein Z is —CH— and $R^{15}$ is —CH$_2$— or Z, $R^{15}$, and carbon numbers 13, 17 and 18 form a ring such that $R^{15}$ is bound to carbon 13, wherein Y is methanediyl or substituted methanediyl and $R^{15}$ is —O—, wherein $R^f$ and $R^g$ are independently hydrogen, hydroxyl, alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkoxy, thioacyl, alkylsulfonyl, alkenylsulfonyl, alkynylsulfonyl, arylsulfonyl, aralkylsulfonyl, heteroarylsulfonyl, or heteroaralkylsulfonyl, or a substituted version of any of these groups.

In certain embodiments, the bond between $C_2$ and $C_3$ in the A-ring is a double bond. In other embodiments, the bond between $C_2$ and $C_3$ in the A-ring is a single bond.

In some embodiments, the compound of the invention is a dimer as represented by the Formula II,

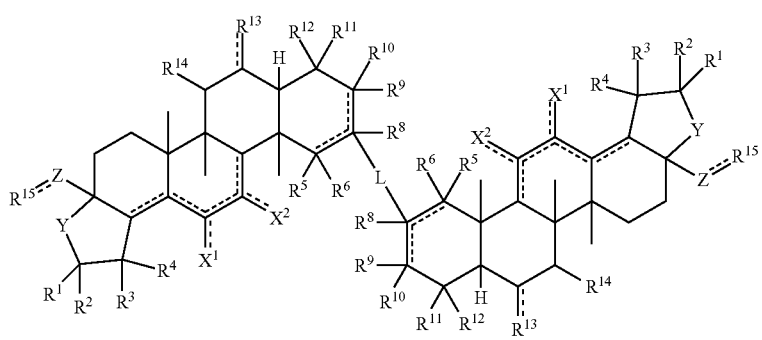

Formula II wherein $X^1$, $X^2$, Y, Z, $R^1$, $R^2$, $R^3$, $R^4$, $R^8$, $R^9$, $R^{11}$, $R^{12}$, $R^{13}$, $R^{14}$ and $R^{15}$ are as defined for Formula I and L is —C≡C—R—C≡C—, —C(=O)—, —C≡C—, —C≡C—N(—R)—, —C(=O)—N(—R)—, —C≡C—C(=O)—, —Ar—C(=O)—, or —C≡C—C(=O)—Ar—, wherein R is hydrogen, or an alkyl, aryl, alkenyl, or alkynyl group. Exemplary dimers include compounds 10-17.

In yet other embodiments, the compound of the invention has the structure as set forth in Formulae VI-XVI. In particular embodiments, the triterpenoid compound of the invention is a compound selected from compound 18-75.

As used herein, "hydrogen" means —H; "hydroxyl" means —OH; "oxo" means =O; "halo" or "halogen" means independently —F, —Cl, —Br or —I; "hydroxyamino" means —NHOH; "nitro" means —NO$_2$; "cyano" means —CN; "azido" means —N$_3$; "mercapto" means —SH; "thio" means =S; "sulfonyl" means —S(O)$_2$— (see additional definitions of groups containing the term sulfonyl, e.g., alkylsulfonyl); and "silyl" means —SiH$_3$ (see additional definitions of group(s) containing the term silyl, e.g., alkylsilyl).

For the groups below, the following parenthetical subscripts further define the groups as follows: "(Cn)" defines the exact number (n) of carbon atoms in the group. For example, "$C_1$-$C_{15}$-alkoxy" designates those alkoxy groups having from 1 to 15 carbon atoms (e.g., 1, 2, 3, 4, 5, 6, 7, 8, 9, 10, etc. or any range derivable therein (e.g., 3-10 carbon atoms)).

The term "alkyl" refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH₃, —CH₂CH₃, —CH₂CH₂CH₃, —CH(CH₃)₂, —CH(CH₂)₂, —CH₂CH₂CH₂CH₃, —CH(CH₃) CH₂CH₃, —CH₂CH (CH₃)₂, —C(CH₃)₃, —CH₂C (CH₃)₃, cyclobutyl, cyclopentyl, cyclohexyl, and cyclohexylmethyl are non-limiting examples of alkyl groups.

The term "alkanediyl" refers to a non-aromatic divalent group, wherein the alkanediyl group is attached with two σ-bonds, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH₂-(methylene), —CH₂CH₂—, —CH₂C(CH₃)₂CH₂—, and —CH₂CH₂CH₂— are non-limiting examples of alkanediyl groups.

The term "alkenyl" refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH₂, —CH=CHCH₃, —CH=CHCH₂CH₃, —CH₂CH=CH₂, —CH₂CH=CHCH₃, and —CH=CH—O₅H₅.

The term "alkenediyl" refers to a nonaromatic divalent group, wherein the alkenediyl group is attached with two σ-bonds, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, and —CH=CHCH₂— are non-limiting examples of alkynediyl groups.

The term "alkynyl" refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —CCCH₃, —C≡C₆H₅ and —CH₂C≡CCH₃, are non-limiting examples of alkynyl groups.

The term "alkynediyl" refers to a nonaromatic divalent group, wherein the alkynediyl group is attached with two σ-bonds, with two carbon atoms as points of attachment, a linear or branched, cyclo, cyclic or acyclic structure, at least one carbon-carbon triple bond, and no atoms other than carbon and hydrogen. The groups, —C≡C—, —C≡CCH₂—, and —C≡CCH(CH₃)— are non-limiting examples of alkynediyl groups.

The term "aryl" refers to a monovalent group with an aromatic carbon atom as the point of attachment, said carbon atom forming part of a six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, -ethylphenyl, propylphenyl, —C₆H₄CH(CH₃)₂, —C₆H₄CH(CH₂)₂, methylethylphenyl, vinylphenyl, naphthyl, and the monovalent group derived from biphenyl.

The term "arenediyl" refers to a divalent group, wherein the arenediyl group is attached with two σ-bonds, with two aromatic carbon atoms as points of attachment, said carbon atoms forming part of one or more six-membered aromatic ring structure(s) wherein the ring atoms are all carbon, and wherein the monovalent group is composed of carbon and hydrogen. Non-limiting examples of arenediyl groups include:

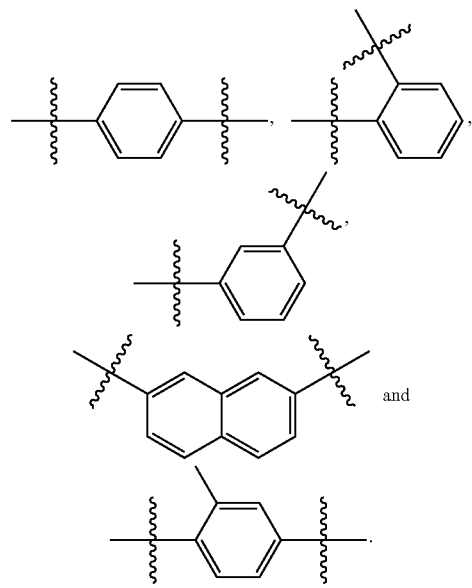

The term "aralkyl" refers to the monovalent group -alkanediyl-aryl, in which the terms alkanediyl and aryl are each used in a manner consistent with the definitions provided above. Non-limiting examples of aralkyls include 1-phenyl-ethyl, 2-phenyl-ethyl, indenyl and 2,3-dihydro-indenyl, provided that indenyl and 2,3-dihydro-indenyl are only examples of aralkyl in so far as the point of attachment in each case is one of the saturated carbon atoms.

The term "heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms).

The term "heteroaralkyl" refers to the monovalent group -alkanediyl-heteroaryl, in which the terms alkanediyl and heteroaryl are each used in a manner consistent with the definitions provided above. Non-limiting examples of aralkyls include pyridylmethyl, and thienylmethyl.

The term "acyl" refers to a monovalent group with a carbon atom of a carbonyl group as the point of attachment, further having a linear or branched, cyclo, cyclic or acyclic structure. The groups, —CHO, —C(=O)CH₃, —C(=O)CH₂CH₃, —C(=O)CH₂CH₂CH₃, —C(=O)CH(CH₃)₂, —C(=O)CH (CH₂)₂, —C(=O)C₆H₅, —C (=O)C₆H₄CH₃, and —C(=O)C₆H₄CH₂CH₃ are non-limiting examples of acyl groups.

The term "acyl" therefore encompasses, but is not limited to groups sometimes referred to as "alkyl carbonyl" and "aryl carbonyl" groups.

The term "alkoxy" refers to the group —OR, in which R is an alkyl, as that term is defined herein. Non-limiting examples of alkoxy groups include —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl.

Similarly, the terms "alkenyloxy," "alkynyloxy," "aryloxy," "aralkoxy," "heteroaryloxy," "heteroaralkoxy" and "acyloxy," refer to groups, defined as —OR, in which R is alkenyl, alkynyl, aryl, aralkyl, heteroaryl, heteroaralkyl and acyl, respectively, as those terms are defined above.

The term "alkoxydiyl" refers to a non-aromatic divalent group, wherein the alkoxydiyl group is attached with two σ-bonds, with (a) two saturated carbon atoms as points of attachment, (b) one saturated carbon atom and one oxygen atom as points of attachment, or (c) two oxygen atoms as points of attachment, further having a linear or branched, cyclo, cyclic or acyclic structure, no carbon-carbon double or triple bonds in the group's backbone, further having no backbone atoms other than carbon or oxygen and having at least one of each of these atoms in the group's backbone. The groups, —O—CH$_2$CH$_2$—, —CH$_2$—O—CH$_2$CH$_2$—, —O—CH$_2$CH$_2$—O— and —O—CH$_2$—O— are non-limiting examples of alkoxydiyl groups.

The term "alkenyloxydiyl" refers to a divalent group that is nonaromatic prior to attachment, wherein the alkenyloxydiyl group is attached with two v-bonds, which may become aromatic upon attachment, with (a) two carbon atoms as points of attachment, (b) one carbon atom and one oxygen atom as points of attachment, or (c) two oxygen atoms as points of attachment, further having a linear or branched, cyclo, cyclic or acyclic structure, at least one carbon-carbon double bond that is non-aromatic at least prior to attachment, further having no backbone atoms other than carbon or oxygen and having at least one of each of these atoms in the group's backbone. The groups, —O—CH=CH—, —O—CH=CHO— and —O—CH=CHCH$_2$— are non-limiting examples of alkenyloxydiyl groups.

The term "amino" refers to a moiety of the formula —NRR', wherein R and R' are independently hydrogen, alkyl, cycloalkyl, heterocycloalkyl, aryl or heteroaryl.

The term "alkylamino" refers to the group —NHR, in which R is an alkyl, as that term is defined above. Non-limiting examples of alkylamino groups include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, NH-cyclopentyl, and —NH-cyclohexyl.

Similarly, the terms "alkoxyamino," "alkenylamino," "alkynylamino," "arylamino," "aralkylamino," "heteroarylamino," "heteroaralkylamino," and "alkylsulfonylamino" refer to groups, defined as —NHR, in which R is alkoxy, alkenyl, alkynyl, aryl, aralkyl, heteroaryl, heteroaralkyl and alkylsulfonyl, respectively, as those terms are defined above. A non-limiting example of an arylamino group is —NHC$_6$H$_5$.

The term "dialkylamino" refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include —NHC(CH$_3$)$_3$, —N(CH$_3$)CH$_2$CH$_3$, —N (CH$_2$CH$_3$)$_2$, N-pyrrolidinyl, and N-piperidinyl.

The term "alkylaminodiyl" refers to a non-aromatic divalent group, wherein the alkylaminodiyl group is attached with two σ-bonds, with (a) two saturated carbon atoms as points of attachment, (b) one saturated carbon atom and one nitrogen atom as points of attachment, or (c) two nitrogen atoms as points of attachment, further having a linear or branched, cyclo, cyclic or acyclic structure, no double or triple bonds in the group's backbone, further having no backbone atoms other than carbon or nitrogen and having at least one of each of these atoms in the group's backbone. The groups, —NH—CH$_2$CH$_2$—, —CH$_2$—NH—CH$_2$CH$_2$—, —NH—CH$_2$CH$_2$—NH— and —NH—CH$_2$—NH— are non-limiting examples of alkylaminodiyl groups.

The term "alkenylaminodiyl" refers to a divalent group that is nonaromatic prior to attachment, wherein the alkenylaminodiyl group is attached with two σ-bonds, which may become aromatic upon attachment, with (a) two carbon atoms as points of attachment, (b) one carbon atom and one nitrogen atom as points of attachment, or (c) two nitrogen atoms as points of attachment, further having a linear or branched, cyclo, cyclic or acyclic structure, at least one carbon-carbon double bond or carbon-nitrogen double that is non-aromatic at least prior to attachment, further having no backbone atoms other than carbon or nitrogen. The groups —NH—CH=CH—, —NH—CH=N— and —NH—CH=CH—NH— are non-limiting examples of alkenylaminodiyl groups.

The term "alkenylaminooxydiyl" refers to a divalent group, wherein the alkenylaminooxydiyl group is attached with two σ-bonds, which may become aromatic upon attachment, with two atoms selected from the group consisting of carbon, oxygen and nitrogen as points of attachment, further having a linear or branched, cyclo, cyclic or acyclic structure, at least one carbon-carbon double bond, carbon-nitrogen double, or nitrogen-nitrogen double bond that is non-aromatic at least prior to attachment, further having no backbone atoms other than carbon nitrogen or oxygen and having at least one of each of these three atoms in the backbone. The group —O—CH=N—, is a non-limiting example of an alkenylaminooxydiyl group.

The term "amido" (acylamino) refers to the group —NHR, in which R is acyl, as that term is defined herein. A non-limiting example of an acylamino group is 13 NHC(=O)CH$_3$.

The term "alkylthio" refers to the group —SR, in which R is an alkyl, as that term is defined above. Non-limiting examples of alkylthio groups include —SCH$_3$, —SCH$_2$CH$_3$, —SCH$_2$CH$_2$CH$_3$, —SCH(CH$_3$)$_2$, —SCH(CH$_2$)$_2$, —S-cyclopentyl, and —S-cyclohexyl.

Similarly, the terms "alkenylthio," "alkynylthio," "arylthio," "aralkylthio," "heteroarylthio," "heteroaralkylthio" and "acylthio" refer to groups, defined as —SR, in which R is alkenyl, alkynyl, aryl, aralkyl, heteroaryl, heteroaralkyl and acyl, respectively, as those terms are defined above.

The term "thioacyl" refers to a monovalent group with a carbon atom of a thiocarbonyl group as the point of attachment, further having a linear or branched, cyclo, cyclic or acyclic structure. The groups —CHS, —C(=S)CH$_3$, —C(=S)CH$_2$CH$_3$, —C(=S)CH$_2$CH$_2$CH$_3$, —C(=S)CH(CH$_3$)$_2$, —C(=S)CH(CH$_2$)$_2$, —C(=S)C$_6$H$_5$, —C(=S)C$_6$H$_4$CH$_3$, —C(=S)C$_6$H$_4$CH$_2$CH$_3$ —C(=S)C$_6$H$_3$(CH$_3$)$_2$, and —C(=S)CH$_2$C$_6$Hs, are non-limiting examples of thioacyl groups. The term "thioacyl" therefore encompasses, but is not limited to, groups sometimes referred to as "alkyl thiocarbonyl" and "aryl thiocarbonyl" groups.

The term "alkylsulfonyl" refers to the group —S(=O)$_2$R, in which R is an alkyl, as that term is defined above. Non-limiting examples of alkylsulfonyl groups include:

—S(=O)$_2$ CH$_3$, —S(=O)$_2$CH$_2$CH$_3$, —S(=O)$_2$CH$_2$CH$_2$CH$_3$, —S(=O)$_2$CH(CH$_3$)$_2$, —S(=O)$_2$CH(CH$_2$)$_2$, —S(=O)$_2$-cyclopentyl, and —S(=O)$_2$-cyclohexyl.

Similarly, the terms "alkenylsulfonyl," "alkynylsulfonyl," "arylsulfonyl," "aralkylsulfonyl," "heteroarylsulfonyl," and "heteroaralkylsulfonyl" refer to groups, defined as —S(O)$_2$R, in which R is alkenyl, alkynyl, aryl, aralkyl, heteroaryl, and heteroaralkyl, respectively, as those terms are defined above.

The term "alkylsulfinyl" refers to the group —S(=O)R, in which R is an alkyl, as that term is defined above. Non-limiting examples of alkylsulfinyl groups include —S(=O)CH$_3$, —S(=O) CH$_2$CH$_3$, —S(=O)CH$_2$CH$_2$CH$_3$, —S(=O)CH(CH$_3$)$_2$, —S(=O)CH(CH$_2$)$_2$, —S(=O)-cyclopentyl, and —S(=O)-cyclohexyl.

Similarly, the terms "alkenylsulfinyl," "alkynylsulfinyl," "arylsulfinyl," "aralkylsulfinyl," "heteroarylsulfinyl" and "heteroaralkylsulfinyl" refer to groups, defined as —S(=O)R, in which R is alkenyl, alkynyl, aryl, aralkyl, heteroaryl, and heteroaralkyl, respectively, as those terms are defined above.

The term "alkylammonium" refers to a group, defined as —NH$_2$R$^+$, —NHRR'$^+$, or —NRR'R"$^+$, in which R, R' and R" are the same or different alkyl groups, or any combination of two of R, R' and R" can be taken together to represent an alkanediyl. Non-limiting examples of alkylammonium cation groups include —NH$_2$(CH$_3$)$^+$, —NH$_2$(CH$_2$CH$_3$)+, —NH$_2$(CH$_2$CH$_2$CH$_3$)+, —NH(CH$_3$)$_2$$^+$, —NH(CH$_2$CH$_3$)$_2$$^+$, (CH$_2$CH$_2$CH$_3$)$_2$$^+$, —N(CH$_3$)$_3$$^+$, —N(CH$_3$)(CH$_2$CH$_3$)$_2$$^+$, —N(CH$_3$)$_2$(CH$_2$CH$_3$)+, —NH$_2$C(CH$_3$)$_3$$^+$, —NH(cyclopentyl)$_2$$^+$, and —NH$_2$(cyclohexyl)$^+$.

The term "alkylthiyl" refers to the group —SR. Non-limiting examples of alkylthiyl groups include —S(CH$_3$), —S(CH$_2$CH$_3$), —S(CH$_2$CH$_2$CH$_3$), —S(cyclopentyl), and —S(cyclohexyl).

The term "alkylsilyl" refers to a monovalent group, defined as —SiH$_2$R, —SiHRR', or —SiRR'R", in which R, R' and R" can be the same or different alkyl groups, or any combination of two of R, R' and R" can be taken together to represent an alkanediyl. The groups —SiH$_2$CH$_3$, —SiH(CH$_3$)$_2$, —Si(CH$_3$)$_3$ and —Si(CH$_3$)$_2$C(CH$_3$)$_3$, are non-limiting examples of unsubstituted alkylsilyl groups.

The term "alkylphosphonyl" refers to the group —OPO(OR)$_2$, where R is alkyl, as defined herein.

The term "alkylphosphate" refers to the group —OP(=O)(OH)(OR), in which R is an alkyl, as that term is defined above. Non-limiting examples of alkylphosphate groups include —OP(=O)(OH)(OMe) and —OP(=O)(OH)(OEt).

The term "dialkylphosphate" refers to the group —OP(=O)(OR)(OR'), in which R and R' can be the same or different alkyl groups, or R and R' can be taken together to represent an alkanediyl having two or more saturated carbon atoms, at least two of which are attached via the oxygen atoms to the phosphorus atom. Non-limiting examples of dialkylphosphate groups include —OP(=O)(OMe)$_2$, —OP(=O)(OEt)(OMe) and —OP(=O)(OEt)$_2$.

"Cycloalkyl" means a non-aromatic mono- or multicyclic ring system including about 3 to about 10 carbon atoms, preferably about 5 to about 10 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclyl" or "heterocycloalkyl" means a non-aromatic saturated monocyclic or multicyclic ring system including about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like.

Any of the groups described herein may be unsubstituted or optionally substituted. When modifying a particular group, "substituted" means that the group the term modifies may, but does not have to, be substituted. Substitutions typically replace an available hydrogen with an alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

"Pharmaceutically acceptable salts" means salts of compounds of the present invention which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-l-carboxylic acid, acetic acid, aliphatic mono- and di-carboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl) benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Compounds of the invention may also exist in prodrug form. Since prodrugs are known to enhance numerous desirable qualities of pharmaceuticals, e.g., solubility, bioavailability, manufacturing, etc., the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The novel compounds of this invention find use in modulating IFN-γ-induced NO production in macrophages, said composition having an $IC_{50}$ value of at least less than 0.6 µM, more preferably less than 0.001 µM.

In one embodiment, the novel triterpenoid compounds are of use in a method of modulating excessive nitric oxide or prostaglandin formation in a subject by administering to a subject a pharmaceutically effective amount of one or more triterpenoid compounds, such that the nitric oxide or prostaglandin formation is modulated.

In a further embodiment, the triterpenoid compounds of the invention are of use in a method of preventing or treating a disorder characterized by overexpression of iNOS or COX-2 genes, wherein the method includes administering to a subject a pharmaceutically effective amount of one or more triterpenoid compounds, such that the disorder is prevented or treated. In a preferred embodiment, the disorder includes cancer, diabetic nephropathy, neurodegenerative disease, rheumatoid arthritis, inflammatory bowel disease, and other diseases whose pathogenesis is believed to involve excessive production of either nitric oxide or prostaglandins. In a particular embodiment, the neurodegenerative disease includes Parkinson's disease, Alzheimer's disease, multiple sclerosis, and amyotrophic lateral sclerosis. The cancer may include, e.g., a leukemic cancer or a solid cancer. A leukemic cancer is a cancer of a blood cell, a myeloid cell, a monocytic cell, a myelocytic cell, a promyelocytic cell, a myeloblastic cell, a lymphocytic cell, or a lymphoblastic cell. A solid cancer is a cancer of a bladder cell, a breast cell, a lung cell, a colon cell, a prostate cell, a liver cell, a pancreatic cell, a stomach cell, a testicular cell, a brain cell, an ovarian cell, a skin cell, a brain cell, a bone cell, or a soft tissue cell.

Moreover, the invention provides methods for the treatment and prevention of graft versus host disease (GVHD) by providing a triterpenoid compound of the invention either alone or in conjunction with another agent, such as an immunosuppressive agent such as a corticosteroid or tacrolimus, or a chemotherapeutic agent for the treatment of GVHD. In graft versus host disease the donor immune system mounts a response against the host's organs or tissue. As CDDO compounds, either alone or in conjunction with other agents, can induce apoptosis by inhibiting Bcl-2 and have activity in lymphoid tissue, it is contemplated that the instant triterpenoid compounds can be used to provide therapy for graft versus host diseases.

As a further embodiment of this invention, known and novel triterpenoid compounds described herein can be used to produce stem/progenitor cells with altered expression of one or more of SOX9, COL2A1, TGF-β1, TGF-β2, TGF-β3, BMP2, BMP4, BMPRII, SMAD3, SMAD4, SMAD6, SMAD7, TIMP-1 or TIMP-2, as compared to a control. As is known in the art, stem cells are primal cells found in all multi-cellular organisms. They retain the ability to renew themselves through mitotic cell division and can differentiate into a diverse range of specialized cell types. Mammalian stem cells include embryonic stem cells, derived from blastocysts; adult stem cells, which are found in adult tissues; and cord blood stem cells, which are found in the umbilical cord. In a developing embryo, stem cells can differentiate into all of the specialized embryonic tissues. In adult organisms, stem cells and progenitor cells act as a repair system for the body, replenishing specialized cells.

As stem cells can be grown and transformed into specialized cells with characteristics consistent with cells of various tissues such as muscles or nerves through cell culture, stem cells are of use in medical therapies. In particular, embryonic cell lines, autologous embryonic stem cells generated through therapeutic cloning, and highly plastic adult stem cells from the umbilical cord blood or bone marrow are promising candidates.

"Potency" specifies the differentiation potential (the potential to differentiate into different cell types) of the stem cell. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem/progenitor cells can produce only cells of a closely related family of cells (e.g., hematopoietic stem cells differentiate into red blood cells, white blood cells, platelets, etc.).

The term "differentiation" or "differentiated," as used herein, refers to the developmental process wherein an unspecialized or less specialized cell becomes more specialized for a specific function, such as, for example, the process by which a mesenchymal stem cell becomes a more specialized cell such as a cartilage cell, a bone cell, a muscle cell, or a fat cell. Differentiation can be assessed by identifying lineage-specific markers, such as, for example, aggrecan, a proteoglycan specific for cartilage.

Embryonic stem (ES) cell lines are cultures of cells derived from the epiblast tissue of the inner cell mass (ICM) of a blastocyst. A blastocyst is an early stage embryo, approximately 4 to 5 days old in humans and composed of 50-150 cells. ES cells are pluripotent, and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

A human embryonic stem cell is defined by the presence of several transcription factors and cell surface proteins. The transcription factors Oct-4, Nanog, and Sox2 form the core regulatory network, which ensures the suppression of genes that lead to differentiation and the maintenance of pluripotency. The cell surface proteins most commonly used to identify hES cells are the glycolipids SSEA3 and SSEA4 and the keratan sulfate antigens Tra-1-60 and Tra-1-81. Because of the combined ability of unlimited expansion and pluripotency, embryonic stem cells remain a potential source for regenerative medicine and tissue replacement after injury or disease. Therefore, the present invention contemplates the use of embryonic stem cells. Cells derived from embryonic sources may include embryonic stem cells or stem cell lines obtained from a stem cell bank or other recognized depository institution.

An adult or somatic stem cell, a cell which is found in a developed organism, has two properties: the ability to divide and create another cell like itself, and also divide and create a cell more differentiated than itself. Adult stem cell treatments have been used for many years to successfully treat leukemia and related bone/blood cancers through bone marrow transplants. Therefore, in particular embodiments of the present invention, adult stem cells are used in the methods of the disclosed herein. Pluripotent adult stem cells are rare and generally small in number but can be found in a number of tissues including umbilical cord blood. Most adult stem cells are lineage restricted (multipotent). Therefore, in certain embodiments, the adult stem cells of the invention are multipotent.

Adult stem cells have been identified in many organs and tissues, including brain, bone marrow, peripheral blood, blood vessels, skeletal muscle, skin, teeth, heart, gut, liver, ovarian epithelium, and testis, and are thought to reside in a specific area of each tissue (called a "stem cell niche"). In this respect, stem cells are generally referred by the tissue from which they are derived, e.g., cardiac stem cells are stems that naturally reside within the heart, adipose-derived stem cells are stem cells found in fat tissue, myoblasts are muscle stem cells, dental pulp stem cells are found in the teeth, etc.

Stem cells give rise to a number of different cell types. For example, mesenchymal stem cells ($CD105^+$, $CD90^+$, $CD11b^+$, $CD34^+$ and $CD45^+$) give rise to bone cells (osteocytes), cartilage cells (chondrocytes), fat cells (adipocytes), and other kinds of connective tissue cells such as those in tendons. Hematopoietic stem cells ($Lin^-$, $CD34^+$, $CD90^+$, $CD34^-$ and $CD45^-$) give rise to all the types of blood cells including red blood cells, B lymphocytes, T lymphocytes, natural killer cells, neutrophils, basophils, eosinophils, monocytes, and macrophages. Neural stem cells in the brain ($CD133^+$, $FA-1^+$, $CD34^-$ and $CD45^-$) give rise to nerve cells (neurons), astrocytes and oligodendrocytes. Epithelial stem cells in the lining of the digestive tract occur in deep crypts and give rise to several cell types including absorptive cells, goblet cells, paneth cells, and enteroendocrine cells. Skin stem cells occur in the basal layer of the epidermis and at the base of hair follicles, and give rise to keratinocytes, which migrate to the surface of the skin and form a protective layer. The follicular stem cells can give rise to both the hair follicle and to the epidermis. Neural crest stem cells (p75 receptor$^+$, $\alpha_4$ integrin receptor$^+$, $CD29^+$ and $CD9^+$) differentiate into the cells of the peripheral nervous system. In some embodiments, the invention includes the use of mesenchymal stem cells, hematopoietic stem cells, neural stem cells, epithelial stem cells, skin stem cells, follicular stem cells and/or neural crest stem cells. In other embodiments, the invention includes the use of hematopoietic stem cells, neural stem cells, epithelial stem cells, skin stem cells, follicular stem cells and/or neural crest stem cells. In certain embodiments, stem cells in accordance with the present invention are not mesenchymal stem cells.

Progenitor cells are cells that are direct descendants of stem cells, are typically less potent than stem cells, and have diminished capacity for self-renewal relative to stem cells, but retain the ability to become at least one, if not multiple, cell types. In this respect, multipotent progenitor cells are also encompassed within the scope of the present invention. Multipotent progenitor cells are similar to mesenchymal stem cells as they have the ability to differentiate, in vitro, into cells with phenotypic characteristics of cells from all three germ cell layers (mesoderm, ectoderm and endoderm). Multipotent progenitor cells can be isolated in a fashion similar to mesenchymal stem cells, with adherence to plastic as an initial staple property; however additional separation techniques including magnetic activated cell sorting for $CD45^-$/$TER119^-$ and 96-well single cell isolation/expansion on fibronectin in enriched media are required (Breyer, et al. (2006) *Exp. Hematol.* 34:1596-601). Multipotent progenitor cells possess certain cell surface markers (distinct from mesenchymal stem cells) including CD13, CD31 and SSEA-1 and lack markers including CD3, CD11b, CD19, CD34, CD44, CD45, MHC I and MHC II (Breyer et al. (2006) supra; Jiang, et al. (2002) *Exp. Hematol.* 34:809). Progenitor cells include satellite cells found in muscles; intermediate progenitor cells formed in the subventricular zone; bone marrow stromal cells; periosteum cells, which includes progenitor cells that develop into osteoblasts or chondroblasts; pancreatic progenitor cells; angioblasts or endothelial progenitor cells; and blast cells involved in the generation of B- and T-lymphocytes. In some embodiments, the invention includes the use of satellite cells, intermediate progenitor cells, bone marrow stromal cells, pancreatic progenitor cells, endothelial progenitor cells, and/or blast cells. In other embodiments, the invention includes the use of satellite cells, intermediate progenitor cells, bone marrow stromal cells, pancreatic progenitor cells, endothelial progenitor cells, and/or blast cells. In certain embodiments, a progenitor cell is not a periosteium cell or osteoprogenitor cell.

The invention applies to cells of an embryonic or adult origin in mammals, both human and non-human mammals, including but not limited to human and non-human primates, ungulates, ruminants and rodents. Ungulate species include, but are not limited to, cattle, sheep, goats, pigs, horses. Rodent species include, but are not limited to, rats and mice. The invention may also find application in other mammalian species such as rabbits, cats and dogs. Examples of preferred stem/progenitor cell populations which can be used in accordance with the methods of the present invention include primate stem/progenitor cells, such as human stem/progenitor cells. Such cells include adult human mesenchymal stem cells. As will be appreciated by one of skill in the art, a stem or progenitor cell referred to herein generally refers to a population of stem or progenitor cells.

Stem cells of the present invention can be isolated by conventional methods including Fluorescence Activated Cell Sorting (FACS), microbead separation, or affinity chromatograph using antibodies specific to cell surface antigens. Alternatively, stem cells can be isolated by enzymatic digestion of source tissue and gradient separation with, e.g., PERCOLL or HISTOPAQUE. Once isolated, the stem cells can be maintained and propagated in vitro under controlled conditions. Cells may be cultured in a variety of types of vessels constructed of, for example, glass or plastic. The surfaces of culture vessels may be pre-treated or coated with, for example, collagen, polylysine, or components of the extracellular matrix, to facilitate the cellular adherence. In addition, layers of adherent cells or feeder cells, which are used to support the growth of cells with more demanding growth requirements, may be used.

Cells are normally cultured under conditions designed to closely mimic those observed in vivo. In order to mimic the normal physiological environment, cells are generally incubated in a $CO_2$ atmosphere with semi-synthetic growth media. Culture media is buffered and contains, among other things, amino acids, nucleotides, salts, vitamins, and also a supplement of serum such as fetal calf serum (FCS), horse serum or even human serum. Culture media may be further supplemented with growth factors and inhibitors such as hormones, transferrin, insulin, selenium, and attachment factors.

In certain aspects of the instant invention, cells are cultured prior to contact with a synthetic triterpenoid. They may also be cultured after contact, i.e., after they have been induced to express one or more of the genes disclosed herein or differentiate toward a given or specific phenotype. Cells will be cultured under specified conditions to achieve particular types of differentiation, and provided with various factors necessary to facilitate the desired differentiation.

In some embodiments, cells contacted with a synthetic triterpenoid are also contacted with one or more cell growth and differentiation factors. Cell growth and differentiation factors are molecules that stimulate cells to proliferate and/or promote differentiation of cell types into functionally mature forms. In some embodiments of the invention, cell growth and differentiation factors may be administered in combination with synthetic triterpenoids of the invention in order to direct the administered cells to proliferate and differentiate in a specific manner. One of ordinary skill would recognize that the various factors may be administered prior to, concurrently with, or subsequent to the administration of one or more synthetic triterpenoids of the present invention. In addition, administration of the growth and/or differentiation factors may be repeated as needed.

It is envisioned that a growth and/or differentiation factor may constitute a hormone, cytokine, hematapoietin, colony stimulating factor, interleukin, interferon, growth factor, other endocrine factor or combination thereof that act as intercellular mediators. Examples of such intercellular mediators are lymphokines, monokines, growth factors and traditional polypeptide hormones. Included among the growth factors are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factors -α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; insulin-like growth factor-I and -II; erythropoietin (EPO); osteoinductive factors; interferons such as interferon α, β, and -γ; colony stimulating factors (CSFs) such as macrophage-CSF (M-CSF); granulocyte/macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; IL-13, IL-14, IL-15, IL-16, IL-17, IL-18. As used herein, the term growth and/or differentiation factors include proteins from natural sources or from recombinant cell culture and biologically active equivalents of the native sequence, including synthetic molecules and mimetics.

By way of illustration, further differentiation into ectodermal cells can be achieved by culturing cells in a culture medium containing GDF-9. Further differentiation into endodermal cells can be achieved by culturing cells in a culture medium containing wnt. Further differentiation into mesodermal cells can be achieved by culturing cells in a culture medium containing Activin or Nodal.

The present disclosure provides methods of inducing the expression of one or more of SOX9, COL2A1, TGF-β1, TGF-β2, TGF-β3, BMP2, BMP4, BMPRII, SMAD3, SMAD4, SMAD6, SMAD7, TIMP-1 or TIMP-2, such as in a stem/progenitor cell, and the prevention or treatment of disease. In some embodiments, the expression of one or more of SOX9, COL2A1, TGF-β1, TGF-β2, TGF-β3, BMP2, BMP4, BMPRII, SMAD3, SMAD4, SMAD6, SMAD7, TIMP-1 or TIMP-2 in the stem/progenitor cell induces differentiation. For example, the results presented below demonstrate that CDDO-Imidazolide (CDDO-Im) and CDDO-Ethyl amide (CDDO-EA) induce expression of each of the above-reference genes and induce chondrogenesis in mesenchymal stem cells and organ cultures of newborn mouse calvaria. Accordingly, cells exposed to synthetic triterpenoids under in vitro, in vivo, or ex vivo conditions are of use in the treatment of diseases, conditions or disorders wherein altered gene expression has been shown to provide an advantage and/or transplantation of differentiated cells would provide a benefit. Examples of synthetic triterpenoid-mediated gene induction in particular stem cells and use of the same are as follows.

Synthetic Triterpenoid-Mediated Induction of SOX9.

Sox9 is a member of the Sox gene family, which is characterized by the presence of an HMG box with more than 50% homology to the sex determining gene Sry (Schepers, et al. (2002) *Dev. Cell* 3:167-170). The HMG box can bind and bend DNA, and it has been proposed that Sox genes encode architectural DNA binding proteins. In addition to the HMG box, Sox9 possesses a transactivation domain at its C terminus (Sudbeck, et al. (1996) *Nat. Genet.* 13:230-232), and it has been shown that it can activate the genes M is in testis (De Santa Barbara, et al. (1998) *Mol. Cell Biol.* 18:6653-6665; Arango, et al. (1999) *Cell* 99:409-419) and Col2aI (Bell, et al. (1997) *Nat. Genet.* 16:174-178) during chondrogenesis in vitro and in vivo. Moreover, in vitro studies suggest that Sox genes may also have a role in RNA splicing (Ohe, et al. (2002) *Proc. Natl. Acad. Sci. USA* 99:1146-51).

Recombinant expression of Sox9 in cultured outer root sheath (ORS) cells has been shown to induce the expression of keratin 15, increase the proliferation of ORS cells in vitro, and enhance colony-forming activity (Shi, et al. (2011) *Annals Dermatol.* 23:183-143). In this respect, Sox9 has potential importance in the regulation of hair follicle homeostasis. Accordingly, the induction of Sox9 in ORS cells by synthetic triterpenoids could be of use in modulating hair follicle homeostasis.

The neural crest is a transient migratory population of stem cells derived from the dorsal neural folds at the border between neural and non-neural ectoderm. Following induction, prospective neural crest cells are segregated within the neuroepithelium and then delaminate from the neural tube and migrate into the periphery, where they generate multiple differentiated cell types. Group E Sox genes (Sox8, Sox9 and Sox10) are expressed in the prospective neural crest and Sox9 expression precedes expression of premigratory neural crest markers. Forced expression of Sox9 promotes neural-crest-like properties in neural tube progenitors at the expense of central nervous system neuronal differentiation. Subsequently, in migratory neural crest cells, SoxE gene expression biases cells towards glial cell and melanocyte fate, and away from neuronal lineages (Cheung & Briscoe (2003) *Development* 130:5681-93). In this respect, Sox9 and Sox10 promote oligodendrocyte specification and terminal differentiation, respectively (Finzsch, et al. (2008) *Development* 13:637-646). Therefore, synthetic triterpenoid-mediated induction of Sox9 in NC cells could be useful in the production of oligodendrocytes and therapies for diseases such as familial dysautonomia, which affects the development and function of nerves throughout the body.

Synthetic Triterpenoid-Mediated Induction of BMP-2.

TGF-β and BMP-2 applied to undifferentiated murine embryonic stem cells have been shown to up-regulate mRNA of mesodermal- (Brachyury) and cardiac-specific transcription factors (Nkx2.5, MEF2C) (Behfar, et al. (2002) *FASEB J.* 16:1558-66). Embryoid bodies generated from stem cells primed with these growth factors demonstrated an increased potential for cardiac differentiation with a significant increase in beating areas and enhanced myofibrillogenesis. In an environment of post-mitotic cardiomyocytes, stem cells engineered to express a fluorescent protein under the control of a cardiac promoter differentiated into fluorescent ventricular myocytes beating in synchrony with host cells, a process significantly enhanced by TGF-β or BMP-2. In vitro, disruption of the TGF-β/BMP signaling pathways by latency-associated peptide and/or noggin prevented differentiation of stem cells. In vivo, transplantation of stem cells into heart also resulted in cardiac differentiation provided that TGF-β/BMP-2 signaling was intact. In infarcted myocardium, grafted stem cells differentiated into functional cardiomyocytes integrated with surrounding tissue, improving contractile performance. Thus, embryonic stem cells are directed to differentiate into cardiomyocytes by signaling mediated through TGF-β/BMP-2, a cardiac paracrine pathway required for therapeutic benefit of stem cell transplantation in diseased heart (Behfar, et al. (2002) supra). Therefore, synthetic triterpenoid-mediated induction of BMP-2 and TGF-β in stem cells is of use in stimulating cardiomyocyte differentiation in vitro or in vivo for treatment of heart disease.

Atrioventricular (AV) endocardium transforms into the cushion mesenchyme, the primordia of the valves and membranous septa, through epithelial-mesenchymal transformation (EMT). BMP-2 is known to be critical for AV EMT and post-EMT AV valvulogenesis. In particular, using stage-24 AV cushion mesenchymal cell aggregates cultured on 3D-collagen gels, exogenous BMP-2 was shown to induce migration of the mesenchymal cells into the collagen gels, and promote expression of periostin, a known valvulogenic matrix maturation mediator. Moreover, transcripts of Twist and Id1, which have been implicated in cell migration in embryogenesis and activation of the periostin promoter, were induced by BMP-2 (Inai, et al. (2008) Dev. Biol. 315:383-96). Therefore, synthetic triterpenoid-mediated induction of BMP-2 in AV cushion mesenchymal cell aggregates is of use in post-EMT AV cushion tissue maturation and differentiation.

The atrioventricular heart valve leaflets and chordae tendineae are composed of diverse cell lineages and highly organized extracellular matrices that share characteristics with cartilage and tendon cell types in the limb buds and somites. During embryonic chicken valvulogenesis, aggrecan and sox9, characteristic of cartilage cells, are observed in the AV valve leaflets, in contrast to tendon-associated genes scleraxis and tenascin, present in the chordae tendineae. In the limb buds and somites, cartilage cell lineage differentiation is regulated by BMP2, while FGF4 controls tendon cell fate. In this respect, it has been demonstrated BMP2 is sufficient to activate Smad1/5/8 phosphorylation and induce sox9 and aggrecan expression in cells from prefused endocardial cushions (Lincoln, et al. (2006) *Dev. Biol.* 292:292-302). Therefore, synthetic triterpenoid-mediated induction of BMP-2 is of use in atrioventricular valve progenitor cell diversification into leaflets.

Myocardial and coronary development are both critically dependent on epicardial cells. During cardiomorphogenesis, a subset of epicardial cells undergoes an epithelial-to-mesenchymal transition (EMT) and invades the myocardium to differentiate into various cell types, including coronary smooth muscle cells and perivascular and cardiac interstitial fibroblasts. It has been demonstrated that epicardium-derived cells (EPDCs) treated with TGF-β1 or BMP-2 obtain characteristics of smooth muscle cells (van Tuyn, et al. (2007) *Stem Cells* 25:271-8). Therefore, synthetic triterpenoid-mediated induction of BMP-2 and TGF-β1 in epicardium-derived cells may be of use in stimulating coronary smooth muscle cell differentiation.

Oligodendrocyte precursor cells (OPCs) can differentiate into oligodendrocytes or astrocytes, depending on cellular microenvironments. OPCs, cultured in medium supplemented with 10% (v/v) fetal bovine serum (FBS), give rise to type II astrocytes that express glial fibrillary acidic protein and a cell surface ganglioside that is recognized by A2B5 monoclonal antibody. Moreover, BMPs have been reported to be involved in astrocyte differentiation of neural progenitor cells. Therefore, it was determined whether BMPs are responsible for the serum-mediated astrocyte differentiation from OPCs (Hu, et al. (2010) *Tohoku J. Exp. Med.* 222:195-200). When OPCs were cultured in the medium containing 10% FBS, cells (more than 95%) differentiated into type II astrocytes. However, when OPCs were pretreated with noggin, the degree of astrocyte differentiation was markedly decreased from 95.39 to 38.36% (Hu, et al. (2010) supra). Taken together, these results indicate that BMP signaling may be responsible for the serum-mediated astrocyte differentiation of OPCs. Therefore, synthetic triterpenoid-mediated induction of BMP-2 and BMP-4 in OPCs may be of use in stimulating serum-mediated astrocyte differentiation.

Synthetic Triterpenoid-Mediated Induction of BMP-4.

The neural crest-derived cell population that colonizes the bowel (ENCDC) contains proliferating neural/glial progenitors. Enteric gliogenesis has been analyzed in mice that overexpress the BMP antagonist, noggin, or BMP-4 in the primordial ENS. Noggin-induced loss-of-function decreased, while BMP4-induced gain-of-function increased the glial density and glia/neuron ratio. When added to immunoisolated ENCDC, BMPs provoked nuclear translocation of phosphorylated SMAD proteins and enhanced both glial differentiation and expression of the neuregulin receptor ErbB3. This analysis indicated that BMPs are required for enteric gliogenesis and act by promoting responsiveness of ENCDC to ErbB3 ligands such as GGF2 (Chalazonitis, et al. (2011) *Dev. Biol.* 350:64-79). Therefore, synthetic triterpenoid-mediated induction of BMP-2 and BMP-4 in neural crest-derived cells is of use in stimulating enteric gliogenesis.

Bone morphogenetic proteins promote astrocytic differentiation of cultured subventricular zone stem cells. In addition, it has been demonstrated that BMPs regulate the astrocytic lineage in vivo (Gomex, et al. (2003) *Dev. Biol.* 255:164-77).

Transgenic mice were constructed that overexpress BMP-4 under control of the neuron-specific enolase (NSE) promoter. The overexpression of BMP-4 resulted in a remarkable 40% increase in the density of astrocytes in multiple brain regions accompanied by a decrease in the density of oligodendrocytes ranging between and 26%, depending on the brain region and the developmental stage. No changes in neuron numbers or the pattern of myelination were detected, and there were no gross structural abnormalities. Coculture of transgenic neurons with neural progenitor cells significantly enhanced astrocytic lineage commitment by the progenitors; an effect which was blocked by the BMP inhibitor Noggin, indicating that the stimulation of astrogliogenesis was due to BMP-4 release by the transgenic neurons. These observations indicate that BMP-4 directs progenitor cells in vivo to commit to the astrocytic rather than the oligodendroglial lineage (Gomex, et al. (2003) supra). Therefore, synthetic triterpenoid-mediated induction of BMP-4 in neural progenitor cells may be of use in stimulating astrocyte development.

It has been shown that that keratinocytes treated with ESC-conditioned medium (CM) change their morphology and are stimulated to express the pluripotency regulator, Oct-4, and its target transcripts, Sox-2, Nanog, Utfl and Rex-1; an effect that is mediated by BMP-4 (Grinnell & Bickenbach (2007) Cell Prolif. 40:685-70). Pre-treated keratinocytes could be specifically directed to differentiate into cells of the neuronal lineage. The majority of responsive keratinocytes were the epidermal stem cell population, with a small percentage of transit-amplifying cells also being affected. These results indicate that ESC-CM contains a number of factors, including BMP-4, which are capable of reprogramming mouse skin keratinocytes to make them more developmentally potent, as evidenced by their ability to be re-differentiated into cells of the neuronal lineage (Grinnell & Bickenbach (2007) supra). An increase in developmental potential combined with directed differentiation could increase the therapeutic relevancy of somatic cells. In this respect, synthetic triterpenoid-mediated induction of BMP-4 in ESCs may be of use in reprogramming keratinocytes.

When differentiated in the presence of activin A in serum-free conditions, mouse embryonic stem cells efficiently generate an endoderm progenitor population defined by the coexpression of either Brachyury, Foxa2 and c-Kit, or c-Kit and Cxcr4. Specification of these progenitors with BMP-4 in combination with basic fibroblast growth factor (FGF) and activin A results in the development of hepatic populations highly enriched (45-70%) for cells that express the alpha-fetoprotein and albumin proteins (Gouon-Evans (2006) Nat. Biotechnol. 24:1402-11). These cells also express transcripts of Afp, Alb1, Tat, Cps1, Cyp7a1 and Cyp3a11; they secrete albumin, store glycogen, show ultrastructural characteristics of mature hepatocytes, and are able to integrate into and proliferate in injured livers in vivo and mature into hepatocytes expressing dipeptidyl peptidase IV or fumarylacetoacetate hydrolase (Gouon-Evans (2006) supra). Therefore, synthetic triterpenoid-mediated induction of BMP-4 in ESCs cultured in the presence of activin A and FGF may be of use in generating cells with an immature hepatocytic phenotype and in the treatment of injured livers.

When neural progenitors induced from ES cells in a serum-free suspension culture are subsequently treated with BMP-4 and Wnt3a, a significant proportion of these neural cells become Math1+ (Su, et al. (2006) Dev. Biol. 290:287-96). The induced Math1+cells are mitotically active and express markers characteristic of granule cell precursors (Pax6, Zic1, and Ziprol). After purification and coculture with postnatal cerebellar neurons, ES cell-derived Math1+ cells exhibit typical features of neurons of the external granule cell layer, including extensive motility and a T-shaped morphology. In addition, differentiation of L7+/Calbindin-D28K+neurons (characteristic of Purkinje cells) is induced under similar culture conditions but exhibits a higher degree of enhancement by Fgf8 rather than by Wnt3a (Su, et al. (2006) supra). Therefore, synthetic triterpenoid-mediated induction of BMP-4 in ES cell-derived Math1+cells cultured in the presence of Wnt3a or Fgf8 may be of use in generating Math1+ cerebellar granule cell precursors and Purkinje cells.

The potential of different growth factors (basic fibroblast growth factor (bFGF), TGF-β1, activin-A, BMP-4, hepatocyte growth factor (HGF), epidermal growth factor (EGF), beta nerve growth factor ((NGF), and retinoic acid) to direct the differentiation of human ES-derived cells in vitro has been analyzed (Schuldiner, et al. (2000) PNAS 97:11307-12). Differentiation of the cells was assayed by expression of 24 cell-specific molecular markers that cover all embryonic germ layers and 11 different tissues. Each growth factor had a unique effect that may have resulted from directed differentiation and/or cell selection, and could be divided into three categories: growth factors that mainly induce mesodermal cells (Activin-A and TGF-β1); factors that activate ectodermal and mesodermal markers (retinoic acid, EGF, BMP-4, and bFGF); and factors that allow differentiation into the three embryonic germ layers, including endoderm (NGF and HGF) (Schuldiner, et al. (2000) supra). Therefore, synthetic triterpenoid-mediated induction of BMP-4 and/or TGF-β1 in human ES cells may be of use in generating mesodermal cells and/or ectodermal cells.

The limited clinical response observed in many patients with colorectal cancer may be related to the presence of chemoresistant colorectal cancer stem cells (CRC-SCs). There is evidence that many common cancers, including skin cancer, breast cancer and leukemia, can result from transforming events that occur in adult stem cells (Perez-Losada & Balmain (2003) Nat. Rev. Cancer 3:434-443; Al-Hajj, et al. (2003) Proc. Natl. Acad. Sci. USA 100:3983-3988; Reya, et al. (2001) Nature 414:105-111). Indeed, functional parallels exist between tumorigenic and normal stem cells. Both cell types demonstrate significant proliferative potential, the ability to self-renew, and the ability to generate new tissues. However, tumorigenic stem cells lack the normal growth regulatory mechanisms that limit the uncontrolled proliferation of stem cells (Reya, et al. (2001) supra). Tumorigenic stem cells arise in normal adult stem cell populations through the accumulation of multiple transforming mutations. As adult stem cells can persist and self-renew for the lifespan of the individual, these cells are more likely to accrue the genetic lesions necessary for malignant transformation. Such transformed tumorigenic stem cells, arising in normal adult stem cell populations, can initiate cancer development (Reya, et al. (2001) supra). Furthermore, tumorigenic stem cells may also play important roles in tumor evolution, metastatic invasion and local recurrence following treatment.

Cancer stem cells constitute only a small proportion of a tumor or a cancerous tissue. But the cancer stem cells have a unique ability to establish new colonies of cancer cells. For example, when mouse myeloma cells are obtained from mouse ascites, separated from normal hematopoietic cells, and put into in vitro colony-forming assays, only 1 in 10,000 to 1 in 100 cancer cells were able to form colonies (Park, et al. (1971) J. Nat. Cancer Inst. 46:411-422). Even when leukemic cells are transplanted in vivo, only 1-4% of cells form spleen colonies (Bruce, et al. (1963) Nature 199:79-80; Bergsagel, et al. (1968) Cancer Res. 28:2187-2196).

It has been demonstrated that BMP-4 promotes the differentiation of normal colonic stem cells. Therefore, it was determined whether BMP-4 might be used to induce differentiation of CRC-SCs for therapeutic purposes (Lombardo, et al. (2011) *Gastroenterology* 140:297-309). CRC-SCs were isolated from tumor samples based on expression of CD133 or using a selection culture medium. BMP-4 expression and activity on CRC-SCs were evaluated and it was found that CRC-SCs did not express BMP-4 whereas differentiated cells did. Recombinant BMP-4 promoted differentiation and apoptosis of CRC-SCs; this effect did not depend on Smad4 expression level or microsatellite stability. BMP-4 activated the canonical and noncanonical BMP signaling pathways, including phosphoInositide 3-kinase (PI3K) and PKB (protein kinase B)/AKT. The potential therapeutic effect of BMP-4 was also assessed in immunocompromised mice after injection of CRC-SCs that responded to chemotherapy or that did not. Administration of BMP-4 to immunocompromised mice with tumors that arose from CRC-SCs increased the antitumor effects of 5-fluorouracil and oxaliplatin. BMP-4 promoted terminal differentiation, apoptosis, and chemosensitization of CRC-SCs in tumors that did not have simultaneous mutations in Smad4 and constitutive activation of PI3K (Lombardo, et al. (2011) supra). Therefore, synthetic triterpenoid-mediated induction of BMP-4 in CRC-SCs may be of use in combination with anti-cancer agents in the treatment of advanced colorectal tumors.

Human glioblastoma is a heterogenous tumor composed of tumor cells and a small portion of cancer stem cells, which have a high tumorigenic potential and a low proliferation rate. Glioma cancer stem cells are phenotypically similar to the normal stem cells, they express CD133 gene and other genes characteristic of neural stem cells and posses the self-renewal potential. Cancer stem cells derived from glioblastoma are capable of recapitulating original polyclonal tumors when xenografted to nude mice. They are chemoresistant and radioresistant and therefore responsible for tumor progression and recurrence after conventional glioblastoma therapy. BMP-4 has been shown to trigger a significant reduction in the stem-like, tumor-initiating precursors of human glioblastomas (GBMs)(Piccirillo, et al. (2006) Nature 444:761-765). Transient in vitro exposure to BMP-4 abolishes the capacity of transplanted GBM cells to establish intracerebral GBMs. Most importantly, in vivo delivery of BMP-4 effectively blocks the tumor growth and associated mortality that occur in 100% of mice after intracerebral grafting of human GBM cells. BMP-4 activates its cognate receptor and triggers the Smad signaling cascade in cells isolated from human GBMs. This is followed by a reduction in proliferation, and increased expression of markers of neural differentiation, with no effect on cell viability. The concomitant reduction in clonogenic ability, in the size of the CD133+ population and in the growth kinetics of GBM cells indicates that BMP-4 reduces the tumor-initiating cell pool of GBMs (Piccirillo, et al. (2006) supra). Therefore, synthetic triterpenoid-mediated induction of BMP-4 in chemoresistant GBM cells may be of use in the treatment of GBM.

Synthetic Triterpenoid-Mediated Induction of TGF-β1.

Engineering vascularized tissue is crucial for its successful implantation, survival, and integration with the host tissue. Vascular smooth muscle cells (v-SMCs) provide physical support to the vasculature and aid in maintaining endothelial viability. By supplementing ESCs with platelet-derived growth factor-BB (PDGF-BB) and TGF-β1, human ESCs could be differentiated into smooth-muscle-like cells (SM-LCs) (Vo, et al. (2010) *Stem Cell Rev.* 6:237-47). The SMLCs highly expressed specific smooth muscle cell (SMC) markers including alpha-smooth muscle actin, calponin, SM22, and smooth muscle myosin heavy chain; secreted fibronectin and collagen; and contracted in response to carbachol. In vitro tubulogenesis assays revealed that these hESC-derived SMLCs interacted with human endothelial progenitor cell (EPCs) to form longer and thicker cord-like structures in vitro thereby supporting and augmenting capillary-like structures (Vo, et al. (2010) supra). Therefore, synthetic triterpenoid-mediated induction of TGF-β1 in ESCS may be of use in combination with PDGF-BB to produce smooth-muscle-like cells for therapeutic vascular tissue engineering.

Stem cell factor is essential to the migration and differentiation of melanocytes during embryogenesis based on the observation that mutations in either the stem cell factor gene, or its ligand, KIT, result in defects in coat pigmentation in mice. Stem cell factor is also required for the survival of melanocyte precursors while they are migrating towards the skin. Using an immature melanocyte precursor cell line, it has been demonstrated that TGF-β1 promotes melanocyte precursor proliferation in autocrine and/or paracrine regulation (Kawakami, et al. (2002) *J. Invest. Dermatol.* 118:471-8). In addition, an anti-TGF-β1 antibody decreased the number of KIT-positive neural crest cells in a neural crest cell primary culture system, and abolished the growth of the neural crest cells in a wild-type neural crest explant. These results indicate that TGF-β1 affects melanocyte precursor proliferation and differentiation in the presence of stem cell factor/KIT in an autocrine/paracrine manner (Kawakami, et al. (2002) supra). Therefore, synthetic triterpenoid-mediated induction of TGF-β1 in neural crest stem cells or melanocyte precursor cells may be of use in combination with stem cell factor and KIT to produce melanocytes for therapeutic strategies in the treatment of pigment cell disorders.

Synthetic Triterpenoid-Mediated Induction of TGF-β1.

Oligodendrocyte progenitor cells derived from human embryonic stem cells have been reported to remyelinate axons and improve locomotor function in a rodent model of spinal cord injury. It has been demonstrated that human ES cell-derived OPCs express functional levels of midkine, hepatocyte growth factor (HGF), activin A, TGF-β2, and brain-derived neurotrophic factor (BDNF), proteins with reported trophic effects on neurons (Zhang, et al. (2006) *Stem Cells Dev.* 15:943-52). The neurotrophic activity of hES cell-derived OPCs was further demonstrated by stimulatory effects on neurite outgrowth of adult rat sensory neurons in vitro (Zhang, et al. (2006) supra). Therefore, synthetic triterpenoid-mediated induction of TGF-β2 in human ES cell-derived OPCs may be of use in remyelinating axons and improving locomotor function for therapeutic strategies in the treatment of spinal cord injury.

The effects of TGF-β2 and glial cell line-derived neurotrophic factor (GDNF) in the differentiation of midbrain progenitors toward a dopaminergic phenotype have been analyzed (Roussa, et al. (2008) *Stem Cells* 26:1683-94). This analysis indicated that neurturin and persephin (PSPN), but not GDNF, were capable of transient induction of dopaminergic neurons in vitro. This process, however, required the presence of endogenous TGF-β. In vitro, combined TGF-β/PSPN treatment achieved a yield of approximately 20% TH-positive cells that were less vulnerable against 1-methyl-4-phenyl pyridinium ion toxicity. These results indicate that TGF-β is required for the induction of dopaminergic neurons, whereas GDNF is required for regulating and/or maintaining a differentiated neuronal phenotype (Roussa, et al. (2008) supra). Therefore, synthetic triterpenoid-mediated induction of TGF-β2 in midbrain progenitor cells, in combination with PSPN, may be of use as a potent inductive cocktail for the generation of dopaminergic neurons of use in tissue engineering and cell replacement therapies for Parkinson's disease.

Synthetic Triterpenoid-Mediated Induction of TGF-β3.

Skin grafts are frequently used for a variety of indications in plastic and reconstructive surgery. Their necrosis is a common complication, while different therapies have been proposed. Currently, ASCs hold great promise for their angiogenic potential and role during tissue repair. In this respect, it has been demonstrated that autologous transplantation of ASCs can increase angiogenesis, skin-graft survival and wound healing (Zografou, et al. (2011) *J. Plast. Reconstr. Aesthet Surg.* 64:1647-56). ASCs were isolated, cultured, labelled with fluorescent dye and injected under full-thickness skin grafts in rats. Collagen's framework and angiogenesis were assessed, as were levels of vascular endothelial growth factor (VEGF) and TGF-β3. Statistically significant increases of microvessel density, collagen density, VEGF and TGF-β3 expression were noted in the ASC-treated group. Therefore, synthetic triterpenoid-mediated induction of TGF-β3 in ASCs may be of use in increasing full-thickness skin-graft survival in skin-graft surgery.

Many inductive factors participate in the initial endocardial to mesenchymal transformation event necessary to form the prevalvular cushion. Using embryonic valve progenitor cells in in vitro three-dimensional tissue-engineered models of embryonic valvular remodeling with in vivo analysis, the roles of three prominent growth factors during avian mitral valvulogenesis have been determined (Chiu, et al. (2010) *Tissue Engin. Part A* 16:3375-83). This analysis indicated that TGF-β3, BMP-2, and vascular endothelial growth factor A (VEGFA) are expressed in spatiotemporally distinct patterns and at different levels within remodeling embryonic valves in vivo. TGF-β3 induced cell migration, invasion, and matrix condensation; BMP-2 induced invasion; and VEGFA inhibited invasion but increased migration (Chiu, et al. (2010) supra). Therefore, synthetic triterpenoid-mediated induction of TGF-β3 and BMP-2 in embryonic valve progenitor cells may be of use in facilitating valvulogenic remodeling and phenotype maturation, which can be integrated into clinically needed regenerative strategies for heart valve disease and to accelerate the development of engineered tissue valves.

In culture, BMP-2 and TGF-β3 promote neurogenesis at the expense of a smooth-muscle-like fate in clusters of neural-crest-derived multipotent progenitor cells. In this respect, neurons generated by TGF-β3 factors belong to the autonomic lineage and cells within the developing sympathetic ganglia express TGF-β3-type II receptor. It has been suggested that TGF-β3 functions in a biphasic manner during autonomic gangliogenesis to control both neurogenesis and subsequently the number of neurons generated from progenitor cells (Hagedorn, et al. (2000) *Dev. Biol.* 228:57-72). Therefore, synthetic triterpenoid-mediated induction of TGF-β3 in neural-crest-derived multipotent progenitor cells may be of use in facilitating neurogenesis and the treatment of neurodegenerative diseases such as Parkinson's disease.

Synthetic Triterpenoid-Mediated Induction of Smad3.

It has been demonstrated that Smad3-null mice have decreased muscle mass and pronounced skeletal muscle atrophy (Ge, et al. (2011) *Cell Res.* 21:1591-604). Consistent with this, increases in protein ubiquitination and elevated levels of the ubiquitin E3 ligase MuRF1 is observed in muscle tissue isolated from Smad3-null mice. Loss of Smad3 also led to defective satellite cell (SC) functionality. Smad3-null SCs showed reduced propensity for self-renewal, which may lead to a progressive loss of SC number. Decreased SC number was observed in skeletal muscle from Smad3-null mice showing signs of severe muscle wasting. Further in vitro analysis of primary myoblast cultures identified that Smad3-null myoblasts exhibit impaired proliferation, differentiation and fusion, resulting in the formation of atrophied myotubes. A search for the molecular mechanism revealed that loss of Smad3 results in increased myostatin expression in Smad3-null muscle and myoblasts. Given that myostatin is a negative regulator, increased myostatin levels appear to be responsible for the atrophic phenotype in Smad3-null mice. Consistent with this theory, inactivation of myostatin in Smad3-null mice rescues the muscle atrophy phenotype (Ge, et al. (2011) *Cell Res.* 21:1591-604). Given the role of Smad3 in satellite cell function, synthetic triterpenoid-mediated induction of Smad3 in satellite cells may be of use in facilitating muscle differentiation and fusion to augment existing muscle fibers and to form new fibers following injury or disease.

It has been shown that treatment of mouse embryonic stem cells and human MSCs from fetal membranes of term placenta with hyaluronan mixed esters of butyric and retinoic acids (HBR) facilitates stem cell cardiogenesis (Maioli, et al. (2010) *PLoS One* 5:e15151). HBR differentially affects the patterning of Smad proteins by enhancing gene and protein expression of Smadl, 3, and 4, while down-regulating Smad7. Chromatin immune precipitation and transcriptional analyses showed that HBR increased the transcription of the cardiogenic gene Nkx-2.5 through Smad4 binding to its own consensus Smad site. Treatment of mouse embryonic stem cells and MSCs with HBR led to the concomitant overexpression of both Smad4 and a-sarcomeric actinin. Smad4 silencing by the aid of lentiviral-mediated Smad4 shRNA confirmed a dominant role of Smad4 in HBR-induced cardiogenesis (Maioli, et al. (2010) supra). Therefore, synthetic triterpenoid-mediated induction of Smad4 in embryonic stem cells or MSCs is of use in facilitating stem cell cardiogenesis in the treatment of cardiac disease and injury.

Neuronal differentiation mechanisms following treatment of neural stem/progenitor cells (NPCs) with a G1/S-phase cell cycle blocker have been investigated (Misumi, et al. (2008) *Eur. J. Neurosci.* 28:1049-59). The addition of deferoxamine (DFO) or aphidicolin (Aph) to neurospheres for 8 hours, followed by 3 days of differentiation, resulted in an increased number of neurons and neurite outgrowth. DFO induced enhanced expression of TGF-β1 and cdk5 at 24 hours after differentiation, whereas Aph only increased TGF-β1 expression. DFO-induced neurogenesis and neurite outgrowth were attenuated by administration of a cdk5 inhibitor, roscovitine, suggesting that the neurogenic mechanisms differ between DFO and Aph. TGF-β1 did not increase neurite outgrowth but rather the number of beta-tubulin III-positive cells, which was accompanied by enhanced p27(kip1) mRNA expression. In addition, TGF-β receptor type II expression was observed in nestin-positive NPCs. Results indicated that DFO-induced TGF-β1 signaling activated Smad3 translocation from the cytoplasm to the nucleus. In contrast, TGF-β3 signaling inhibition, via a TGF-β3 receptor type I inhibitor (SB-505124), resulted in decreased DFO-induced neurogenesis, in conjunction with decreased p27(kip1) protein expression and Smad3 translocation to the nucleus. These results indicate that cell cycle arrest during G1/S-phase induces TGF-β1 expression. This, in turn, prompts enhanced neuronal differentiation via Smad3 translocation to the nucleus and subsequent p27(kip1) activation in NPCs (Misumi, et al. (2008) supra). Therefore, synthetic triterpenoid-mediated induction of Smad3 and/or TGF-β3 in neural progenitor cells is of use in facilitating neurogenesis and neurite outgrowth in the treatment of neurodegenerative disease or nerve injury.

Synthetic Triterpenoid-Mediated Induction of Smad4.

In the mammalian brain, neurogenesis continues only in few regions of the forebrain. It has been shown that BMP-mediated signaling is active in adult neural stem cells and is crucial to initiate the neurogenic lineage in the adult mouse subependymal zone (Colak, et al. (2008) *J. Neurosci.* 28:434-46). Conditional deletion of Smad4 in adult neural stem cells severely impairs neurogenesis, and this is phenocopied by infusion of Noggin, an extracellular antagonist of BMP. Smad4 deletion in stem, but not progenitor cells, as well as Noggin infusion lead to an increased number of Olig2-expressing progeny that migrate to the corpus callosum and differentiate into oligodendrocytes. Transplantation experiments further verified the cell-autonomous nature of this phenotype. Thus, BMP-mediated signaling via Smad4 is required to initiate neurogenesis from adult neural stem cells and suppress the alternative fate of oligodendrogliogenesis (Colak, et al. (2008) supra). Accordingly, synthetic triterpenoid-mediated induction of Smad4 in adult neural stem cells may be of use in facilitating neurogenesis in the treatment of neurodegenerative disease or nerve injury.

Synthetic Triterpenoid-Mediated Induction of Smad6.

Neural stem cells were differentiated into astrocytes to analyze gene expression patterns (Park, et al. (2012) *Neurosci. Lett.* 506:50-4). Amongst the analyzed genes, 1898 genes were up-regulated relative to the neural stem cells, whereas 1642 genes were down-regulated. The up-regulated genes included Gfap, Smad6, Fst, Tgfb2 and Cdkn2. The down-regulated genes included Ccnb1, Ccnd1 and Ccnd2. In addition, gene networks associated with BMP and TGF-β2 signaling pathways were identified using Ingenuity Pathway Analysis. These results suggest that the differentiation of neural stem cells into astrocytes is based on a combinatorial network of various signaling pathways, including cell cycle, BMP and TGF-β2 signaling (Park, et al. (2012) supra). Accordingly, synthetic triterpenoid-mediated induction of Smad6 and/or BMP and/or TGF-β2 in adult neural stem cells may be of use in facilitating astrocyte formation in the repair of the brain or spinal cord following traumatic injury.

Synthetic Triterpenoid-Mediated Induction of Smad7.

The role of Smad7 during skeletal muscle cell differentiation has been assessed (Kollias, et al. (2006) *Mol. Cell Biol.* 26:6248-60). In these studies, increased expression of Smad7 has been shown to abrogate myostatin-but not TGF-p1-mediated repression of myogenesis. Further, constitutive expression of exogenous Smad7 potently enhances skeletal muscle differentiation and cellular hypertrophy. Conversely, targeting of endogenous Smad7 by small interfering RNA inhibits muscle cell differentiation, indicating an essential role for Smad7 during myogenesis. Congruent with a role for Smad7 in myogenesis, it has been observed that the muscle regulatory factor (MyoD) binds to and transactivates the Smad7 proximal promoter region. Furthermore, Smad7 directly interacts with MyoD and enhances MyoD transcriptional activity. Thus, Smad7 cooperates with MyoD, creating a positive loop to induce Smad7 expression and to promote MyoD driven myogenesis. Taken together, these data implicate Smad7 as a fundamental regulator of differentiation in skeletal muscle cells (Kollias, et al. (2006) supra). Accordingly, synthetic triterpenoid-mediated induction of Smad7 may be of use in facilitating skeletal muscle cell differentiation in the repair of the muscle following traumatic injury or surgery.

As indicated herein, synthetic triterpenoids induce gene expression and stem/progenitor cell differentiation. In this respect, the present invention also provides a method for the treatment of a patient suffering from a degenerative disease or injury by transplantation into said patient of a population of stem/progenitor cells treated with a synthetic triterpenoid. Transplantation can be achieved using any conventional stem cell transplant procedure with or without a scaffold or matrix. In accordance with some embodiments, degenerative diseases or injuries that may be treated in accordance with this method of the invention, include but are not limited to, skin wounds or injury, muscle injury, Parkinson's disease, diabetes, nerve injury including spinal cord injury, amyotrophic lateral sclerosis, traumatic brain injury, cardiac injury or disease, baldness, myocardial infarction, muscular dystrophy, or liver disease or injury. In addition, the synthetic triterpenoids of the instant invention find application in the treatment of congenital disorders. In some embodiments, the congenital disorder is familial dysautonomia, a congenital heart defect (e.g., congenital heart valve disease), a dysganglionic disorder in the gastrointestinal tract such as hypoganglionosis or Hirschsprung's disease, or a pigment cell disorder such as vitiligo. Furthermore, the synthetic triterpenoids of the invention find application in the treatment of resistant cancers such as chemoresistant colorectal cancer or gliomas. Embodiments of this method of the invention, therefore extend to the use of cells prepared according the present invention in the preparation of a medicament for the treatment of a degenerative disease, injury or congenital disorder.

Exemplary stem/progenitor cells, which can be treated with a synthetic triterpenoid, the result of treatment, and the therapeutic use of said cells are listed in Table 1.

TABLE 1

| Stem/ Progenitor Cell | Result of Treatment with a Synthetic Triterpenoid | Therapeutic Uses |
| --- | --- | --- |
| Adipose tissue-derived mesenchymal stem cells | Induce differentiation of skin cells and stimulation of angiogenesis | Increase skin-graft survival in skin-graft surgery |
| Valve progenitor cells | Atrioventricular diversification into leaflets | Repair of cardiac injury |
|  | Valvulogenic remodeling and phenotype maturation | Valve tissue engineering and treatment of heart valve disease |
| Chemoresistant cancer stem cells | Differentiation and apoptosis of chemoresistant cancer stem cells | Treatment of advanced colorectal or GBM tumors |
| Embryonic stem cells | Induce cardiomyocyte differentiation | Treatment of heart disease and injury |
|  | Reprogram keratinocytes for differentiation into neuronal lineage | Treatment of Neurodegenerative disease |
|  | Produce cells with immature hepatocytic phenotype | Treatment of liver injury or disease |
|  | Induce neural cell differentiation | Treatment of neurodegenerative disease or brain injury |
|  | Induce mesodermal cell and/or ectodermal cell differentiation | Treatment of muscle, skin or neuronal injury |
|  | Induce production of smooth-muscle-like cells | Vascular tissue engineering |
| Epicardium-derived progenitor cells | Stimulate coronary smooth muscle cell differentiation | Treatment of heart disease or cardiac injury |
| Melanocyte precursor cells | Induce production of melanocytes | Treatment of pigment cell disorders |

TABLE 1-continued

| Stem/ Progenitor Cell | Result of Treatment with a Synthetic Triterpenoid | Therapeutic Uses |
|---|---|---|
| Mesenchymal stem cell | Induce cardiogenesis or atrioventricular cushion tissue maturation and differentiation | Treatment of heart disease or cardiac injury |
| Midbrain progenitor cells | Induce production of dopaminergic neurons | Treatment of neurodegenerative disease |
| Neural crest cells | Induce production of oligodendrocytes | Treatment of familial dysautonomia |
|  | Induce production of melanocytes | Treatment of pigment cell disorders |
|  | Stimulate enteric gliogenesis | Treatment of neurodegenerative disease |
|  | Induce neurogenesis | Treatment of neurodegenerative diseases |
| Neural progenitor cells | Induce astrocyte development | Treatment of neurodegenerative disease or nerve, brain or spinal cord injury |
|  | Induce neurogenesis and neurite outgrowth |  |
| Neural stem cells | Induce neurogenesis Induce astrocyte development | Treatment of neurodegenerative disease or nerve, brain or spinal cord injury |
| Oligodendrocyte progenitor cells | Induce serum-mediated astrocyte differentiation | Treatment of neural or spinal cord injury |
|  | Induce remyelination of axons and improve locomotor function |  |
| Outer root sheath cells | Maintain hair follicle homeostasis | Treatment of aberrant hair growth |
| Satellite cells | Induce muscle differentiation and fusion | Treatment of muscle injury or disease |
| Skeletal muscle cell progenitors | Induce skeletal muscle cell differentiation | Repair of the muscle following traumatic injury or surgery |

For the purposes of the present invention, "prevention" or "preventing" includes inhibiting the onset of a disease in a subject or patient which may be at risk and/or predisposed to the disease but does not yet experience or display any or all of the pathology or symptomatology of the disease, and/or slowing the onset of the pathology or symptomatology of a disease in a subject or patient which may be at risk and/or predisposed to the disease but does not yet experience or display any or all of the pathology or symptomatology of the disease.

"Treatment" or "treating" includes inhibiting a disease in a subject or patient experiencing or displaying the pathology or symptomatology of the disease (e.g., arresting further development of the pathology and/or symptomatology), ameliorating a disease in a subject or patient that is experiencing or displaying the pathology or symptomatology of the disease (e.g., reversing the pathology and/or symptomatology), and/or effecting any measurable decrease in a disease in a subject or patient that is experiencing or displaying the pathology or symptomatology of the disease.

An "effective amount," "therapeutically effective amount" or "pharmaceutically effective amount" means that amount which, when administered to a subject or patient for treating a disease, is sufficient to effect such treatment for the disease.

In addition to the above-described novel compounds, one or more of the following synthetic triterpenoids can be used in the methods of this invention. In particular embodiments, additional synthetic triterpenoids of use in the instant methods have the structure of Formula I, which includes hydrates, isomers, prodrugs or pharmaceutically acceptable salts of Formula I:

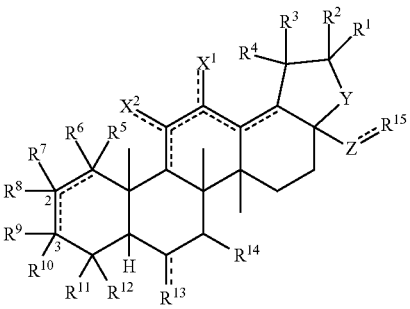

Formula I wherein,
$X^1$ and $X^2$ are independently
hydrogen, $OR^a$, $NR^aR^b$, or $SR^a$, wherein
$R^a$ is a hydrogen, cyano, $-CF_3$, nitro, amino, or substituted or unsubstituted heteroaryl group;
$R^b$ is hydrogen, hydroxyl, alkyl, aryl, aralkyl, acyl, alkoxy, aryloxy, acyloxy, alkylamino, arylamino, amido, or a substituted version of any of these groups;
or a substituent convertible in vivo to hydrogen;
provided that $R^a$ is absent when the atom to which it is bound is part of a double bond, further provided that when $R^a$ is absent the atom to which it is bound is part of a double bond;
Y is $CH_2$ or $CH_2-CH_2$;
Z is a covalent bond, $-C(=O)-$, alkanediyl, alkenediyl, alkynediyl, or a substituted version of any of these groups;
the dashed bonds can be independently present or absent;
$R^1$, $R^2$, $R^3$ and $R^4$ are each in dependently a hydrogen, hydroxyl, alkyl, substituted alkyl, alkoxy or substituted alkoxy group;
$R^5$, $R^6$, $R^7$, $R^8$, $R^9$ and $R^{10}$ are independently hydrogen, hydroxyl, halo, cyano, $-C\equiv CR^a$, $-CO_2R^a$, $-COR^a$, alkyl, alkenyl, alkynyl, aryl, aralkyl, heteroaryl, heteroaralkyl, acyl, alkoxy, aryloxy, acyloxy, alkylamino, arylamino, nitro, amino, amido, $-C(O)R^c$ or a substituted version of any of these groups, wherein
$R^c$ is hydrogen, hydroxy, halo, amino, hydroxyamino, azido or mercapto; or $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-dialkylamino, $C_1$-$C_{15}$-alkoxyamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-alkylsulfonylamino, $C_1$-$C_{15}$-amido, $C_1$-$C_{15}$-alkylsilyloxy, or substituted versions of any of these groups;
$R^5$ and $R^6$, $R^7$ and $R^8$, or $R^9$ and $R^{10}$ are independently taken together as =O;
$R^{11}$ and $R^{12}$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or $R^{11}$ and $R^{12}$ are taken together and are alkanediyl, alkenediyl, arenediyl, alkoxydiyl, alkenyloxydiyl, alkylaminodiyl, alkenylaminodiyl, or alkenylaminooxydiyl;

$R^{13}$ is hydrogen, hydroxy or oxo;

$R^{14}$ is hydrogen or hydroxyl; and $R^{15}$ is a hydrogen, hydroxyl, —$NR^dR^e$, cyano, halo, azido, phosphate, 1,3-dioxoisoindolin-2-yl, mercapto, silyl or —COOH group, substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkyloxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_1$-$C_{15}$-amido, $C_1$-$C_{15}$-alkylthio, $C_2$-$C_{15}$-alkenylthio, $C_2$-$C_{15}$-alkynylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, $C_1$-$C_{12}$-thioacyl, $C_1$-$C_{12}$-alkylsulfonyl, $C_2$-$C_{12}$-alkenylsulfonyl, $C_2$-$C_{12}$-alkynylsulfonyl, $C_6$-$C_{12}$-arylsulfonyl, $C_7$-$C_{12}$-aralkylsulfonyl, $C_1$-$C_{12}$-heteroarylsulfonyl, $C_1$-$C_{12}$-heteroaralkylsulfonyl, $C_1$-$C_{12}$-alkylsulfinyl, $C_2$-$C_{12}$-alkenylsulfinyl, $C_2$-$C_{12}$-alkynylsulfinyl, $C_6$-$C_{12}$-aryl sulfinyl, $C_7$-$C_{12}$-aralkylsulfinyl, $C_1$-$C_{12}$-heteroarylsulfinyl, $C_1$-$C_{12}$-heteroaralkylsulfinyl, $C_1$-$C_{12}$-alkylphosphonyl, $C_1$-$C_{12}$-alkylphosphate, $C_2$-$C_{12}$-dialkylphosphate, $C_1$-$C_{12}$-alkylammonium, $C_1$-$C_{12}$-alkylsulfonium, $C_1$-$C_{15}$-alkylsilyl, or a substituted version of any of these groups, a —$CO_2Me$, carbonyl imidazole, —CO-D-Glu(OAc)$_4$, —$CONH_2$, —$CONHNH_2$, —$CONHCH_2CF_3$, or —C(=O)-heteroaryl group, or Z and $R^{15}$ form a three to seven-membered ring, such that Z and $R^{15}$ are further connected to one another through one or more of —O— and alkanediyl, further wherein Z is —CH— and $R^{15}$ is —$CH_2$— or Z, $R^{15}$, and carbon numbers 13, 17 and 18 form a ring such that $R^{15}$ is bound to carbon 13, wherein Y is methanediyl or substituted methanediyl and $R^{15}$ is —O—, wherein $R^d$ and $R^e$ are independently hydrogen, hydroxyl, alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkoxy, thioacyl, alkylsulfonyl, alkenylsulfonyl, alkynylsulfonyl, arylsulfonyl, aralkylsulfonyl, heteroarylsulfonyl, or heteroaralkylsulfonyl, or a substituted version of any of these groups.

In certain embodiments, the bond between $C_2$ and $C_3$ in the A-ring is a double bond. In other embodiments, the bond between $C_2$ and $C_3$ in the A-ring is a single bond.

Definitions of alkyl, aryl, etc. are as defined for the substituents of Formula I and Formula II above. In addition, the term "alkylsulfonium" refers to the group —SRR', in which R and R' can be the same or different alkyl groups, or R and R' can be taken together to represent an alkanediyl. Non-limiting examples of alkylsulfonium groups include —SH(CH$_3$), —SH(CH$_2$CH$_3$), —SH(CH$_2$CH$_2$CH$_3$), —S(CH$_3$)$_2$, —S(CH$_2$CH$_3$)$_2$, —S(CH$_2$CH$_2$CH$_3$)$_2$, —SH(cyclopentyl), and —SH(cyclohexyl).

Exemplary compounds of use in the methods of the present invention include those shown below.

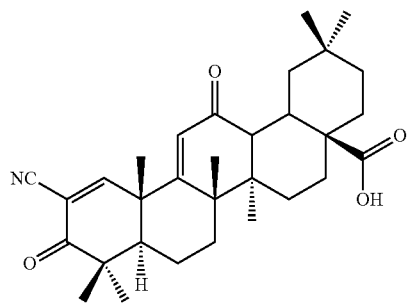

CDDO

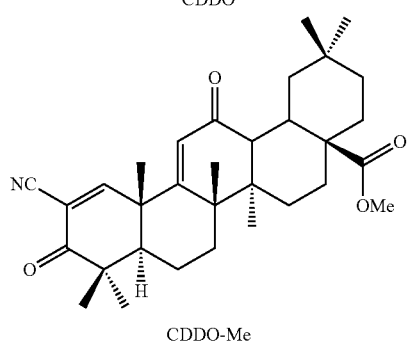

CDDO-Me

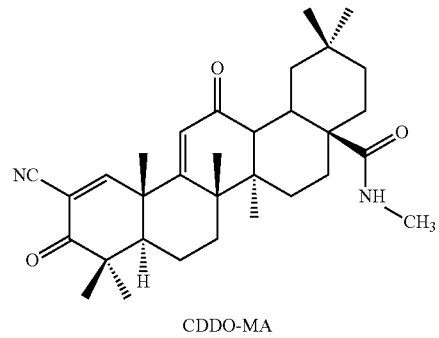

CDDO-MA

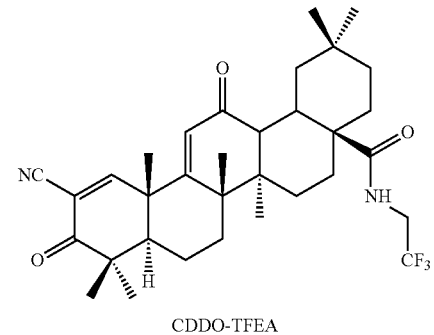

CDDO-TFEA

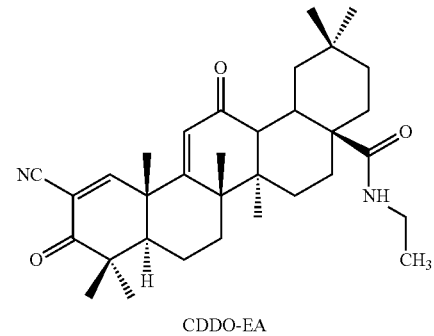

CDDO-EA

-continued

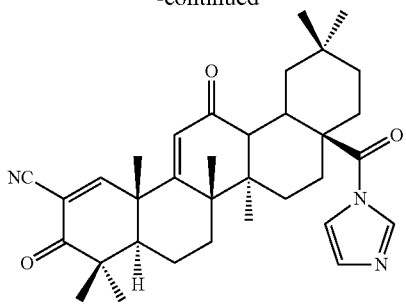

CDDO-Im

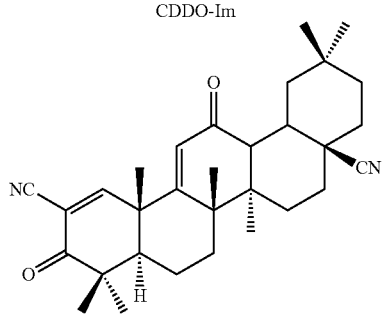

The synthetic triterpenoids of the present disclosure may be provided to a stem/progenitor cell ex vivo, in vitro or in vivo. When used under ex vivo or in vivo conditions, the stem/progenitor cell may be cultured under conventional cell culture conditions in the presence of a synthetic triterpenoid to induce the expression of one or more the genes described herein. As described herein, additional cell growth and differentiation factors may be employed to facilitate differentiation of the stem/progenitor cells. Stem/progenitor cells treated in such a manner can then be transplanted into a subject for therapeutic purposes.

The present invention also extends to articles coated with one or more synthetic triterpenoids, such as tissue culture dishes, multi-well plates (e.g., 1, 2, 4, 8, 24, 48, 96-wells, etc), PETRI-dishes, tissue culture flasks, fermentors, bioreactors, etc. for differentiating stem/progenitor cells. Such articles may be composed of any generally suitable material, such as a plastics material, for example polypropylene, or other materials such as glass, metal, etc. Suitable metals include mirror-polished metals, e.g., mirror-polished stainless steel.

When used in vivo, i.e., administered directly to a subject, the triterpenoid compounds of this invention may be administered in a pharmaceutical composition by various routes including, but not limited to, oral, subcutaneous, intravenous, or intraperitoneal administration (e.g. by injection). Depending on the route of administration, the active compound may be coated in a material to protect the compound from the action of acids and other natural conditions which may inactivate the compound. They may also be administered by continuous perfusion/infusion into a subject or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the synthetic triterpenoid in the required amount in an appropriate solvent with one or a combination of ingredients enumerated above, as required, followed by filtered sterilization. Generally, dispersions are prepared by incorporating the synthetic triterpenoid into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the synthetic triterpenoid) plus any additional desired ingredient from a previously sterile-filtered solution thereof.

The synthetic triterpenoid can be orally administered, for example, with an inert diluent or an assimilable edible carrier. The synthetic triterpenoid and other ingredients may also be enclosed in a hard or soft shell gelatin capsule, compressed into tablets, or incorporated directly into the patient's diet. For oral therapeutic administration, the synthetic triterpenoid may be incorporated with excipients and used in the form of ingestible tablets, buccal tablets, troches, capsules, elixirs, suspensions, syrups, wafers, and the like. The percentage of the synthetic triterpenoid in the compositions and preparations may, of course, be varied. The amount of the synthetic triterpenoid in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of synthetic triterpenoid calculated to produce the desired therapeutic effect in association with the required pharmaceutical carrier. The specification for the dosage unit forms of the invention are dictated by and directly dependent on (a) the unique characteristics of the synthetic triterpenoid and the particular therapeutic effect to be achieved, and (b) the limitations inherent in the art of compounding such a synthetic triterpenoid for the treatment of a selected condition in a patient.

The synthetic triterpenoid may also be administered topically to the skin, eye, or mucosa. Alternatively, if local delivery to the lungs is desired the synthetic triterpenoid may be administered by inhalation in a dry-powder or aerosol formulation.

In yet another embodiment, the synthetic triterpenoid can be administered as a coating on an article for implantation. Such articles include polymer scaffolds containing stem/progenitor cells, stents, shunts, and the like.

Active compounds are administered at a therapeutically effective dosage sufficient to treat a condition associated with a given patient. For example, the efficacy of a synthetic triterpenoid can be evaluated in an animal model system that may be predictive of efficacy in treating the disease in humans, such as the model systems described herein. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans.

The actual dosage amount of a synthetic triterpenoid of the present disclosure or composition comprising a synthetic triterpenoid of the present disclosure administered to a patient may be determined by physical and physiological factors such as age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. In other non-limiting examples, a dose may also comprise from about microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Single or multiple doses of the synthetic triterpenoids are contemplated. Desired time intervals for delivery of multiple doses can be determined by one of ordinary skill in the art employing no more than routine experimentation. As an example, patients may be administered two doses daily at approximately 12 hour intervals. In some embodiments, the synthetic triterpenoid is administered once a day.

The synthetic triterpenoid may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the synthetic triterpenoid may taken orally and that the timing of which is or is not dependent upon food intake. Thus, for example, the synthetic triterpenoid can be taken every morning and/or every evening, regardless of when the patient has eaten or will eat.

The invention is described in greater detail by the following non-limiting examples.

EXAMPLE 1

Materials and Methods

Reagents. The synthesis of the triterpenoids has been described (Liby, et al. (2007) *Nat. Rev. Cancer* 7:357-69; Sporn, et al. (2011) *J. Nat. Prod.* 74:537-45). All other chemicals were from Sigma-Aldrich.

Calvarial Organ Cultures. Details have been published previously (Garrett, et al. (2003) *J. Clin. Invest.* 111:1771-82). Calvaria were cultured in BGJ medium supplemented with 1 mg/mL of bovine serum albumin (Cohn fraction V), 100 U/ml each of penicillin/streptomycin, and 0.292 mg/mL of glutamine. On Day 1, the calvaria were treated with synthetic oleanane triterpenoids. On Day 4, the medium was replaced with fresh medium, again containing synthetic oleanane triterpenoids. On Day 7, calvaria were collected, either stored at −80° C. for further RNA analysis or fixed in 10% buffered formalin for 24 hours and transferred to 80% ethanol for histologic analysis.

Histologic Analysis of Calvaria. After fixation for hours, calvaria were decalcified in EDTA, embedded in paraffin and sectioned at 4 µm. Sections were stained either with modified hematoxylin and eosin (H&E) or with toluidine blue (1% in 70% ethanol for 20 minutes, followed by destaining in 70%, 90% and 100% ethanol for 15 seconds), placed in xylene twice, and then mounted. Procedures for immunofluorescence staining have been described (Medici, et al. (2010) *Nat. Med.* 74:537-45). Primary antibodies against collagen type II (AB746P, Millipore), were used at 1:100 dilution; ALEX- FLUOR secondary antibodies (Invitrogen) at 1:200 dilution. For nuclear staining, To-PRO-3 Iodide (T3605, Invitrogen) was used.

Bone Marrow-Derived Stem Cell Culture and Immunoblotting. Human bone marrow-derived stromal cells, which contain a population of responsive mesenchymal stem cells (ScienCell Research Laboratories), were grown in mesenchymal stem cell medium (ScienCell Research Laboratories). Cells were serum-starved 24 hours prior to all experimental conditions. Immunoblotting was performed using the following antibodies at concentrations (and using protocols) recommended by the respective manufacturers: SOX9 (sc-20095, Santa Cruz Biotechnology), collagen IIα1 (sc-7764 and sc-28887, Santa Cruz), aggrecan (ab3778 and ab36861, Abcam), BMP-2 (ab14933, Abcam), phospho-Smad5 (9516, Cell Signaling Technology), Smad5 (9517, Cell Signaling Technology), β-actin (A1978, SigmaeAldrich). HRP-conjugated IgG TRUEBLOT reagents (18-8814, eBioscience) were used at a dilution of 1:1000.

Quantitative RT-PCR (gRT-PCR). Detailed procedures for qRT-PCR are known in the art (Lee, et al. (2006) Biochem. Pharmacol. 72:332-43). In brief, 30 ng of RNA was reverse transcribed to cDNA using the random primers and Applied Biosystems' High Capacity cDNA Archive Kit in a 96-well format MASTERCYCLER Gradient from EPPENDORF. Subsequently, cDNA was amplified with ASSAYS-ON-DEMAND Products containing two gene specific primers and one TAQMAN MGB probe (6-FAM dye-labeled) using the TAQMAN Universal PCR Master Mix in an ABI PRISM 7000 Sequencing Detector (Applied Biosystems). All labeled primers were obtained from Applied Biosystems.

EXAMPLE 2

Synthesis of Triterpenoids

The triterpenoids of the invention can be generally produced from natural compounds such as oleanolic acid, ursolic acid, betulinic acid, or hederagenin, or derivatives thereof that include additional A and/or C ring modifications. Synthesis of the compounds can be achieved using any conventional method of synthesizing similar triterpenoids such as CDDO or CDDO-Me. See, e.g., U.S. Pat. Nos. 6,326,507, 6,552,075, 6,974,801, 7,288,568, 7,863,327, 7,915,402, 7,943,778, 8,034,955, 8,071,632, 8,124,656, 8,124,799, 8,129,429 and WO 2009/146216.

As one example, triterpenoid compounds of the invention can be synthesized by (a) methylating the carboxylic acid group of a compound of Formula III to afford a methyl ester (Formula IV); oxidizing the hydroxyl group of a compound of Formula IV with an oxidizing agent to form a double bond in Ring A (Formula V), epoxidating Ring C of the enone to form an epoxide, and forming a C-ring enol and halogenating the A-ring enone to yield a compound of Formula VI (Scheme 1)

SCHEME 1

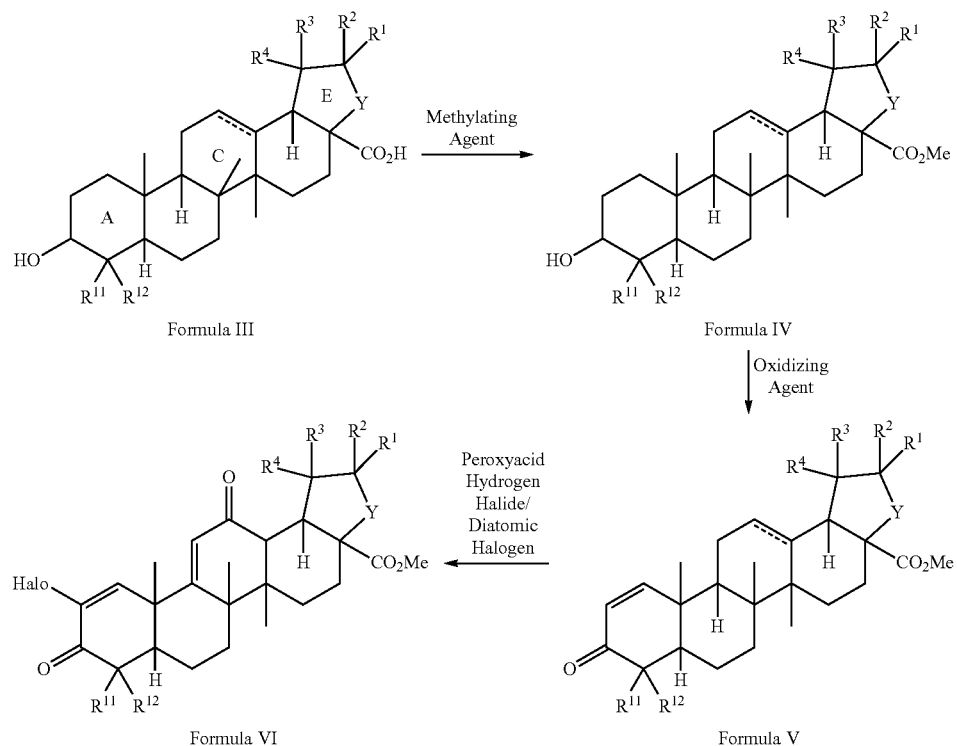

According to this example, the methylating agent is an electrophilic methyl source including, but not limited to iodomethane, dimethyl sulfate, dimethyl carbonate, diazomethane, or with methylating reagents such as methyl triflate or methyl fluorosulfonate, optionally in the presence of a base such as $K_2CO_3$ or $Li_2CO_3$. Further, the oxidizing agent can be an iodine oxidizing agent such as o-iodoxybenzoic acid (IBX)(Nicolaou, et al. (2002) J. Am. Chem. Soc. 124: 2245-2258), diacetoxyiodobenzene (DAIB), fluorous DAIB (F-DAIB), Dess-Martin-Periodinane (DMP), or a stabilized formulation of IBX (SIBX; Ozanne, et al. (2003) Org. Lett. 5:2903) in one or a combination of suitable solvents such as DMSO and phenyl fluoride (fluorobenzene). Furthermore, epoxidation of Ring C can be carried out with an oxidant such as a peroxyacid, e.g., meta-chloroperoxybenzoic acid (mCPBA), peroxyacetic acid, or potassium peroxymonosulfate (Oxone). Acid catalyzed opening of the epoxide and bromination of the A Ring can be achieved with a hydrogen halide such as (HBr or HI) and a diatomic halogen molecule such as $Br_2$ or $I_2$.

As used in the context of the present invention, Formula III includes naturally occurring starting materials such as oleanolic acid, ursolic acid, betulinic acid, or hederagenin, or derivatives thereof.

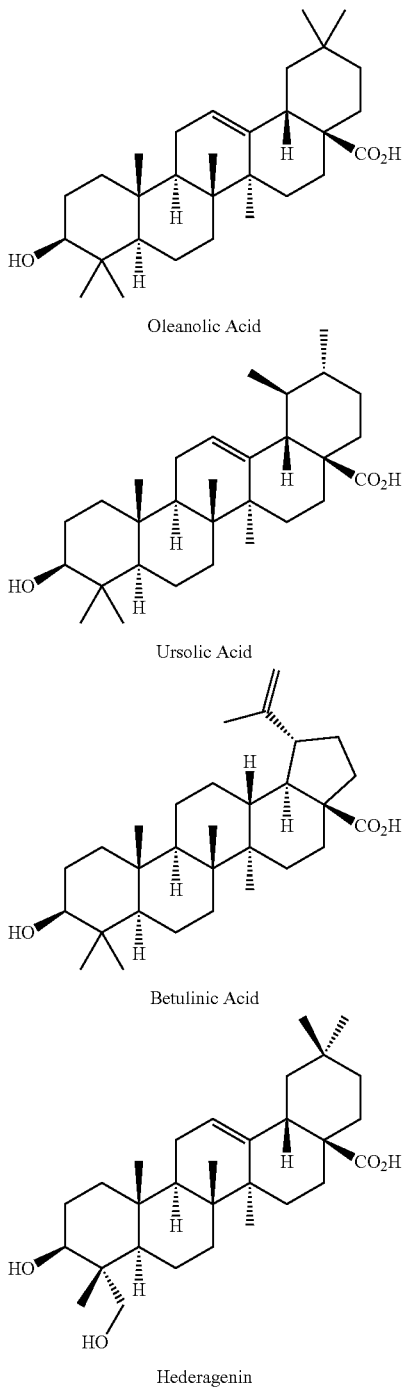

Oleanolic Acid

Ursolic Acid

Betulinic Acid

Hederagenin

As a specific example of using this synthetic method in the synthesis of triterpenoids, CDDO-Me was synthesized from oleanolic acid. As shown in Scheme 2, the natural triterpenoid oleanolic acid (1) was used as the starting material in the synthesis of CDDO-Me. The method commences with methylation of the carboxylic acid of oleanolic acid (1) to afford methyl ester 2 in quantitative yield. With ester 2, activation of the A-ring is fulfilled by 2-iodoxybenzoic acid-mediated two-fold oxidation to give enone 3. Epoxidation with meta-chloroperoxybenzoic acid, followed by direct C-ring enolization and A-ring enone bromination with bromine and hydrobromic acid, affords key intermediate 4. With bromide 4 in hand, a cross-coupling reaction with copper cyanide provides CDDO-Me (5) (Scheme 2). Intermediate 4 was prepared in high yield and few overall steps, thereby providing a base compound for development of the analogs and derivatives described herein.

SCHEME 2

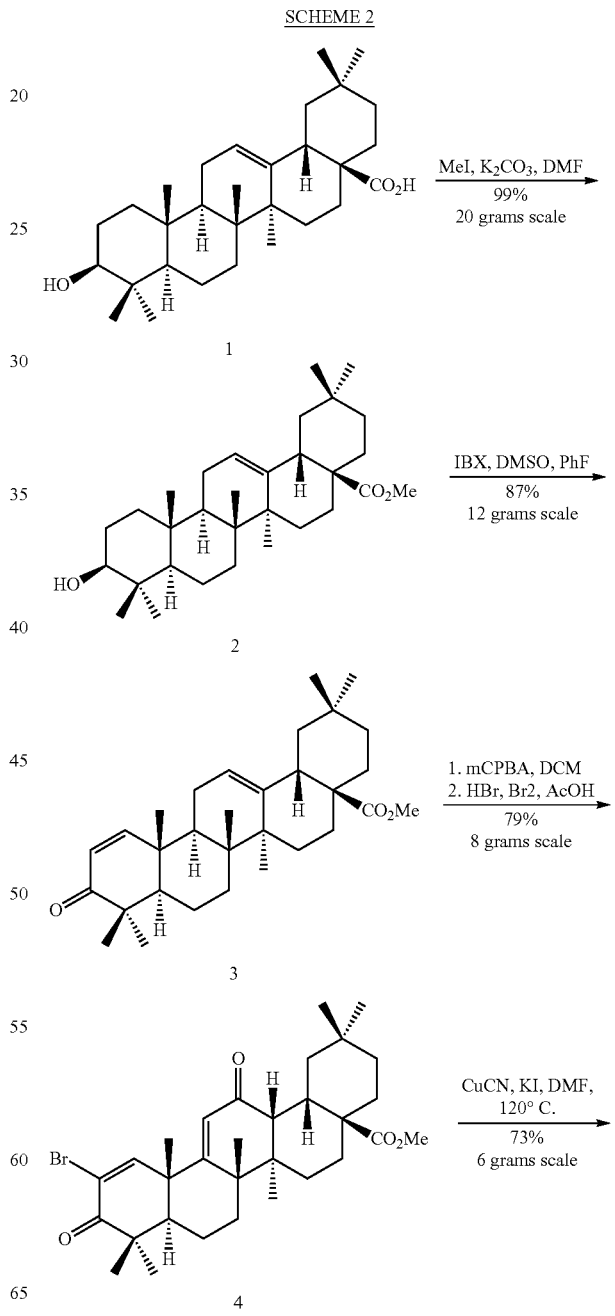

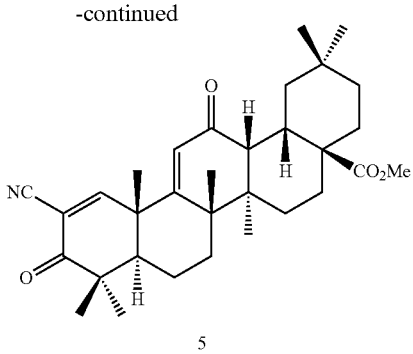

5

Unless otherwise specified, the reagents used in the instant methods are conventionally known in the art. For example, MeI refers to methyl iodide, DMF refers to dimethylformamide, IBX is 2-iodoxybenzoic acid, DMSO is dimethyl sulfoxide, PhF is phenyl fluoride, mCPBA refers to meta-chloroperoxybenzoic acid, HBr is hydrogen bromide, DCM is dichloromethane, AcOH is acetic acid, and CuCN is copper cyanide.

EXAMPLE 3

Ring A Modifications

Given the reactivity of Ring A halogen, Formula VI serves as a substrate for the synthesis of the triterpenoid derivatives of the invention. For example, contact of a compound of Formula VI with a cyanide ion source such as $K_4[Fe(CN)_6]$ KCN, NaCN, ZnCN, CuCN, $(CH_3)_2C(—OH)CN$ or TMSCN results in the displacement of the aromatic halide with a cyanide ion. In other embodiments, the compound of Formula VI can be reacted with a wide variety of reagents to replace the halogen on Ring A. For example, the compound of Formula VI can be aminated or coupled or cross-coupled with an alkyl, alkenyl, alkynyl or aryl group to provide a variety of substituents on Ring A. For example, Formula VI can be aminated via Buchwald-Hartwig amination (Buchwald & Muci (2002) *Top. Curr. Chem.* 219:133-209; Hartwig (1999) *Pure Appl. Chem.* 71:1417; Buchwald & Yang (1999) *J. Orgmet. Chem.* 576:125; Hartwig (1998) *ACIEE* 37:2046; Hartwig (1998) *Acc. Chem. Res.* 31:852; Buchwald et al. (1998) *Acc. Chem. Res.* 31:805) to provide amides and amines 6 ($R^{16}$=H and $R^{17}$=H or CHO). Moreover, when 6 is a formamide ($R^{16}$=H and $R^{17}$=CHO), isonitrile 7 can be readily synthesized under mild conditions (Porcheddu, et al. (2005) *J. Org. Chem.* 70:2361-3). In addition, Sonogashira coupling (Sonogashira, et al. (1975) *Tetrahedron Lett.* 16:4467-70) provides alkynes 8 and 10. Likewise, Suzuki (Miyuara, et al. (1979) *Tetrahedron Lett.* 20:3437-40; Miyaura & Suzuki (1979) *Chem. Comm.* 19:866-7; Miyaura & Suzuki (1995) *Chem. Rev.* 95:2457-2483), Stille (Kosugi, et al. (1977) *Chem. Lett.* 301; Milstein & Stille (1978) *J. Am. Chem. Soc.* 100:3636), and Negishi (King, et al. (1977) *J. Chem. Soc. Chem. Commun.* 19:683) cross-coupling reactions provide compounds having the structure of compound 9 and dimers such as compounds 10-17 are readily produced when the halogen of Formula VI is iodide.

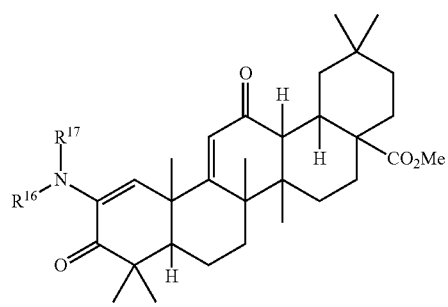

6

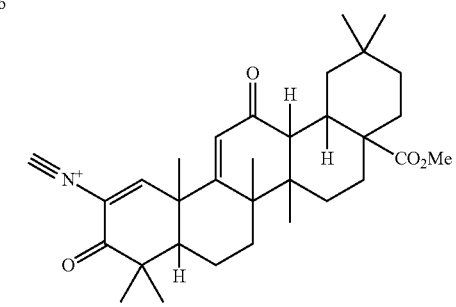

7

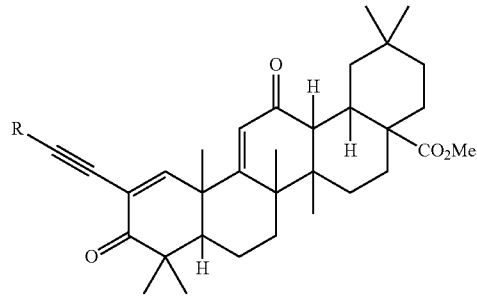

8
(R = alkyl, aryl, alkenyl, alkynyl)

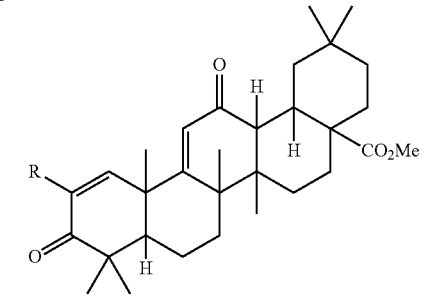

9
(R = alkyl, aryl, alkenyl, alkynyl)

-continued
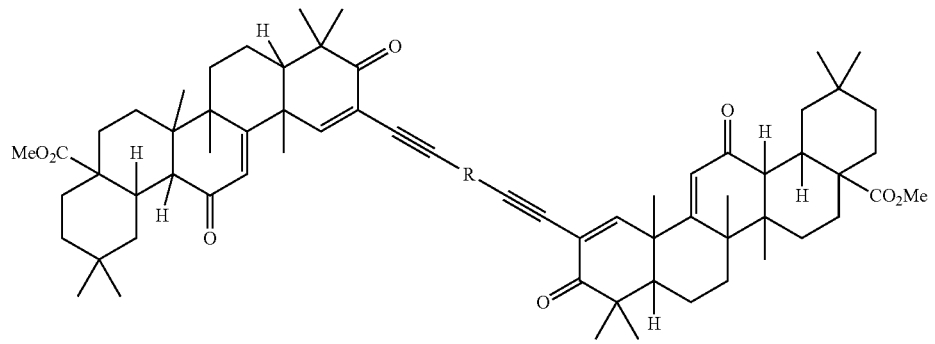
(R = alkyl, aryl, alkenyl, alkynyl)
10
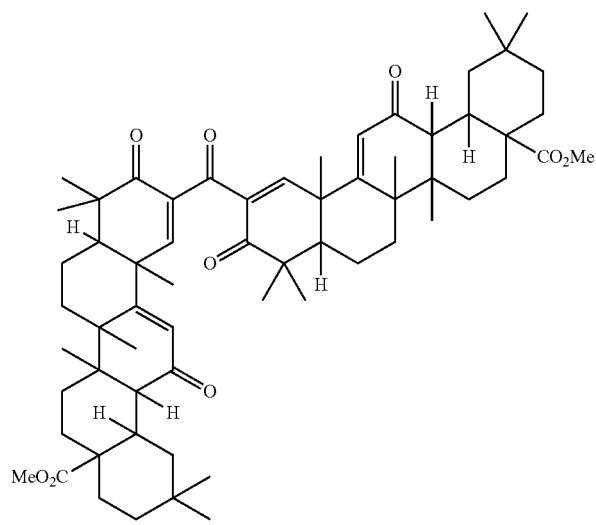
11
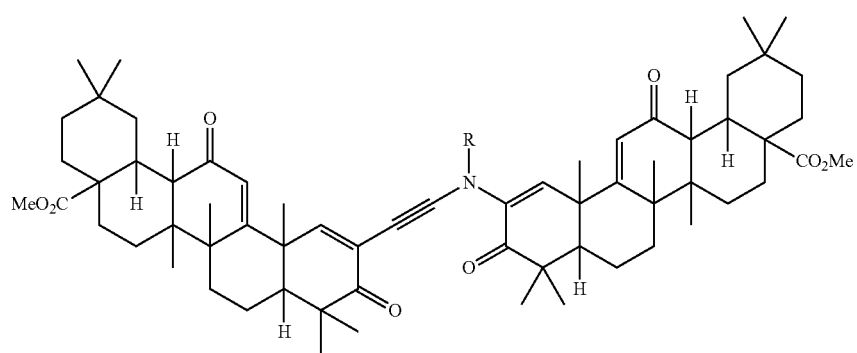
(R = H, alkyl, aryl, alkenyl, alkynyl)
12

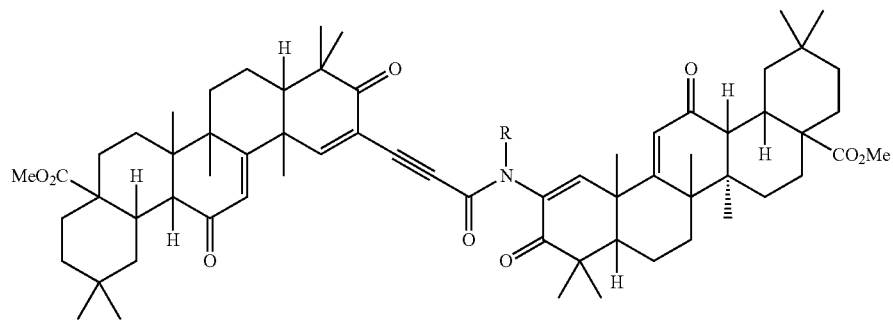
(R = H, alkyl, aryl, alkenyl, alkynyl)
13
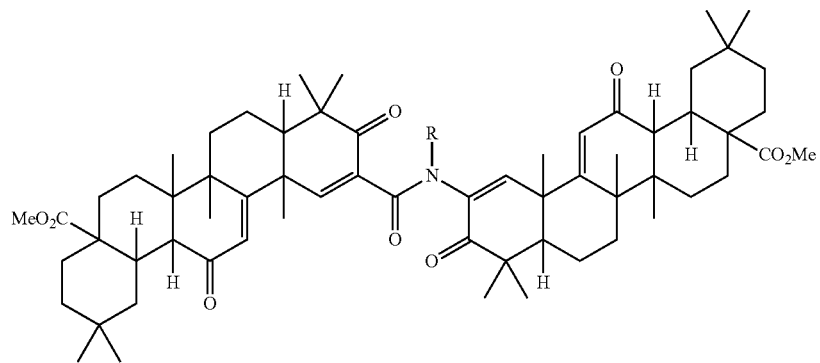
(R = H, alkyl, aryl, alkenyl, alkynyl)
14
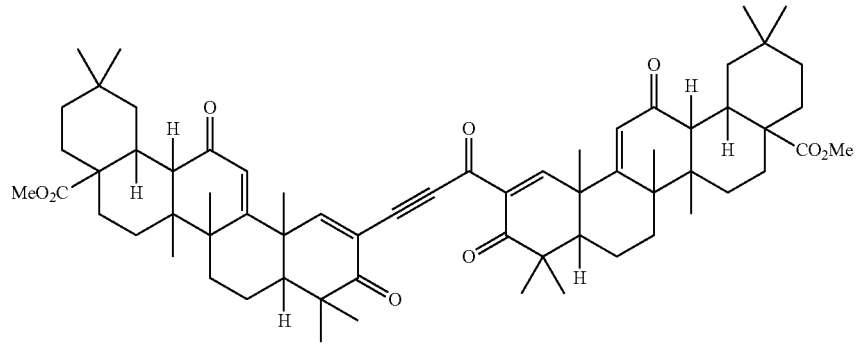
15
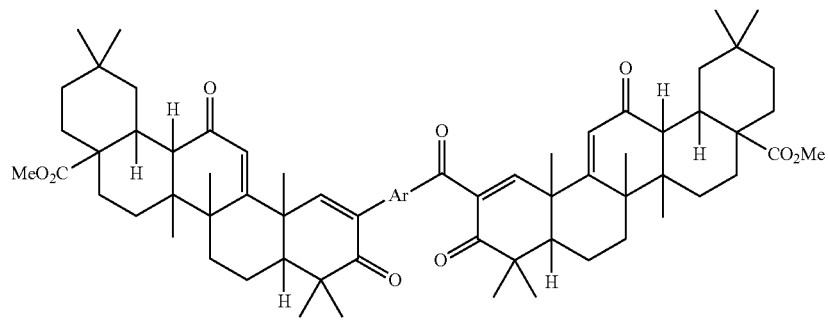
16

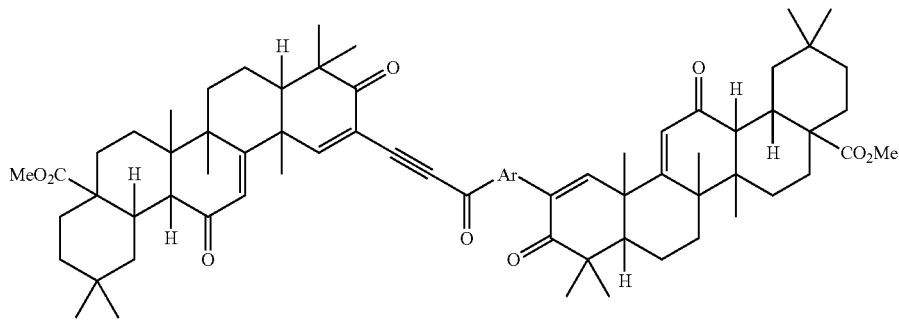

EXAMPLE 4

Derivatives with Modifications at C-17

Amides (Formula VI), ethers (Formula VII), and esters (Formula VIII and Formula IX) are readily obtained using the instant method in combination with techniques known in the art. See U.S. Pat. No. 6,974,801 and US 2008/0233195.

Formula VI

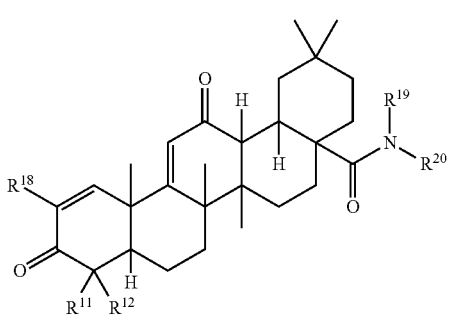

Formula VII

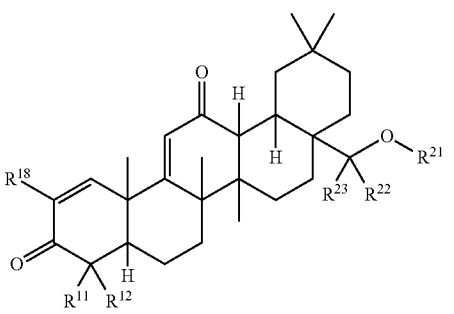

Formula VIII

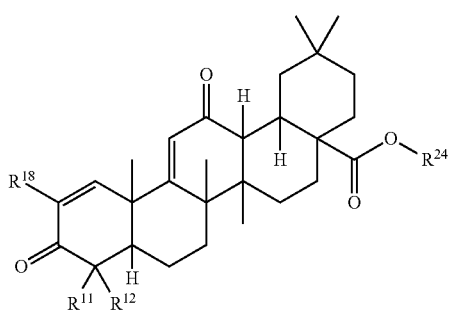

Formula IX

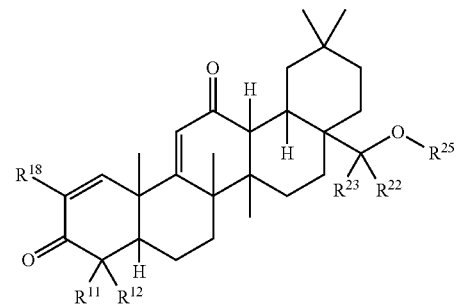

In accordance with Formulae VI-IX, $R^{11}$ and $R^{12}$ are as defined for Formula I;

$R^{18}$ is —OMs, —CH$_2$OMs, —C(=O)C≡CR$^a$, —C≡CCO$_2$R$^a$, —C≡CSO$_2$R$^a$, —C≡CC(=O)R$^a$, —SO$_2$R$^a$, =O or =CR$^c$R$^d$, wherein $R^d$ is hydrogen, halo, alkylthiyl, or substituted or unsubstituted alkylsulfonyl or alkylsulfonyl-O—;

$R^{22}$ and $R^{23}$ are independently a hydrogen, hydroxyl, halo, alkyl, nitro or amino group;

$R^{19}$, $R^{20}$, $R^{21}$, $R^{24}$ and $R^{25}$ are independently a hydrogen, hydroxyl, —NR$^f$Rg, cyano, halo, azido, phosphate, 1,3-dioxoisoindolin-2-yl, mercapto, silyl or —COOH group, substituted or unsubstituted versions of C$_1$-C$_{15}$-alkyl, C$_2$-C$_{15}$-alkenyl, C$_2$-C$_{15}$-alkynyl, C$_6$-C$_{15}$-aryl, C$_7$-C$_{15}$-aralkyl, C$_1$-C$_{15}$-heteroaryl, C$_2$-C$_{15}$-heteroaralkyl, C$_1$-C$_{15}$-acyl, C$_1$-C$_{15}$-alkoxy, C$_2$-C$_{15}$-alkenyloxy, C$_2$-C$_{15}$-alkynyloxy, C$_1$-C$_{15}$-aryloxy, C$_7$-C$_{15}$-aralkyloxy, C$_1$-C$_{15}$-heteroaryloxy, C$_2$-C$_{15}$-heteroaralkyloxy, C$_1$-C$_{15}$-acyloxy, C$_1$-C$_{15}$-alkylamino, C$_2$-C$_{15}$-alkenylamino, C$_2$-C$_{15}$-alkynylamino, C$_6$-C$_{15}$-arylamino, C$_7$-C$_{15}$-aralkylamino, C$_1$-C$_{15}$-heteroarylamino, C$_2$-C$_{15}$-heteroaralkylamino, C$_1$-C$_{15}$-amido, C$_1$-C$_{15}$-alkylthio, C$_2$-C$_{15}$-alkenylthio, C$_2$-C$_{15}$-alkynylthio, C$_6$-C$_{15}$-arylthio, C$_7$-C$_{15}$-aralkylthio, C$_1$-C$_{15}$-heteroarylthio, C$_2$-C$_{15}$-heteroaralkylthio, C$_1$-C$_{15}$-acylthio, C$_1$-C$_{12}$-thioacyl, C$_1$-C$_{12}$-alkylsulfonyl, C$_2$-C$_{12}$-alkenylsulfonyl, C$_2$-C$_{12}$-alkynylsulfonyl, C$_6$-C$_{12}$-arylsulfonyl, C$_7$-C$_{12}$-aralkylsulfonyl, C$_1$-C$_{12}$-heteroarylsulfonyl, C$_1$-C$_{12}$-heteroaralkylsulfonyl, C$_1$-C$_{12}$-alkylsulfinyl, C$_2$-C$_{12}$-alkenylsulfinyl, C$_2$-C$_{12}$-alkynylsulfinyl, C$_6$-C$_{12}$-aryl sulfinyl, C$_7$-C$_{12}$-aralkylsulfinyl, C$_1$-C$_{12}$-heteroarylsulfinyl, C$_1$-C$_{12}$-heteroaralkylsulfinyl, C$_1$-C$_{12}$-alkylphosphonyl, C$_1$-C$_{12}$-alkylphosphate, C$_2$-C$_{12}$-dialkylphosphate, C$_1$-C$_{12}$-alkylammonium, C$_1$-C$_{12}$-alkylsulfonium, C$_1$-C$_{15}$-alkylsilyl, or a substituted version of any of these groups, a —O—O$_2$Me, carbonyl imidazole, —CO—D-Glu(OAc)$_4$, —CONH$_2$, —CONHNH$_2$, —CONHCH$_2$CF$_3$, or —C(=O)-heteroaryl group.

EXAMPLE 5

CDDO-Me Derivatives with A-Ring Modifications

CDDO-Me derivatives within the scope of Formula I and containing A-Ring modifications are as follows.

Formula X

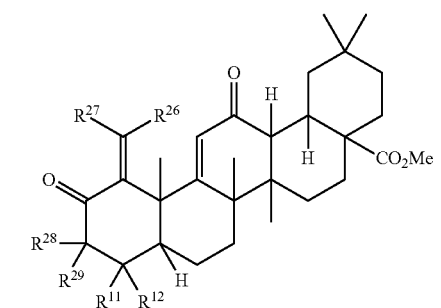

Formula XI

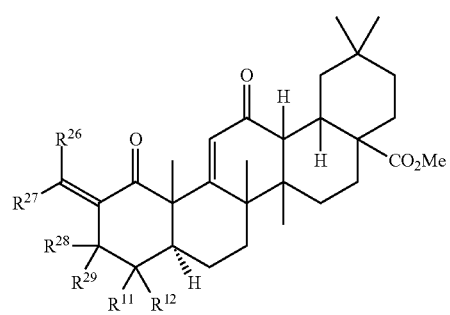

Formula XII

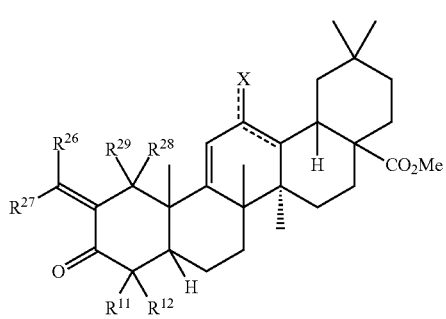

Formula XIII

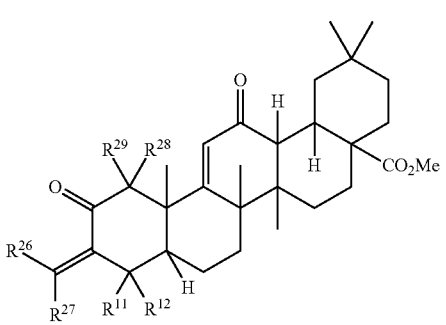

In accordance with Formulae X-XIII,
R$^{11}$ and R$^{12}$ are as defined for Formula I;
X is =O or —OMe;
dashed bonds are present or absent;

R$^{26}$ and R$^{27}$ are independently a hydrogen, halo (e.g., Cl or F), alkylthiyl, or substituted or unsubstituted alkylsulfonyl or alkylsulfonyl-O—;

R$^{28}$ and R$^{29}$ are independently —H, or together are =O.

Exemplary compounds of Formulae X-XIII include compounds 18-82:

18
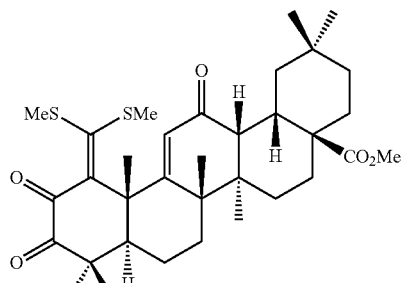

19
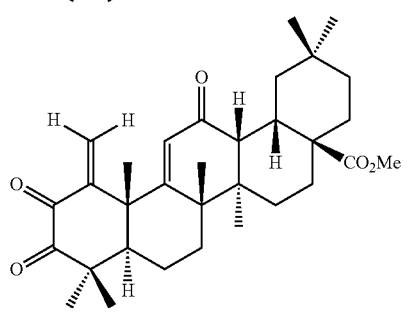

20
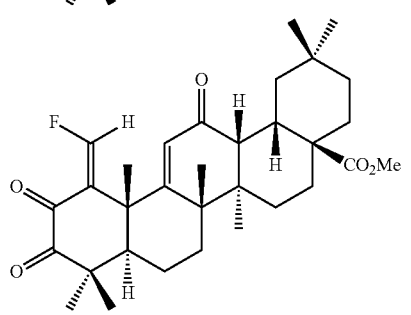

21
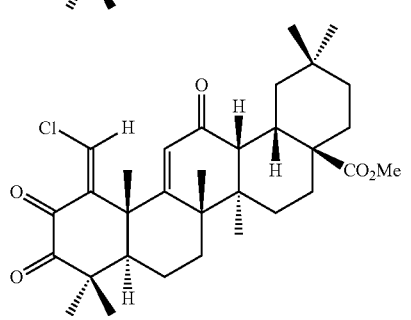

22
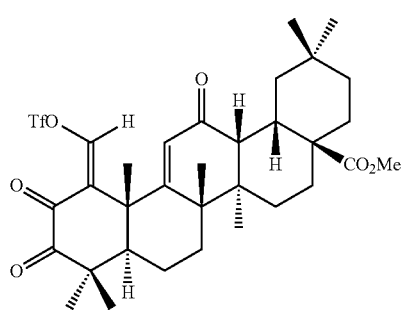

23
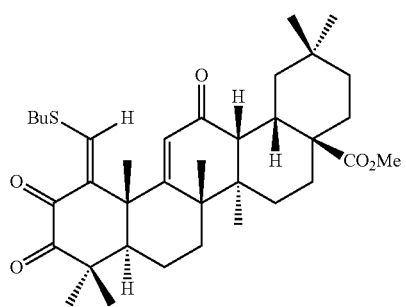
24
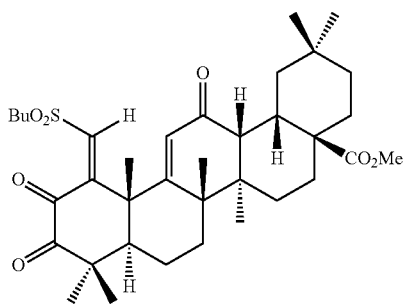
25
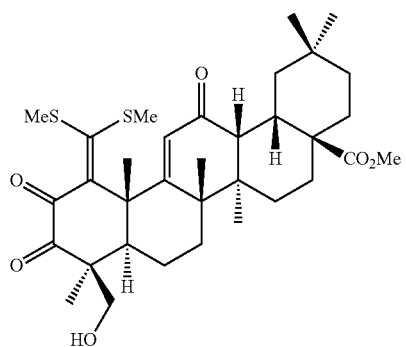
26
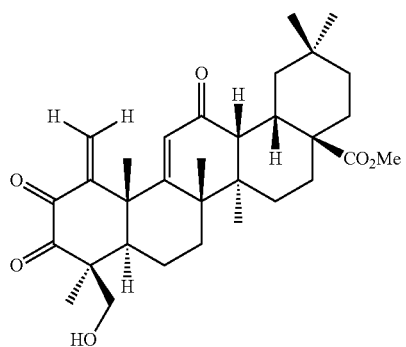
27
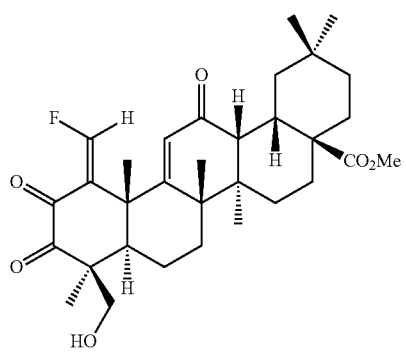
28
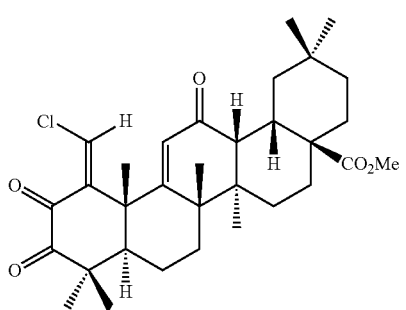
29
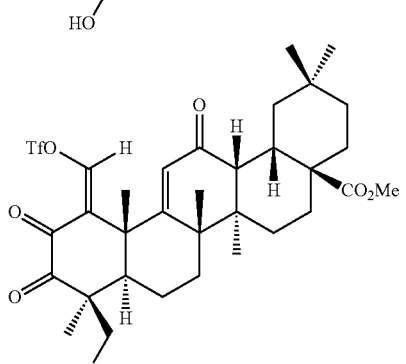
30
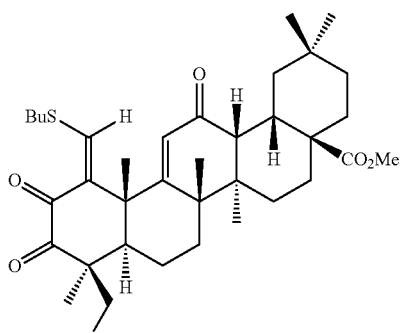
31
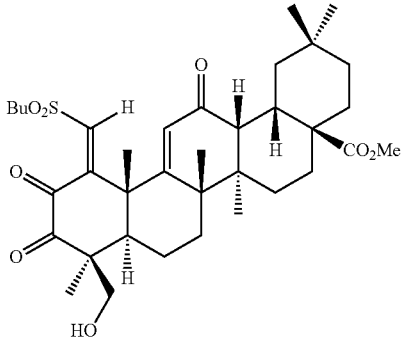
32
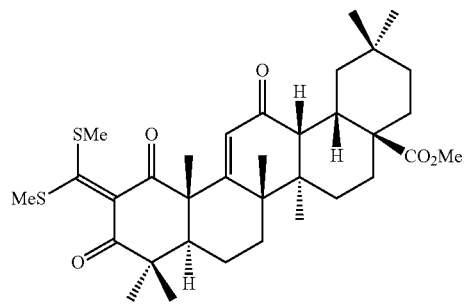

33
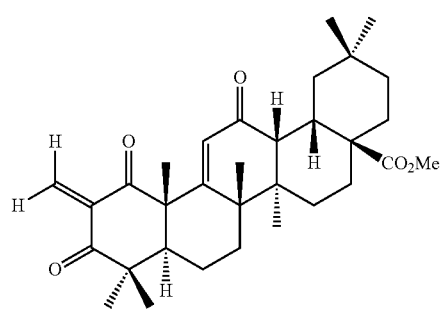
34
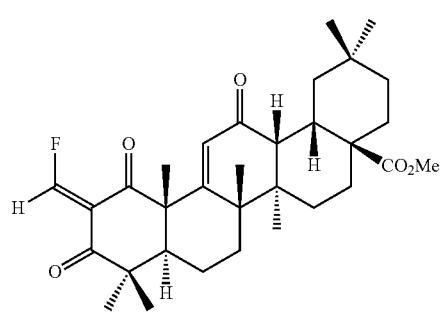
35
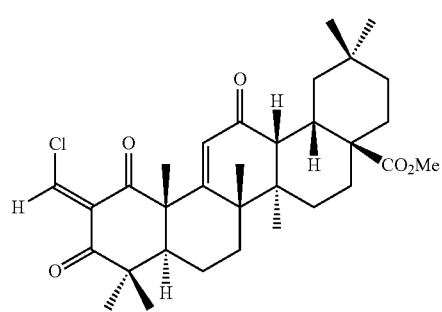
36
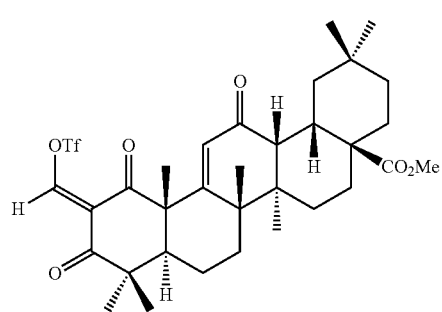
37
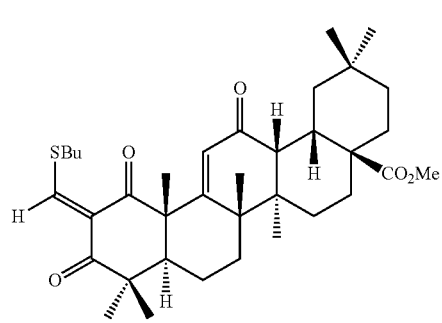
38
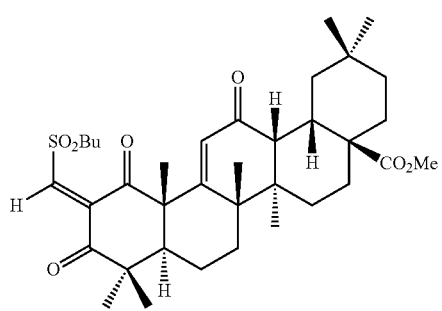
39
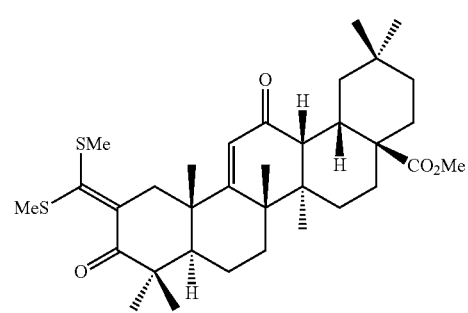
40
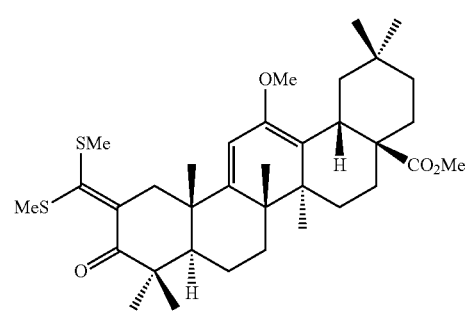
41
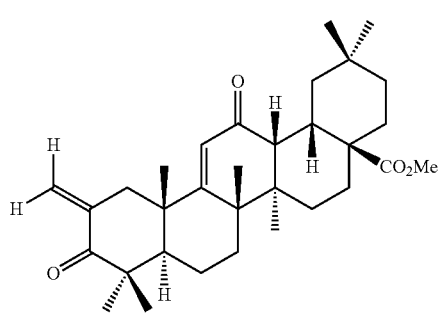
42
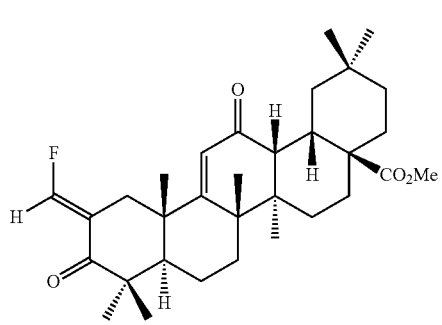

43
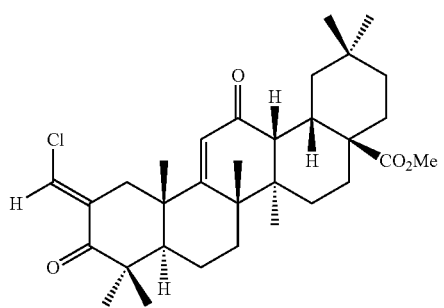
44
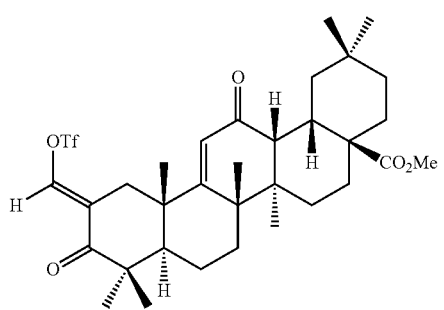
45
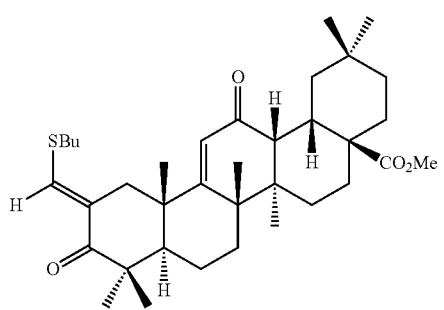
46
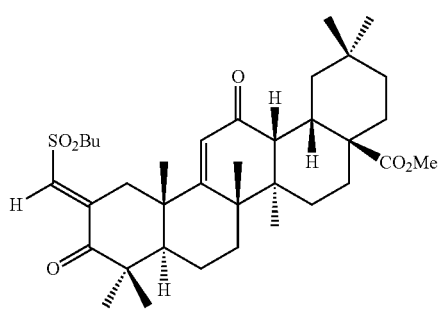
47
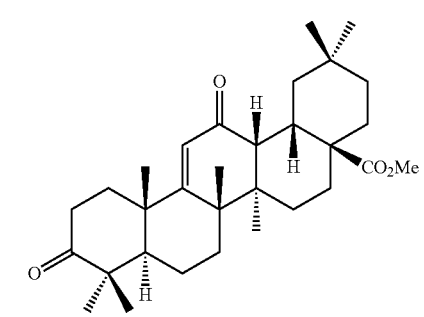
48
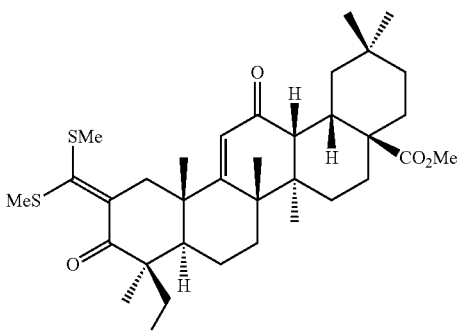
49
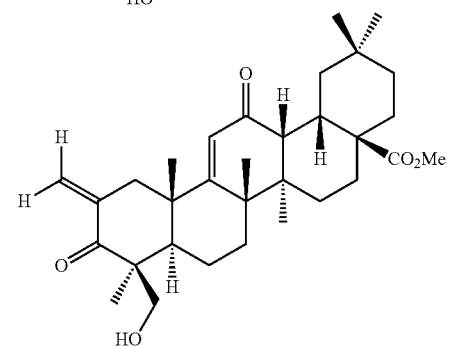
50
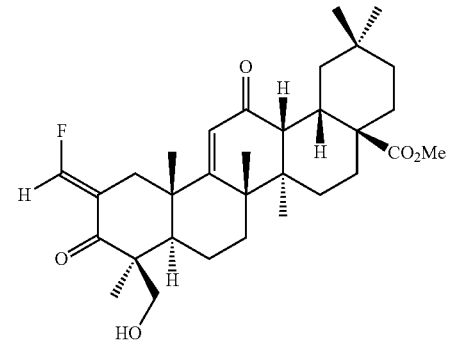
51
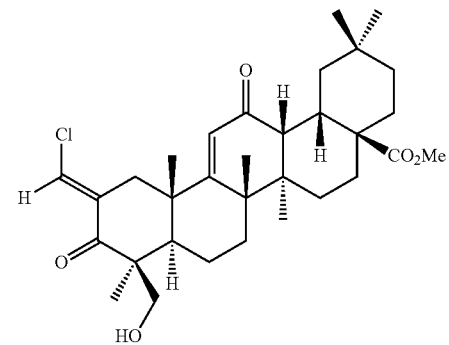
52
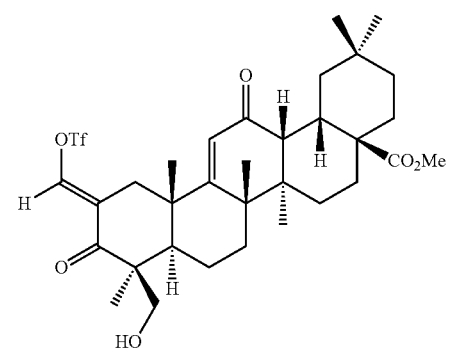

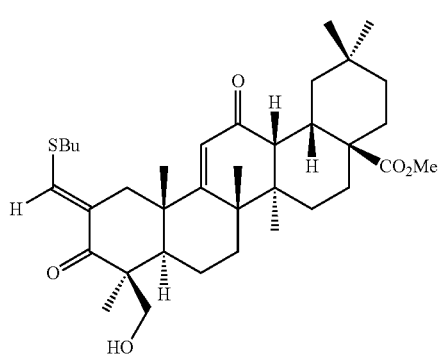
53
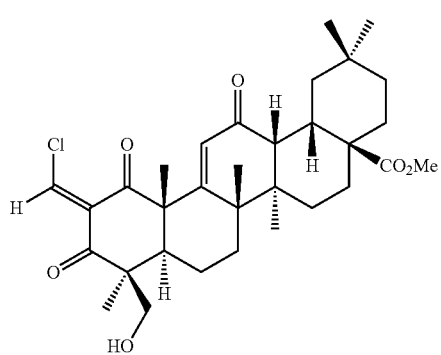
57
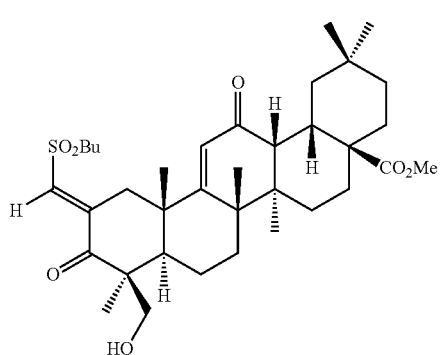
54
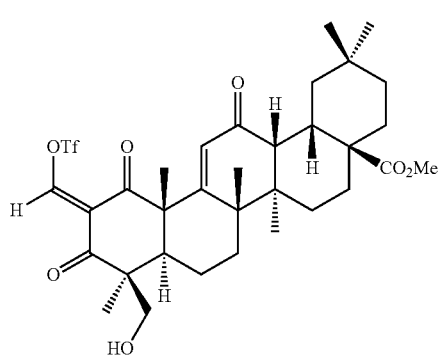
58
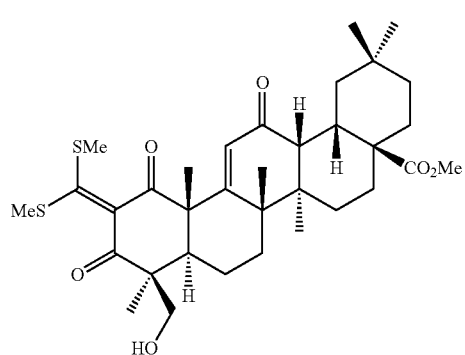
55
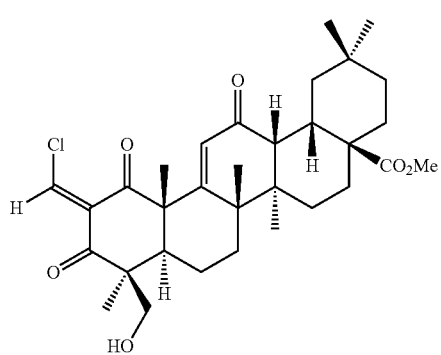
59
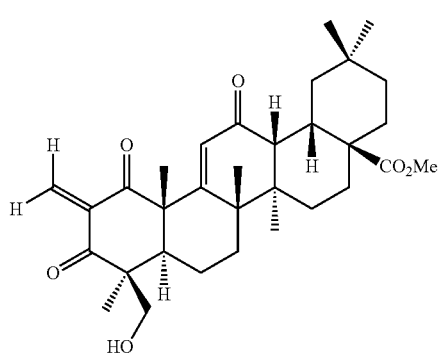
56
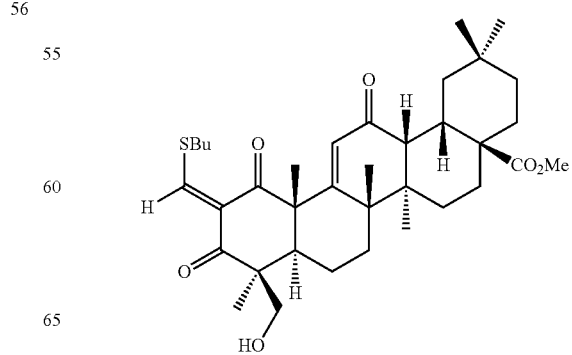
60

-continued

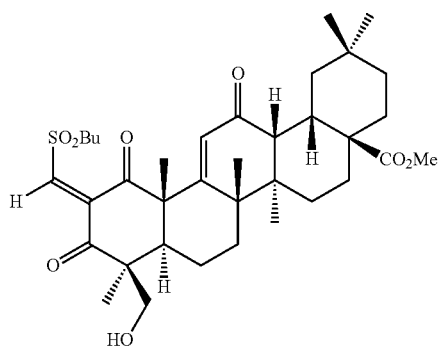
61

EXAMPLE 6

Mesylate Derivatives of CDDO-Me

Mesylate derivatives of CDDO-Me of Formula XIV-XVI are also included with the scope of this invention.

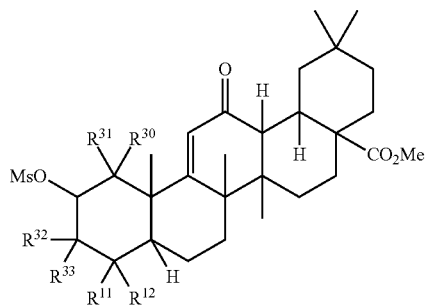
Formula XIV

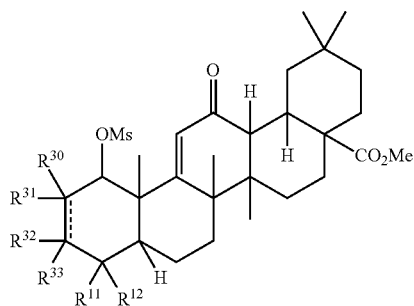
Formula XV

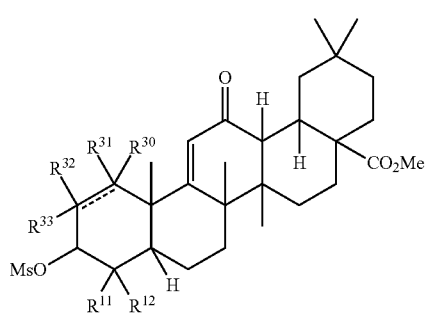
Formula XVI

In accordance with Formulae XIV-XVI:
$R^{11}$ and $R^{12}$ are as defined for Formula I;
$R^{30}$, $R^{31}$, $R^{32}$ and $R^{33}$ are each independently a hydrogen, cyano, —OMs, or —CH$_2$OMs group; or
$R^{30}$ and $R^{31}$ or $R^{32}$ and $R^{33}$ together are =CH$_2$; and dashed bonds are either present or absent.

Exemplary compounds of Formulae XIV-XVI include compounds 62-75:

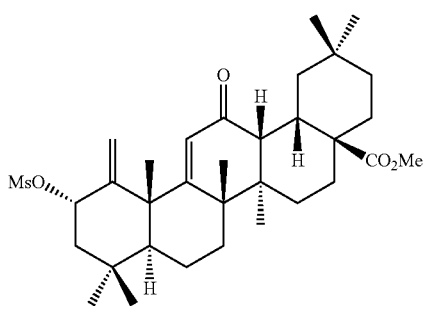
62

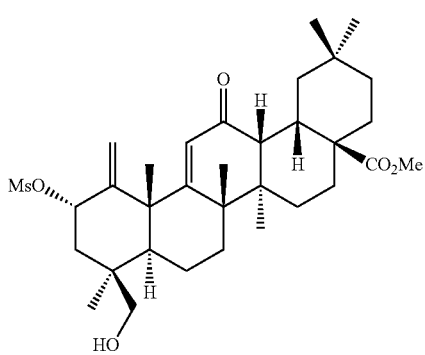
63

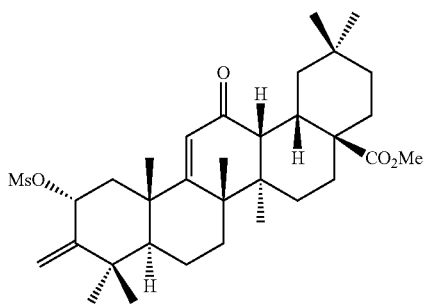
64

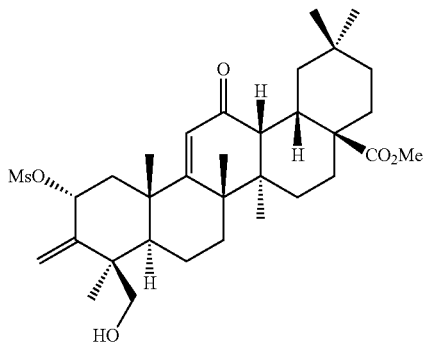
65

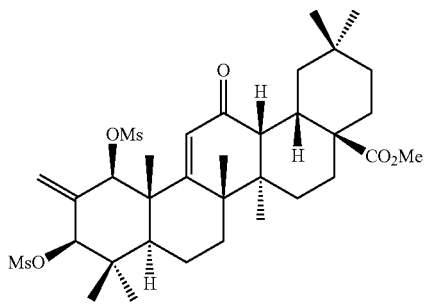
66

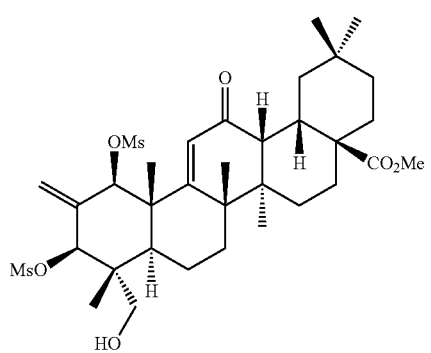
67
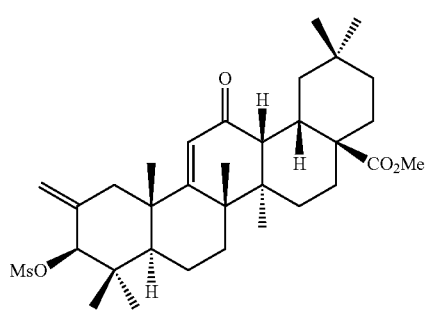
68
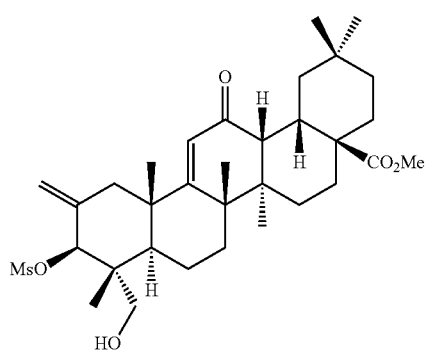
69
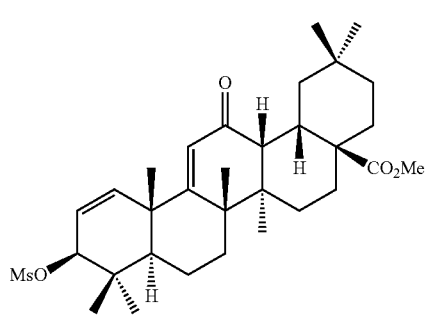
70
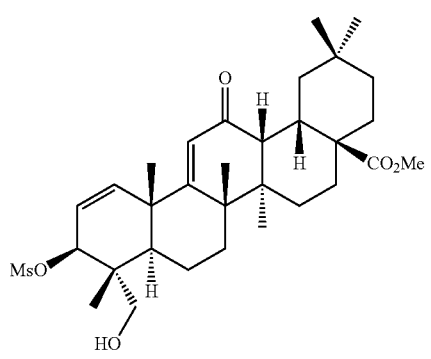
71
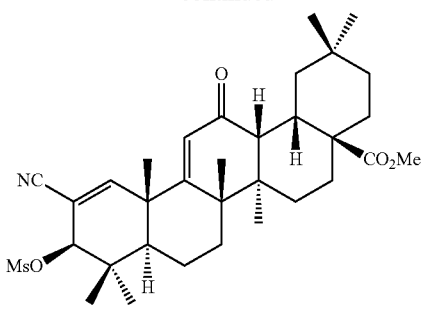
72
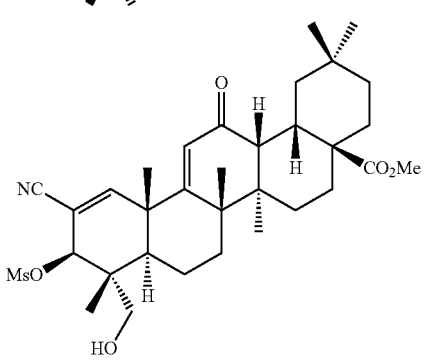
73
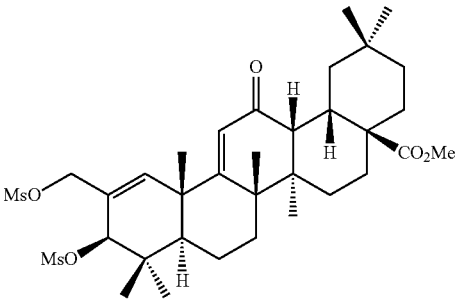
74
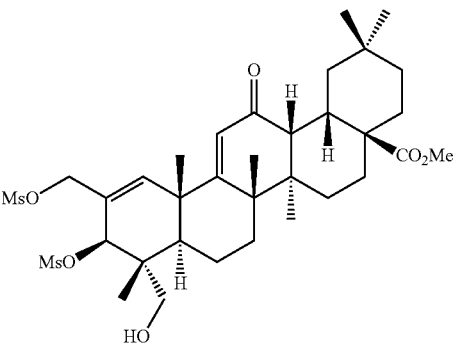
75
Mesylate derivatives having the structure of Formula XVII are also embodied by the present invention.
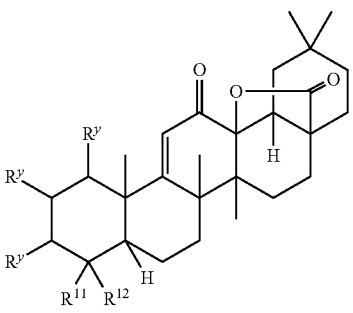
Formula XVII wherein $R^{11}$ and $R^{12}$ are as defined for Formula I; and at least one of $R^y$ is OMs and the remaining $R^y$ are a hydrogen, cyano, —OMs, —CH₂OMs, or =CH₂ group.

EXAMPLE 7

Gene Expression and Cellular Differentiation

For the results described here, more than 300 individual calvarial organ cultures were performed. The analysis presented herein indicated that both CDDO-Im and CDDO-EA have marked ability to induce chondrogenesis in newborn mouse calvaria. Because it is membranous bone, the newborn calvarium does not manifest the chondrogenic phenotype, except for a very thin margin at suture lines; care was taken to avoid using suture areas of calvaria in any of the analyses described below. Treatment with either triterpenoid (200 nM) for 7 days clearly had a profound chondrogenic effect on the calvaria. No new cartilage was seen on control sections stained with either H&E or toluidine blue. In contrast, the metachromatic toluidine blue purple staining was indicative of the ability of CDDO-Im and CDDO-EA to induce the formation of proteoglycans, such as aggrecan, which are characteristic of cartilage (Roughley (2001) *Arthritis Res.* 3:342-7). With toluidine blue, bone stained orthochromatically (blue).

With respect to dose-response to either synthetic oleanane, 200 nM appeared to be optimal. Treatment with 50 nM triterpenoid yielded only marginal induction of chondrogenesis, while treatment with 500 nM synthetic oleanane gave somewhat variable results. Treatment with 1 mM triterpenoid was invariably toxic to the organ cultures. Results with 200 nM CDDO-Im and CDDO-EA were obtained in at least three sets of replicate experiments and immunohistochemistry showed that CDDO-Im and CDDO-EA (200 nM) both induced the formation of type II collagen (collagen IIα1), which was not seen in the control sections.

In addition to the histologic analysis of the calvarial cultures, mechanistic aspects of the action of both CDDO-EA and CDDO-Im were investigated in the calvaria. After 7 days of culture, RNA was isolated from the calvaria and quantitative RT-PCR analysis was performed for more than 15 different markers, including: SOX9, collagen IIα1, all three isoforms of TGF-β, BMPs 2 and 4, BMP receptor II, Smads 3, 4, 6, and 7, tissue inhibitors of metalloproteinases (TIMP-1 and TIMP-2), and matrix metalloproteinase-9 (MMP-9). Tables 2 and 3 show that essentially all of these markers (except MMP-9) were significantly up-regulated by both triterpenoids, when the calvaria were treated at either the 200 or the 500 nM dose. The 50 nM dose was generally ineffective. In contrast, both triterpenoids were strong inhibitors of the expression of MMP-9; CDDO-EA (200 nM) caused almost 80% inhibition of the expression of this metalloproteinase, which is known to be involved in the degradation of cartilage (Shinoda, et al. (2008) *J. Biol. Chem.* 283:24632-9).

TABLE 2

| | CDDO-Im | | |
|---|---|---|---|
| Gene | 50 nM | 200 nM | 500 nM |
| SOX9 | 1.26 ± 0.08 | 1.33 ± 0.05 | 1.83 ± 0.13** |
| COL2A1 | 1.45 ± 0.09 | 1.32 ± 0.23 | 1.72 ± 0.39 |
| TGF-β1 | 0.96 ± 0.07 | 1.08 ± 0.12 | 1.46 ± 0.12* |
| TGF-β2 | 1.17 ± 0.05 | 1.15 ± 0.09 | 1.17 ± 0.10 |
| TGF-β3 | 1.30 ± 0.07 | 1.52 ± 0.16** | 1.66 ± 0.13** |
| BMP-2 | 1.17 ± 0.07 | 1.60 ± 0.19 | 3.14 ± 0.53** |
| BMP-4 | 0.97 ± 0.05 | 0.98 ± 0.06 | 1.35 ± 0.22 |
| BMPRII | 1.09 ± 0.06 | 1.22 ± 0.11 | 1.46 ± 0.14* |
| Smad3 | 0.97 ± 0.07 | 0.90 ± 0.05 | 1.35 ± 0.19 |
| Smad4 | 0.96 ± 0.06 | 1.03 ± 0.09 | 1.26 ± 0.09 |
| Smad6 | 0.95 ± 0.05 | 1.23 ± 0.14 | 1.77 ± 0.19** |
| Smad7 | 1.05 ± 0.07 | 1.320.14 | 1.78 ± 0.18** |
| TIMP-1 | 1.43 ± 0.19 | 1.83 ± 0.18 | 3.00 ± 0.65** |
| TIMP-2 | 1.24 ± 0.10 | 1.67 ± 0.19 | 2.62 ± 0.29** |
| MMP-9 | 0.73 ± 0.16 | 0.44 ± 0.12** | 0.26 ± 0.03** |

TABLE 3

| | CDDO-ea | | |
|---|---|---|---|
| Gene | 50 nM | 200 nM | 500 nM |
| SOX9 | 1.64 ± 0.17 | 2.62 ± 0.33** | 3.12 ± 0.38** |
| COL2A1 | 4.12 ± 1.78* | 5.45 ± 1.13** | 3.18 ± 0.71 |
| TGF-β1 | 1.17 ± 0.09 | 1.47 ± 0.24* | 1.74 ± 0.17** |
| TGF-β2 | 1.36 ± 0.13* | 1.61 ± 0.11** | 1.88 ± 0.09** |
| TGF-β3 | 1.39 ± 0.07* | 1.56 ± 0.13** | 1.44 ± 0.11** |
| BMP-2 | 1.53 ± 0.20 | 2.52 ± 0.29** | 5.66 ± 0.67** |
| BMP-4 | 1.28 ± 0.12 | 1.47 ± 0.13 | 2.49 ± 0.35** |
| BMPRII | 1.50 ± 0.14* | 1.71 ± 0.19** | 2.24 ± 0.22** |
| Smad3 | 1.14 ± 0.12 | 1.35 ± 0.07 | 1.93 ± 0.16** |
| Smad4 | 1.06 ± 0.03 | 1.37 ± 0.12** | 1.89 ± 0.12** |
| Smad6 | 1.09 ± 0.04 | 1.77 ± 0.24** | 2.85 ± 0.31** |
| Smad7 | 1.28 ± 0.10 | 1.86 ± 0.19** | 3.06 ± 0.28** |
| TIMP-1 | 1.88 ± 0.34 | 2.85 ± 0.38** | 4.65 ± 0.38** |
| TIMP-2 | 1.78 ± 0.18* | 2.44 ± 0.31** | 4.09 ± 0.36** |
| MMP-9 | 0.49 ± 0.09** | 0.22 ± 0.03** | 0.19 ± 0.06** |

Further studies on mechanism were pursued in human bone marrow stem cell (BMSC) cultures. Western blot analysis showed that CDDO-Im and CDDO-EA (each 100 nM for 7 days) induced expression of the chondrocyte markers, SOX9, collagen type 2, and aggrecan, none of which were detectable in the control cultured stem cells. Furthermore, both triterpenoids (also at 100 nM) rapidly induced expression of both BMP-2 and its relevant signal transduction protein, phospho-Smad5 (P-Smad5), in these stem cells. BMP-2 is known to induce chondrogenic lineage development of human mesenchymal stem cells in culture (Schmitt, et al. (2003) *Differentiation* 71:567-77).

What is claimed is:

1. A triterpenoid compound having the structure of:

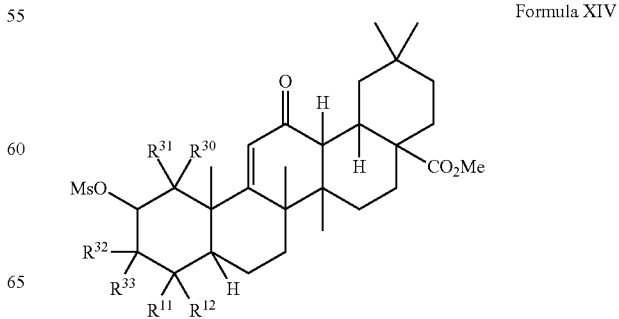

Formula XIV

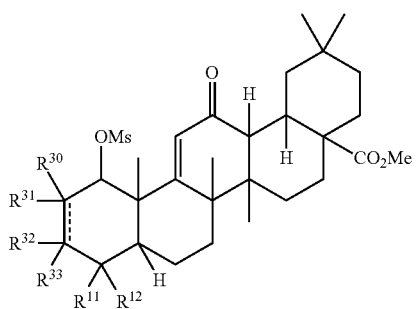

Formula XV

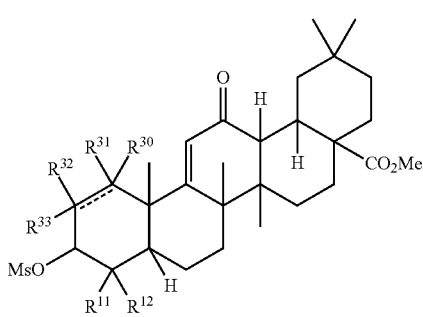

Formula XVI wherein

R$^{11}$ and R$^{12}$ are each independently hydrogen, hydroxyl, halo, alkyl, alkenyl, alkynyl, aryl, aralkyl, heteroaryl, heteroaralkyl, acyl, alkoxy, aryloxy, aralkoxy, heteroaryloxy, hetero-aralkoxy, acyloxy, alkylamino, dialkylamino, arylamino, aralkylamino, heteroarylamino, heteroaralkylamino, amido, or a substituted version of any of these groups, or R$^{11}$ and R$^{12}$ are taken together and are alkanediyl, alkenediyl, arenediyl, alkoxydiyl, alkenyloxydiyl, alkylaminodiyl, alkenylaminodiyl, or alkenylaminooxydiyl;

R$^{30}$, R$^{31}$, R$^{32}$ and R$^{33}$ are each independently a hydrogen, cyano, —OMs, or —CH$_2$OMs group; or R$^{30}$ and R$^{31}$ or R$^{32}$ and R$^{33}$ together are =CH$_2$; and dashed bonds are either present or absent.

2. A pharmaceutical composition comprising the compound of claim 1 in admixture with a pharmaceutically acceptable carrier.

3. A method for treating a degenerative disease comprising administering to a patient suffering from a degenerative disease an effective amount of a triterpenoid of claim 1 thereby treating the patient's degenerative disease, wherein the degenerative disease or is, cardiac injury or, myocardial infarction.

4. A method for treating a congenital disorder comprising administering to a patient suffering from a congenital disorder an effective amount of a triterpenoid of claim 1 thereby treating the patient's congenital disorder, wherein the congenital disorder is familial dysautonomia, or a congenital heart defect.

* * * * *

UNITED STATES PATENT AND TRADEMARK OFFICE
CERTIFICATE OF CORRECTION

PATENT NO. : 9,205,113 B2  
APPLICATION NO. : 14/395157  
DATED : December 8, 2015  
INVENTOR(S) : Gordon W. Gribble et al.

Page 1 of 1

It is certified that error appears in the above-identified patent and that said Letters Patent is hereby corrected as shown below:

IN THE CLAIMS

At Column 66, line 21, delete "disease or is, cardiac injury or, myocardial"

At Column 66, line 21, add --disease is cardiac injury or myocardial--

Signed and Sealed this
Ninth Day of February, 2016

Michelle K. Lee
*Director of the United States Patent and Trademark Office*